United States Patent
Ganesan et al.

(10) Patent No.: US 11,207,180 B2
(45) Date of Patent: *Dec. 28, 2021

(54) SYSTEMS AND METHODS FOR HEART VALVE THERAPY

(71) Applicant: Caisson Interventional, LLC, Maple Grove, MN (US)

(72) Inventors: Kavitha Ganesan, Minnetrista, MN (US); Andrew T. Forsberg, Plymouth, MN (US); Cyril J. Schweich, Jr., Maple Grove, MN (US); Todd J. Mortier, Mound, MN (US)

(73) Assignee: Caisson Interventional, LLC, Maple Grove, MN (US)

( * ) Notice: Subject to any disclaimer, the term of this patent is extended or adjusted under 35 U.S.C. 154(b) by 179 days.

This patent is subject to a terminal disclaimer.

(21) Appl. No.: 16/282,534

(22) Filed: Feb. 22, 2019

(65) Prior Publication Data

US 2019/0183641 A1 Jun. 20, 2019

Related U.S. Application Data

(63) Continuation of application No. 15/235,414, filed on Aug. 12, 2016, now Pat. No. 10,213,301.

(Continued)

(51) Int. Cl.
*A61F 2/24* (2006.01)
*A61B 1/00* (2006.01)
(Continued)

(52) U.S. Cl.
CPC ........ *A61F 2/2436* (2013.01); *A61B 1/00147* (2013.01); *A61F 2/2409* (2013.01);
(Continued)

(58) Field of Classification Search
CPC ........ A61F 2/24; A61F 2/2412; A61F 2/2466; A61F 2/2418; A61F 2/2436;
(Continued)

(56) References Cited

U.S. PATENT DOCUMENTS 2,638,301 A 5/1953 Smith
9,750,606 B2 * 9/2017 Ganesan .............. A61F 2/2427
(Continued)

FOREIGN PATENT DOCUMENTS

| EP | 2893898 A1 | 7/2015 |
|---|---|---|
| WO | WO 2009/092059 | 7/2009 |
| WO | 2014/064694 A2 | 5/2014 |

OTHER PUBLICATIONS

European Search Report in Application No. 16837570.7, dated Jun. 1, 2018, 6 pages.
(Continued)

*Primary Examiner* — Vi X Nguyen
(74) *Attorney, Agent, or Firm* — Faegre Drinker Biddle & Reath LLP

(57) ABSTRACT

Prosthetic heart valves described herein can be deployed using a transcatheter delivery system and technique to interface and anchor in cooperation with the anatomical structures of a native heart valve. Deployment systems and methods for using the deployment systems described herein facilitate accurately and conveniently controllable percutaneous, transcatheter techniques by which the prosthetic heart valves can be delivered and deployed within a patient.

17 Claims, 32 Drawing Sheets

Related U.S. Application Data

(60) Provisional application No. 62/205,355, filed on Aug. 14, 2015.

(51) Int. Cl.
    *A61M 25/01*     (2006.01)
    *A61F 2/95*     (2013.01)

(52) U.S. Cl.
    CPC ....... *A61F 2/2439* (2013.01); *A61M 25/0113* (2013.01); *A61F 2/2418* (2013.01); *A61F 2/9517* (2020.05)

(58) Field of Classification Search
    CPC ........ A61F 2/2409; A61F 2/95; A61F 2/2439; A61F 2/2427; A61M 25/0113; A61M 25/01; A61B 1/00147
    See application file for complete search history.

(56) References Cited

U.S. PATENT DOCUMENTS

| | | |
|---|---|---|
| 10,213,301 B2 * | 2/2019 | Ganesan ................ A61B 90/50 |
| 2002/0177789 A1 | 11/2002 | Ferry et al. |
| 2003/0069523 A1 | 4/2003 | Williams et al. |
| 2009/0247942 A1 | 10/2009 | Kirschenman |
| 2009/0270677 A1 | 10/2009 | Dillon |
| 2010/0010475 A1 | 1/2010 | Teirstein et al. |
| 2010/0286478 A1 | 11/2010 | Ewers et al. |
| 2010/0298845 A1 | 11/2010 | Kidd et al. |
| 2011/0015490 A1 | 1/2011 | Trovato et al. |
| 2011/0040150 A1 | 2/2011 | Govar et al. |
| 2011/0105954 A1 | 5/2011 | Cohen et al. |
| 2011/0130718 A1 | 6/2011 | Kidd et al. |
| 2011/0152609 A1 | 6/2011 | Trusty et al. |
| 2012/0004502 A1 | 1/2012 | Weitzner et al. |
| 2013/0066342 A1 | 3/2013 | Dell et al. |
| 2013/0172992 A1 * | 7/2013 | Gross ................... A61B 17/068 623/2.11 |
| 2014/0378761 A1 | 12/2014 | Zorn et al. |
| 2015/0112433 A1 | 4/2015 | Schweich et al. |

OTHER PUBLICATIONS

International Preliminary Report on Patentability in International Application No. PCT/US2016/046727, dated Feb. 20, 2018, 7 pages.

International Search Report and Written Opinion in International Application No. PCT/US2016/046727, dated Oct. 28, 2016, 8 pages.

\* cited by examiner

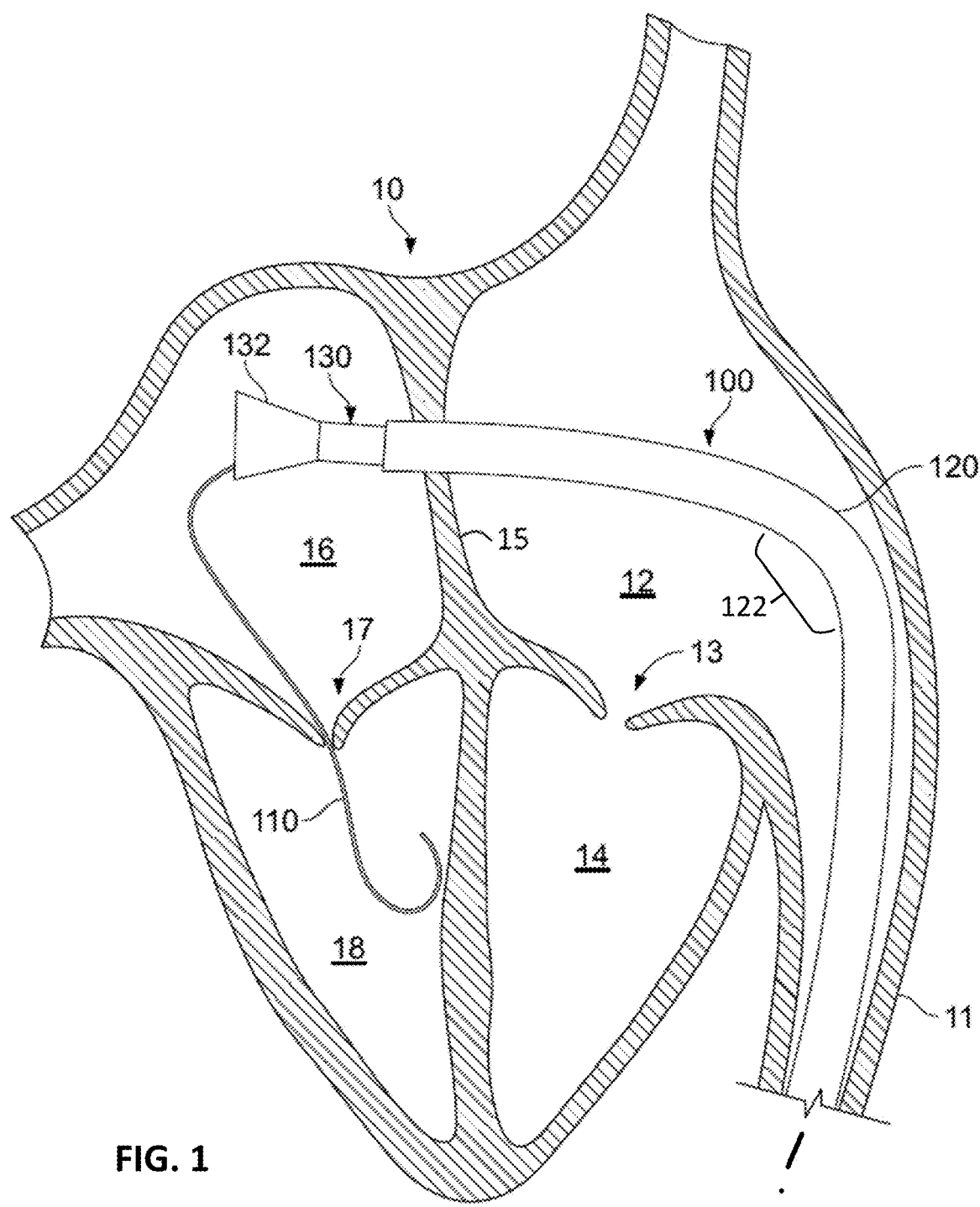
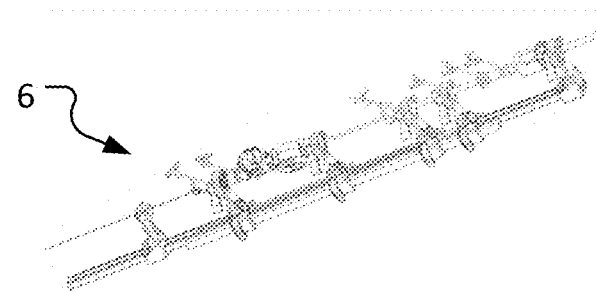
FIG. 1

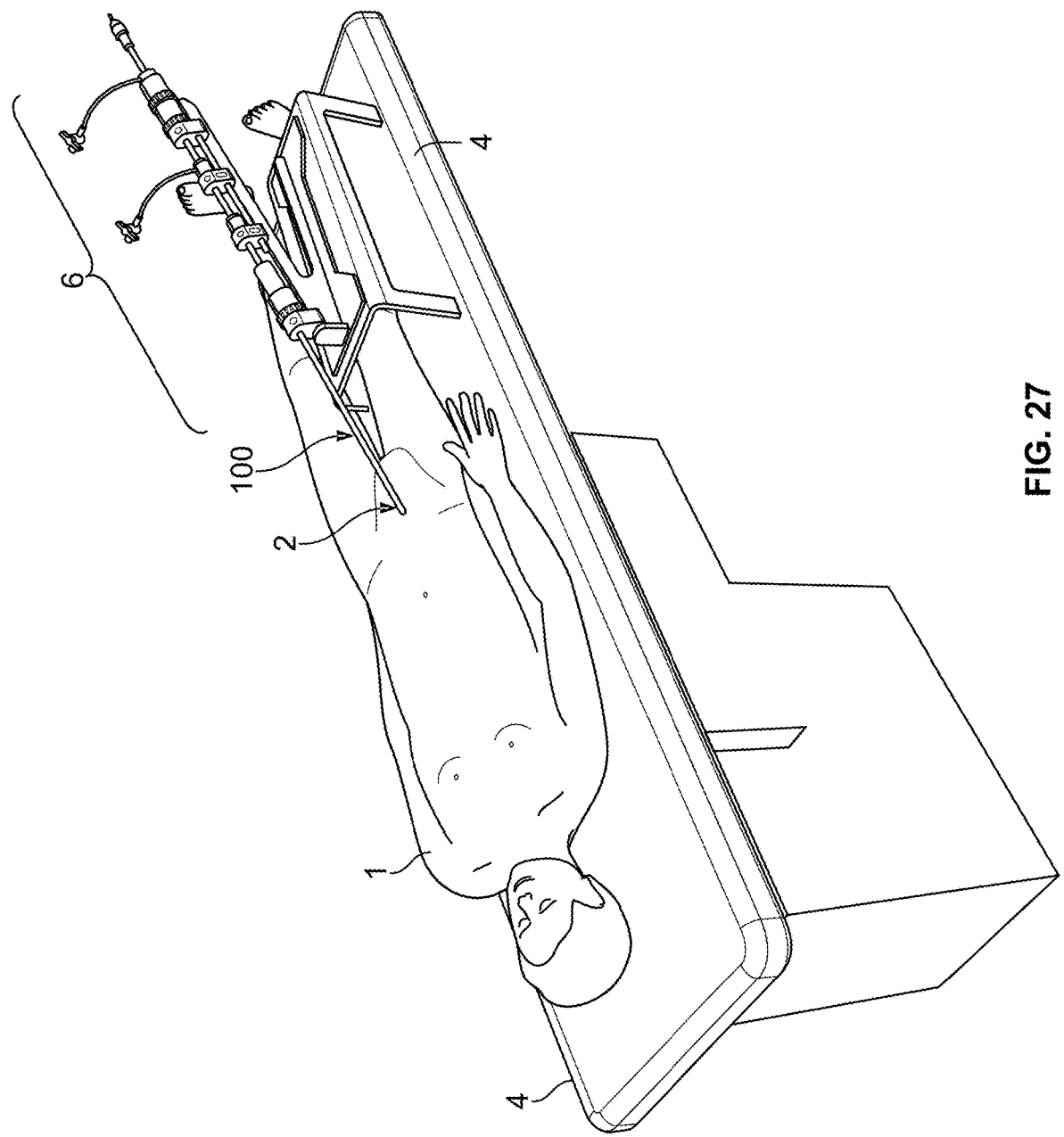

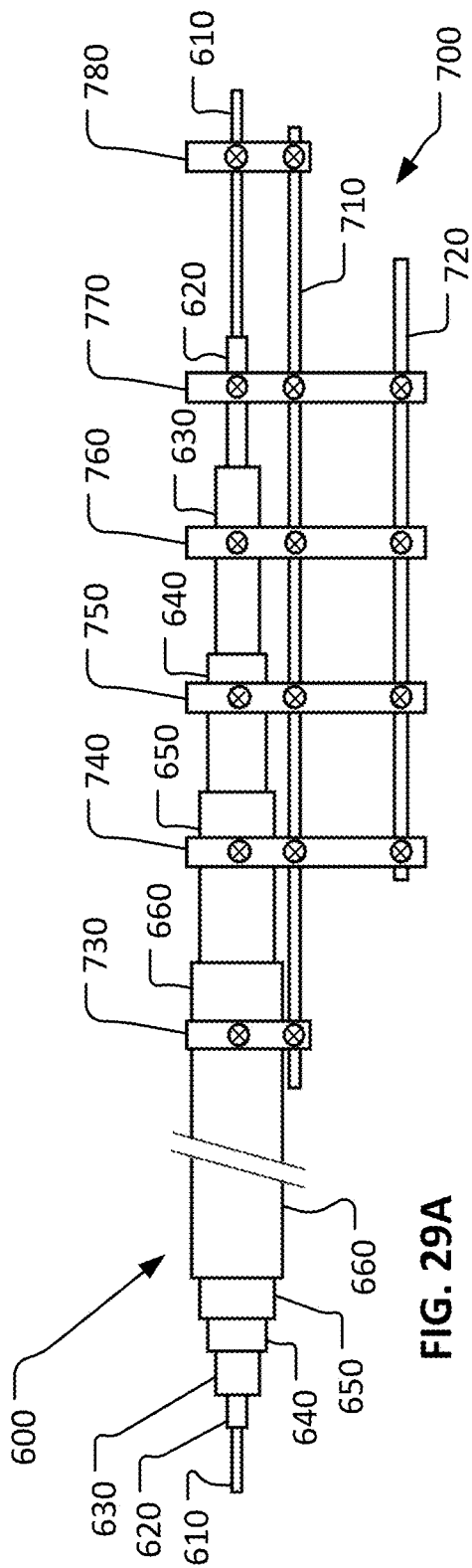
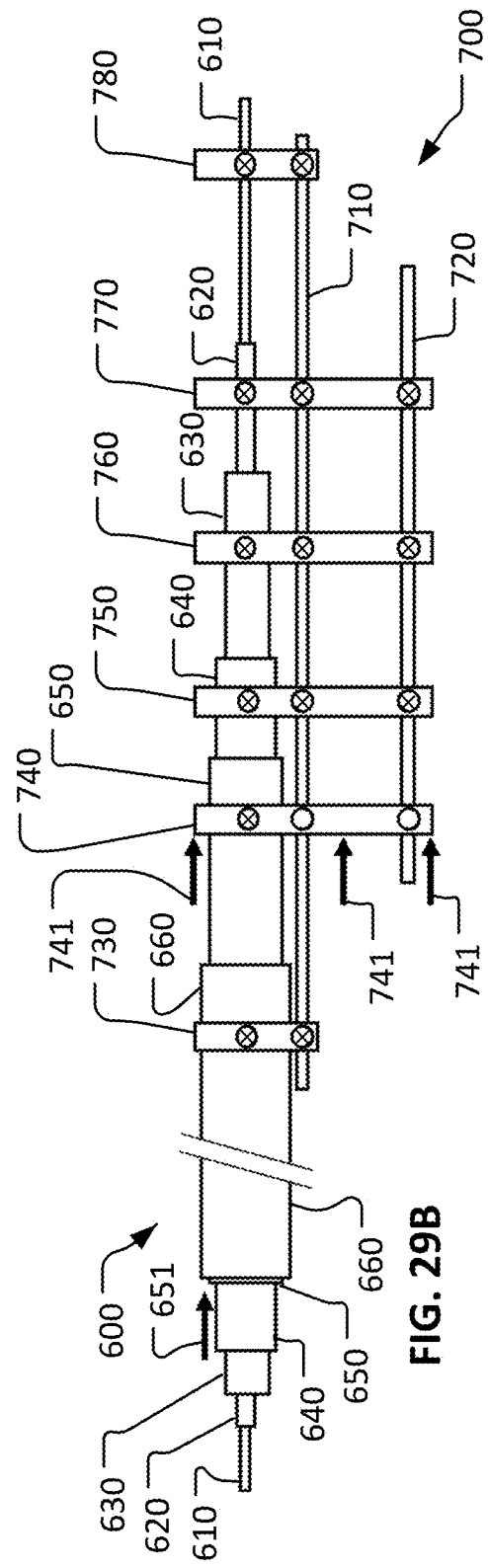
FIG. 29A
FIG. 29B

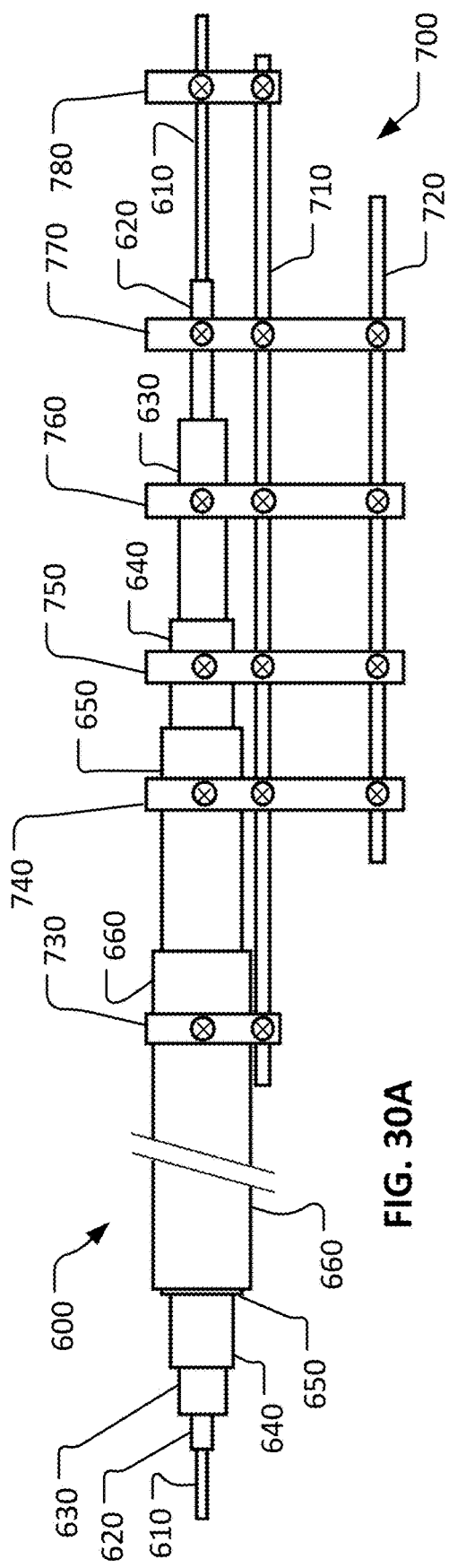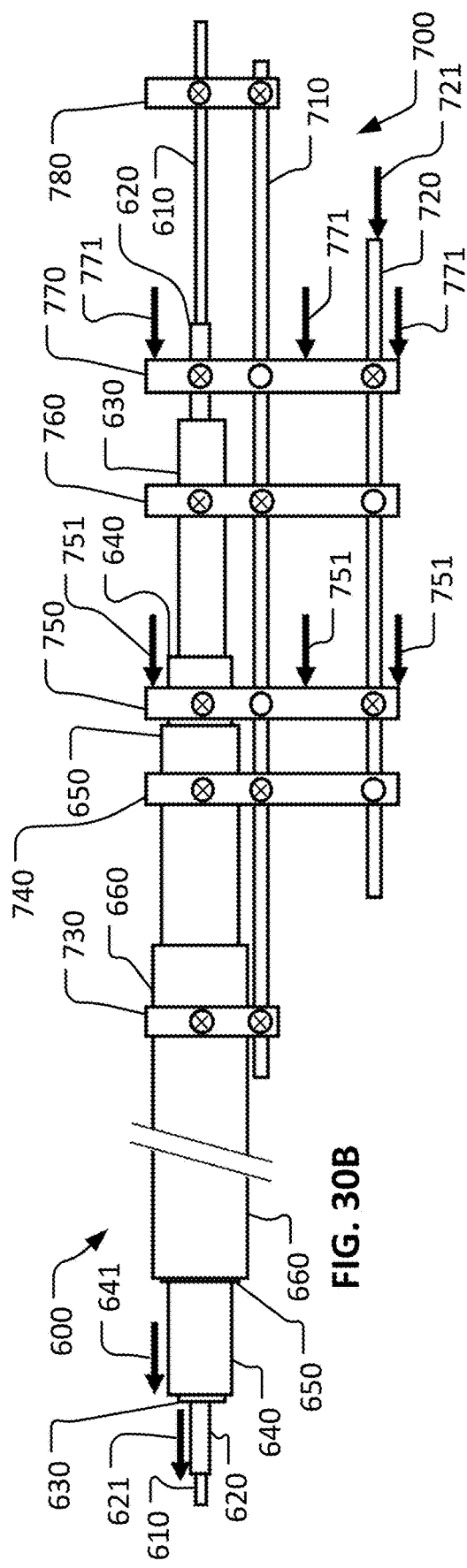
FIG. 30A
FIG. 30B

SYSTEMS AND METHODS FOR HEART VALVE THERAPY

CROSS-REFERENCE TO RELATED APPLICATIONS

This application is a continuation of U.S. application Ser. No. 15/235,414 filed on Aug. 12, 2016, and entitled "Systems and Methods for Heart Valve Therapy," which claims the benefit of U.S. Provisional Application Ser. No. 62/205,355, filed Aug. 14, 2015. The disclosure of these prior applications is considered part of (and is incorporated by reference in) the disclosure of this application.

TECHNICAL FIELD

This document relates to prosthetic heart valves, such as prosthetic mitral valves that can be implanted using transcatheter techniques. This document also relates to systems for actuating and controlling the percutaneous deployment of prosthetic mitral valves using transcatheter techniques.

BACKGROUND

The long-term clinical effect of valve regurgitation is recognized as a significant contributor to cardiovascular related morbidity and mortality. Thus, for many therapies intended to treat the mitral valve, one primary goal is to significantly reduce or eliminate regurgitation. By eliminating the regurgitation at the mitral valve, the destructive volume overload effects on the left ventricle can be attenuated. The volume overload of mitral regurgitation (MR) relates to the excessive kinetic energy required during isotonic contraction to generate overall stroke volume in an attempt to maintain forward stroke volume and cardiac output. It also relates to the pressure potential energy dissipation of the leaking valve during the most energy-consuming portion of the cardiac cycle, isovolumetric contraction. Additionally, therapies for MR reduction can have the effect of reducing the elevated pressures in the left atrium and pulmonary vasculature reducing pulmonary edema (congestion) and shortness of breath symptomatology. Such therapies for MR reduction may also have a positive effect on the filling profile of the left ventricle (LV) and the restrictive LV physiology that can result with MR. These pathophysiologic issues indicate the potential benefits of MR therapy, but also indicate the complexity of the system and the need for a therapy to focus beyond the MR level or grade.

In some percutaneous access procedures in which a medical device is introduced through a patient's skin and into a patient's blood vessel, such an access can be used to introduce devices into the patient without the use of large cut downs, which can be painful and in some cases can hemorrhage or become infected. A percutaneous access generally employs only a small hole through the skin, which subsequently seals relatively easily, and heals quickly in comparison to a surgical cut down.

SUMMARY

This document describes prosthetic heart valves, such as prosthetic mitral valves, that interface and anchor in cooperation with the anatomical structures of a native mitral valve. In addition, this document describes multiple embodiments of medical device delivery systems, for example, to deliver a prosthetic heart valve or other medical device through a patient's vasculature, and also describes methods for percutaneous, transcatheter delivery and deployment of medical devices including, but not limited to, prosthetic heart valves.

In some implementations, a prosthetic mitral valve and deployment system includes a prosthetic mitral valve system, a system of multiple catheters configured to deliver the prosthetic mitral valve system, and a deployment frame system. At least some catheters of the multiple catheters are slidably engageable with each other. At least a first catheter of the multiple catheters is releasably coupleable to the prosthetic anchor assembly. At least a second catheter of the multiple catheters is releasably coupleable to the prosthetic valve assembly. The prosthetic mitral valve system can include a prosthetic anchor assembly comprising an anchor frame that defines an interior space, and a prosthetic valve assembly comprising a valve frame and multiple valve leaflets attached to the valve frame. The valve frame is configured to releasably couple with the prosthetic anchor assembly within the interior space. The deployment frame includes a plurality of clamps, a first frame, and a second frame. Each clamp of the plurality of clamps is configured to releasably clamp a proximal end portion of a respective catheter of the multiple catheters. Each clamp of the plurality of clamps is configured to releasably couple with the first frame. At least one clamp of the plurality of clamps is configured to releasably couple with the second frame.

Such a prosthetic mitral valve and deployment system may optionally include one or more of the following features. The prosthetic anchor assembly may include a hub attached to the anchor frame. In some embodiments, the first catheter is releasably coupleable to the hub. One or more control wires may releasably couple the second catheter to the prosthetic valve assembly. Each clamp of the plurality of clamps may be configured to slidably engage with the first frame. The at least one clamp of the plurality of clamps may be configured to slidably engage with the second frame. The at least one clamp of the plurality of clamps may be configured to slidably engage with the first frame and with the second frame. Each catheter that is releasably clamped to a clamp may be rotatable, in relation the clamp, about a longitudinal axis of the catheter. Two or more clamps of the plurality of clamps may be configured to releasably couple with the second frame. The two or more clamps of the plurality of clamps may be lockable to the second frame and unlockable from the first frame such that a translational movement of the second frame simultaneously moves the two or more clamps of the plurality of clamps in relation to the first frame. The translational movement of the second frame may cause corresponding simultaneous movements of two or more catheters of the multiple catheters.

In another implementation, a method of implanting a prosthetic mitral valve in a patient includes: (a) inserting, into the patient, a system of multiple catheters configured to deliver the prosthetic mitral valve; (b) engaging, to a deployment frame system, the system of multiple catheters; and (c) manipulating the deployment frame system to implant the prosthetic mitral valve in the patient. The deployment frame system may include a plurality of clamps, a first frame, and a second frame. At least one clamp of the plurality of clamps is configured to releasably couple with the second frame. Each clamp of the plurality of clamps configured to releasably clamp a proximal end portion of a respective catheter of the multiple catheters. Each clamp of the plurality of clamps is configured to releasably couple with the first frame.

Such a method of implanting a prosthetic mitral valve in a patient may optionally include one or more of the following features. The manipulating the deployment frame system may include a translational movement of the second frame in relation to the first frame. Two or more clamps of the plurality of clamps may be releasably coupled with the second frame. In some embodiments, the translational movement of the second frame causes simultaneous movements of two or more catheters of the multiple catheters. The manipulating the deployment frame system may include rotating at least one catheter of the multiple catheters about a longitudinal axis of the at least one catheter, and in relation to a clamp with which the at least one catheter is releasably clamped.

In another implementation, a medical device deployment system includes a system of multiple catheters configured to deliver a medical device and a deployment frame system. At least some catheters of the multiple catheters are slidably engageable with each other. At least one catheter of the multiple catheters is releasably coupleable with the medical device. The deployment frame system includes: (i) a plurality of clamps, each clamp of the plurality of clamps configured to releasably clamp a proximal end portion of a respective catheter of the multiple catheters; (ii) a first frame, wherein at least two clamps of the plurality of clamps are configured to releasably couple with the first frame; and (iii) a second frame, wherein at least one clamp of the plurality of clamps is configured to releasably couple with the second frame.

Such a medical device deployment system may optionally include one or more of the following features. One or more control wires may be used to releasably couple the at least one catheter with the medical device. Each clamp of the plurality of clamps may be configured to slidably engage with the first frame. The at least one clamp of the plurality of clamps may be configured to slidably engage with the second frame. The at least one clamp of the plurality of clamps may be configured to slidably engage with the first frame and with the second frame. Each catheter that is releasably clamped to a clamp may be rotatable, in relation the clamp, about a longitudinal axis of the catheter. Two or more clamps of the plurality of clamps may be configured to releasably couple with the second frame. The two or more clamps of the plurality of clamps may be lockable to the second frame and unlockable from the first frame such that a translational movement of the second frame simultaneously moves the two or more clamps of the plurality of clamps in relation to the first frame. The translational movement of the second frame may cause corresponding simultaneous movements of two or more catheters of the multiple catheters.

In another implementation, a deployment frame system for controlling relative movements of a system of multiple catheters wherein at least one catheter of the multiple catheters is configured to deliver a medical device includes: (1) a plurality of clamps, each clamp of the plurality of clamps configured to releasably clamp a proximal end portion of a respective catheter of the multiple catheters; (2) a first frame, wherein at least two clamps of the plurality of clamps are configured to releasably couple with the first frame; and (3) a second frame, wherein at least one clamp of the plurality of clamps is configured to releasably couple with the second frame.

In another implementation, a prosthetic mitral valve and deployment system includes a prosthetic mitral valve, a system of multiple catheters configured to deliver the prosthetic mitral valve, and a deployment frame system. At least some catheters of the multiple catheters are slidably engageable with each other. One or more catheters of the multiple catheters are releasably coupleable to the prosthetic mitral valve. The deployment frame system includes a plurality of clamps, a first frame, and a second frame. Each clamp of the plurality of clamps is configured to releasably clamp a proximal end portion of a respective catheter of the multiple catheters. Each clamp of the plurality of clamps is configured to releasably couple with the first frame. At least one clamp of the plurality of clamps is configured to releasably couple with the second frame.

Such a prosthetic mitral valve and deployment system may optionally include one or more of the following features. The prosthetic mitral valve may include a hub, and the first catheter may be releasably coupleable to the hub. One or more control wires may releasably couple the second catheter to the prosthetic mitral valve. Each clamp of the plurality of clamps may be configured to slidably engage with the first frame. The at least one clamp of the plurality of clamps may be configured to slidably engage with the second frame. The at least one clamp of the plurality of clamps may be configured to slidably engage with the first frame and with the second frame. Each catheter that is releasably clamped to a clamp may be rotatable, in relation the clamp, about a longitudinal axis of the catheter. Two or more clamps of the plurality of clamps may be configured to releasably couple with the second frame. The two or more clamps of the plurality of clamps may be lockable to the second frame and unlockable from the first frame such that a translational movement of the second frame simultaneously moves the two or more clamps of the plurality of clamps in relation to the first frame. The translational movement of the second frame may cause corresponding simultaneous movements of two or more catheters of the multiple catheters.

In another implementation, a method of implanting a prosthetic mitral valve in a patient includes: inserting, into the patient, a system of multiple catheters configured to deliver the prosthetic mitral valve; engaging, to a deployment frame system, the system of multiple catheters; and manipulating the deployment frame system to implant the prosthetic mitral valve in the patient. The prosthetic mitral valve includes an anchor assembly and a valve assembly that is configured to couple with the anchor assembly. The deployment frame system includes a plurality of clamps, a first frame, and a second frame. Each clamp of the plurality of clamps is configured to releasably clamp a proximal end portion of a respective catheter of the multiple catheters. Each clamp of the plurality of clamps is configured to releasably couple with the first frame. At least one clamp of the plurality of clamps is configured to releasably couple with the second frame.

Some or all of the embodiments described herein may provide one or more of the following advantages. First, the transcatheter prosthetic heart valve deployment systems described herein are configured to facilitate accurate control of the catheter systems and prosthetic valve components during the delivery and deployment process. In some embodiments, proximal-end controls of the delivery system catheters are mounted to a stable base in relation to the patient, and mounted in a manner that allows for isolated, accurate movements of each degree of freedom associated with the catheters and prosthetic valve components. Accordingly, relatively complex catheter and/or valve component movements are facilitated in an accurately controllable and user-convenient manner. In result, transcatheter implant procedures can be performed with enhanced patient safety and treatment effectiveness using the deployment systems described herein.

Second, some embodiments of the transcatheter prosthetic heart valve deployment systems described herein are configured to facilitate simultaneous movement of two or more components of the deployment system, corresponding to two or more movements of the catheter delivery system. For example, as described further below, some embodiments of the transcatheter prosthetic heart valve deployment systems include two frames (e.g., a main frame and a secondary frame) that facilitate such simultaneous movements. In result, relatively complex movements of two or more components simultaneously, can be readily performed using the transcatheter prosthetic heart valve deployment systems and methods described herein.

Third, some embodiments of the prosthetic mitral valve systems provided herein can be used in a completely percutaneous/transcatheter mitral replacement procedure that is safe, reliable, and repeatable by surgeons and/or interventional cardiologists of a variety of different skill levels. For example, in some implementations the prosthetic mitral valve system can establish a reliable and consistent anchor/substrate to which the valve/occluder structure subsequently engages. Thus, the prosthetic mitral valve system can be specifically designed to make use of the geometry/mechanics of the native mitral valve to create sufficient holding capability. In one particular aspect, the anatomical gutter found below a native mitral valve annulus can be utilized as a site for anchoring the prosthetic mitral valve system, yet the anchoring structure can be deployed in a matter that maintains native leaflet function of the mitral valve, thereby providing the ability to completely separate and stage the implantation of the components of the prosthetic mitral valve system. Accordingly, some embodiments of the prosthetic mitral valve systems described herein are configured to be implanted in a reliable, repeatable, and simplified procedure that is broadly applicable to a variety of patients and physicians, while also employing a significantly less invasive method.

Fourth, in particular embodiments, the prosthetic mitral valve system can include two different expandable components (e.g., an anchor assembly and a valve assembly) that are separately delivered to the implantation site, and both components can abut and engage with native heart tissue at the mitral valve. For example, the first component (e.g., the anchor assembly) can be configured to engage with the heart tissue that is at or proximate to the annulus of the native mitral valve, and the second component (e.g., the valve assembly) can be configured to provide a seal interface with native valve leaflets of the mitral valve.

Fifth, using the devices, systems, and methods described herein, various medical conditions, such as heart valve conditions, can be treated in a minimally invasive fashion. Such minimally invasive techniques can tend to reduce recovery times, patient discomfort, and treatment costs.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a perspective view of a portion of a prosthetic mitral valve deployment system in a cross-sectional view of a native human heart, in accordance with some embodiments.

FIG. 27 shows a perspective view of a patient on an operating table undergoing a percutaneous deployment of an implantable prosthetic using a deployment frame system in accordance with some embodiments.

FIGS. 29A and 29B are schematic depictions of a catheter system and deployment frame system which illustrate the movement of an individual catheter system component.

FIGS. 30A and 30B are schematic depictions of a catheter system and deployment frame system which illustrate the movement of a group of catheter system components in unison with each other.

Like reference symbols in the various drawings indicate like elements.

DETAILED DESCRIPTION OF ILLUSTRATIVE EMBODIMENTS

Figure 2:
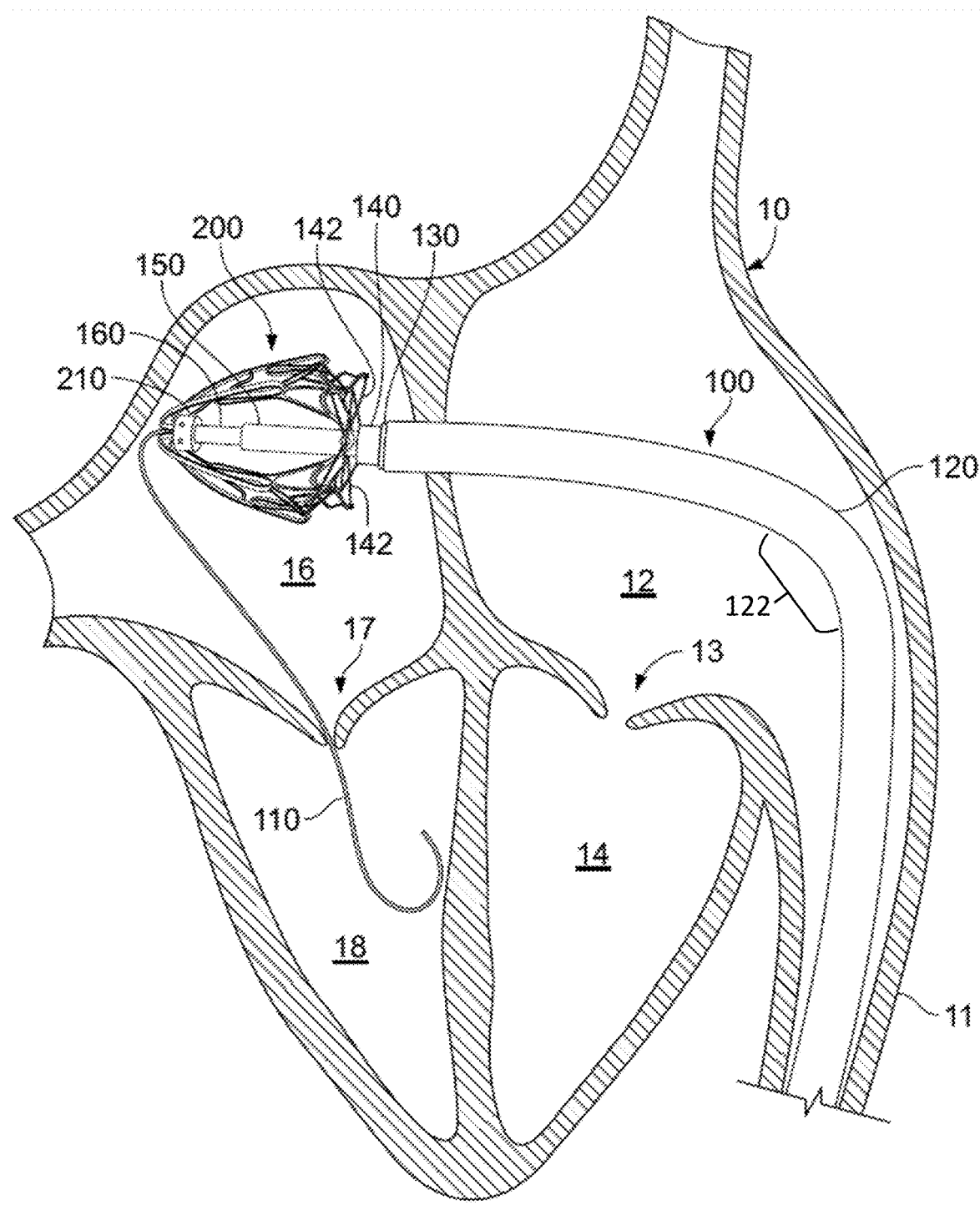
FIG. 2 shows a perspective view of a prosthetic mitral valve anchor assembly in the left atrium of the heart after the anchor assembly has emerged from an anchor delivery sheath of the deployment system of FIG. 1

This disclosure describes embodiments of a prosthetic heart valve system, such as prosthetic mitral valve systems, and transcatheter systems and methods for implanting prosthetic heart valve systems. In some embodiments, the prosthetic mitral valve system can be deployed to interface and anchor in cooperation with the native anatomical structures of a mitral valve (and, optionally, in a manner that permits the continued natural function of the chordae tendineae of the native mitral valve leaflets even after the anchor component is deployed). As described in more detail below, FIGS. 1-26 describe prosthetic mitral valves, and transcatheter mitral valve delivery systems and methods by which the prosthetic mitral valves can be deployed to interface and anchor in cooperation with the anatomical structures of a native mitral valve. Also, in FIGS. 27-36, multiple deployment frame system embodiments and methods for using the deployment frame systems are described by which the prosthetic mitral valves described herein can be delivered and deployed within a patient using percutaneous, transcatheter techniques.

Referring to FIG. 1, an example transcatheter mitral valve delivery system 100 can be navigated through a patient's vasculature to obtain access to the patient's heart 10. The transcatheter delivery system 100 facilitates implantation of a prosthetic mitral valve in a beating heart 10 using a percutaneous, or minimally invasive technique (without open-chest surgery or open-heart). For example, in some implementations the transcatheter delivery system 100 is percutaneously inserted into a femoral or iliac vein via a groin opening/incision 2 in a patient 1 (FIG. 27) using a deployment frame system 6 (FIGS. 1 and 27) configured to activate and/or control the movements of various components of the transcatheter delivery system 100. In some implementations, the transcatheter delivery system 100 is used in conjunction with one or more imaging modalities such as x-ray fluoroscopy, echocardiography, magnetic resonance imaging, computed tomography (CT), and the like.

The heart 10 (depicted in cross-section from a posterior perspective in FIG. 1) includes a right atrium 12, a right ventricle 14, a left atrium 16, and a left ventricle 18. A tricuspid valve 13 separates the right atrium 12 from the right ventricle 14. A mitral valve 17 separates the left atrium 16 from the left ventricle 18. An atrial septum 15 separates the right atrium 12 from the left atrium 16. An inferior vena cava 11 is confluent with the right atrium 12. It should be understood that this depiction of the heart 10 is somewhat stylized. The same is true for FIGS. 2-4. FIGS. 1-4 provide general depictions of the approach to the mitral valve 17 that is used in some implementations. But, the commissural cross-sectional views of FIG. 5 and thereafter more accurately depict the orientation of the prosthetic mitral valves in relation to the heart 10.

Still referring to FIG. 1, in the depicted embodiment, the delivery system 100 includes a guidewire 110, a guide catheter 120, and an anchor delivery sheath 130. Additional components of the delivery system 100 will be described further below. The anchor delivery sheath 130 is slidably (and rotationally) disposed within a lumen of the guide catheter 120. The guidewire 110 is slidably disposed with respect to a lumen of the anchor delivery sheath 130. In this depiction, the anchor delivery sheath 130 has been partially extended relative to the guide catheter 120, allowing a flared portion 132 to expand outward, as described further below.

In the depicted implementation, the guidewire 110 is installed into the heart 10 prior to the other components of the delivery system 100. In some embodiments, the guidewire 110 has a diameter of about 0.035 inches (about 0.89 mm). In some embodiments, the guidewire 110 has a diameter in a range of about 0.032 inches to about 0.038 inches (about 0.8 mm to about 0.97 mm). In some embodiments, the guidewire 110 has a diameter smaller than 0.032 inches (about 0.80 mm) or larger than 0.038 inches (about 0.97 mm). In some embodiments, the guidewire 110 is made of materials such as, but not limited to, nitinol, stainless steel, high-tensile-strength stainless steel, and the like, and combinations thereof. The guidewire 110 may include various tip designs (e.g., J-tip, straight tip, etc.), tapers, coatings, covers, radiopaque (RO) markers, and other features. In some embodiments, the guidewire 110 has one or more portions with differing lateral stiffnesses, column strengths, lubricity, and/or other physical properties in comparison to other portions of the guidewire 110.

In some implementations, the guidewire 110 is percutaneously inserted into a femoral vein of the patient. The guidewire 110 is routed to the inferior vena cava 11 and into the right atrium 12. After creating an opening in the atrial septum 15 (e.g., a trans-septal puncture of the fossa ovalis or other portion of the atrial septum), the guidewire 110 is routed into the left atrium 16. Lastly, the guidewire 110 is routed through the mitral valve 17 and into the left ventricle 18. This is preferably performed without entangling the guidewire 110 with the chordae tendineae of the mitral valve 17. In some implementations, the guidewire 110 can be installed into the heart 10 along other anatomical pathways. The guidewire 110 thereafter serves as a rail over which other components of the delivery system 100 are passed.

In the depicted implementation, the guide catheter 120 is installed (e.g., via the groin incision 2, refer to FIG. 27) by pushing it over the guidewire 110. In some implementations, a dilator tip is used in conjunction with the guide catheter 120 as the guide catheter 120 is advanced over the guidewire 110. Alternatively, a balloon catheter could be used as the initial dilation means. After the distal end of the guide catheter 120 reaches the left atrium 16, the dilator tip can be withdrawn.

By making various adjustments at the proximal end of the guide catheter 120 (as described further below), a clinician can attain a desirable orientation of the guide catheter 120 in relation to the heart 10. For example, the guide catheter 120 can be rotated about its longitudinal axis so that the longitudinal axis of the distal-most tip portion of the guide catheter 120 is pointing toward the perpendicular axis of the mitral valve 17. Such rotational movement of the guide catheter 120 can be performed by the clinician as described further below. In addition, in some embodiments a distal end portion of the guide catheter 120 is steerable (also referred to herein as "deflectable"). Using such steering, the distal end portion of the guide catheter 120 can be deflected to navigate the patient's anatomy and/or to be positioned in relation to the patient's anatomy as desired. For example, the guide catheter 120 can be angled within the right atrium 12 to navigate the guide catheter 120 from the inferior vena cava 11 to the atrial septum 15. Accordingly, in some embodiments the guide catheter 120 may include at least one deflection zone 122. As described further below, a clinician can controllably deflect the deflection zone of the guide catheter 120 as desired.

After the guide catheter 120 is oriented within the heart 10 as desired by the clinician, in some embodiments the clinician can releasably lock the guide catheter 120 in the desired orientation. For example, as described further below, in some embodiments the clinician can releasably lock the guide catheter 120 to a frame assembly that is stationary in relation to the patient.

Still referring to FIG. 1, in some embodiments the guide catheter 120 has an outer diameter of about 28 Fr (about 9.3 mm), or about 30 Fr (about 10.0 mm). In some embodiments, the guide catheter 120 has an outer diameter in the range of about 26 Fr to about 34 Fr (about 8.7 mm to about 11.3 mm). In some embodiments, the guide catheter 120 has an outer diameter in the range of about 20 Fr to about 28 Fr (about 6.7 mm to about 9.3 mm).

The guide catheter 120 can comprise a tubular polymeric or metallic material. For example, in some embodiments the guide catheter 120 can be made from polymeric materials such as, but not limited to, polytetrafluoroethylene (PTFE), fluorinated ethylene propylene (FEP), HYTREL®, nylon, PICOFLEX®, PEBAX®, TECOFLEX®, and the like, and combinations thereof. In alternative embodiments, the guide catheter 120 can be made from metallic materials such as, but not limited to, nitinol, stainless steel, stainless steel alloys, titanium, titanium alloys, and the like, and combinations thereof. In some embodiments, the guide catheter 120 can be made from combinations of such polymeric and metallic materials (e.g., polymer layers with metal braid, coil reinforcement, stiffening members, and the like, and combinations thereof). In some embodiments, the guide catheter 120 can comprise a slotted tube.

The example delivery system 100 also includes the anchor delivery sheath 130. In some implementations, after the guide catheter 120 is positioned with its distal end in the left atrium 16, the anchor delivery sheath 130 is installed into a lumen of the guide catheter 120 (over the guidewire 110) and advanced through the guide catheter 120. As described further below, in some embodiments the anchor delivery sheath 130 is preloaded with a prosthetic valve anchor assembly and other components of the delivery system 100.

In some embodiments, the anchor delivery sheath 130 can be made from the materials described above in reference to the guide catheter 120. In some embodiments, the anchor delivery sheath 130 has an outer diameter in the range of about 20 Fr to about 28 Fr (about 6.7 mm to about 9.3 mm). In some embodiments, the anchor delivery sheath 130 has an outer diameter in the range of about 14 Fr to about 24 Fr (about 4.7 mm to about 8.0 mm).

In the depicted embodiment, the anchor delivery sheath 130 includes a flared distal end portion 132. In some embodiments, no such flared distal end portion 132 is included. The flared distal end portion 132 can collapse to a lower profile when constrained within the guide catheter 120. When the flared distal end portion 132 is expressed from the guide catheter 120, the flared distal end portion 132 can self-expand to the flared shape. In some embodiments, the material of the flared distal end portion 132 includes pleats or folds, may be a continuous flared end or may be separated into sections resembling flower petals, and may include one or more resilient elements that bias the flared distal end portion 132 to assume the flared configuration in the absence of restraining forces (such as from containment within the guide catheter 120). The flared distal end portion 132 can be advantageous, for example, for recapturing (if desired) the anchor assembly within the lumen of the anchor delivery sheath 130 after the anchor assembly has been expressed from the flared distal end portion 132.

In some embodiments, the maximum outer diameter of the flared distal end portion 132 is in a range of about 30 Fr to about 34 Fr (about 10.0 mm to about 11.3 mm). In some embodiments, the maximum outer diameter of the flared distal end portion 132 is in a range of about 32 Fr to about 44 Fr (about 10.7 mm to about 14.7 mm). In some embodiments, the maximum outer diameter of the flared distal end portion 132 is in a range of about 24 Fr to about 30 Fr (about 8.0 mm to about 10.0 mm). In some embodiments, the maximum outer diameter of the flared distal end portion 132 is less than about 24 Fr (about 8.0 mm) or greater than about 44 Fr (about 14.7 mm).

Referring to FIG. 2, additional components of the example delivery system 100 can include an anchor delivery catheter 140, a secondary steerable catheter 150, and an inner catheter 160. The anchor delivery catheter 140 is slidably disposed within a lumen of the anchor delivery sheath 130. The secondary steerable catheter 150 is slidably disposed within a lumen of the anchor delivery catheter 140. The inner catheter 160 is slidably disposed within a lumen of the secondary steerable catheter 150. The guidewire 110 is slidably disposed within a lumen of the inner catheter 160.

An anchor assembly 200 is releasably attached to the inner catheter 160 and is, in effect, slidably disposed on the guidewire 110. As described further below, the components of the delivery system 100 can be individually or jointly manipulated by a clinician operator to control the position and orientation of the anchor assembly 200 during the deployment of the anchor assembly 200. In some implementations, a deployment frame system (such as the example deployment frame systems described below) is used to initiate and/or control the movements of various components of the transcatheter delivery system 100.

In a preferred implementation of delivery system 100, the anchor delivery catheter 140, the secondary steerable catheter 150, the inner catheter 160, and the anchor assembly 200 are loaded into the anchor delivery sheath 130 prior to the advancement of the anchor delivery sheath 130 into the guide catheter 120 as shown in FIG. 1. That is, in a preferred implementation the anchor delivery catheter 140, the secondary steerable catheter 150, the inner catheter 160, and/or the anchor assembly 200 are already installed in the anchor delivery sheath 130 as the anchor delivery sheath 130 is distally advanced into the guide catheter 120 to attain the arrangement shown in FIG. 1. Then the anchor delivery sheath 130 is individually pulled back (proximally) to reveal the anchor delivery catheter 140, the secondary steerable catheter 150, the inner catheter 160, and/or the anchor assembly 200 as shown in FIG. 2. The anchor assembly 200 may also be at least partially expanded. In some such implementations, the anchor delivery catheter 140, the secondary steerable catheter 150, the inner catheter 160, and/or the anchor assembly 200 are loaded into the anchor delivery sheath 130 in desired relative rotational orientations (i.e., rotational orientations about the longitudinal axis of the delivery system 100). In other implementations, one or more of the anchor delivery catheter 140, the secondary steerable catheter 150, the inner catheter 160, and the anchor assembly 200 are distally advanced into the anchor delivery sheath 130 after the anchor delivery sheath 130 has been advanced into the guide catheter 120 to attain the arrangement shown in FIG. 1.

The inner catheter 160 is releasably coupled with a hub 210 of the anchor assembly 200. One or more portions of the anchor assembly 200 are also releasably coupled to the anchor delivery catheter 140 by one or more control wires 142. In some embodiments, the one or more control wires 142 are slidably disposed within lumens of the anchor delivery catheter 140 and threaded through one or more portions of the anchor assembly 200 (e.g., through eyelets of the anchor assembly 200). While the depicted embodiment includes one control wire 142, in some embodiments two, three, four, five, or more than five control wires are included. For example, in a preferred embodiment two control wires 142 are included. One of the two control wires 142 is releasably coupled with a proximal end of the anchor assembly 200, and a second of the two control wires 142 is releasably coupled with a mid-body portion of the anchor assembly 200. A clinician can separately control the two control wires 142. In some implementations, a deployment frame system (such as the example deployment frame systems described below) is used to control the movements of the two control wires 142.

While the components of the delivery system 100 and the anchor assembly 200 are depicted in particular relative orientations and arrangements, it should be understood that the depictions are non-limiting. For example, in some implementations of the deployment process the distal tip of the secondary deflectable catheter 150 may always be, or may sometimes be, abutted to the hub 210 of the anchor assembly 200. Further, in some implementations of the deployment process the distal tip of the anchor delivery catheter 140 may always be, or may sometimes be, positioned within the interior of the anchor assembly 200. In some implementations, a deployment frame system (such as the example deployment frame systems described below) is used to control such relative arrangements and movements of the anchor delivery catheter 140 and secondary deflectable catheter 150 in relation to the anchor assembly 200, for example.

In some embodiments, the position of the anchor assembly 200 can be controlled by manipulating the relative positions of the inner catheter 160 and/or the anchor delivery catheter 140. For example, in the depicted embodiment the anchor assembly 200 can be expressed out from the anchor delivery sheath 130 (as shown in FIG. 2) by moving the inner catheter 160 and/or the anchor delivery catheter 140 distally in relation to the anchor delivery sheath 130. In some implementations, the expression of the anchor assembly 200 is caused by proximally pulling back the anchor delivery sheath 130 while generally maintaining the positions of the inner catheter 160 and/or the anchor delivery catheter 140. In some implementations, the expression of the anchor assembly 200 is caused by a combination of proximally pulling back the anchor delivery sheath 130 while distally extending the positions of the inner catheter 160 and/or the anchor delivery catheter 140.

As the anchor assembly 200 emerges from the confines of the anchor delivery sheath 130, the anchor assembly 200 may expand from a low-profile delivery configuration to an at least partially expanded configuration (as shown in FIG. 2). The extent of expansion of the anchor assembly 200 can be at least partially controlled by the relative positioning of the anchor delivery catheter 140 in relation to the inner catheter 160. For instance, as the anchor delivery catheter 140 is moved proximally in relation to the inner catheter 160, the anchor assembly 200 is axially elongated and radially contracted. Conversely, as the anchor delivery catheter 140 is moved distally in relation to the inner catheter 160, the anchor assembly 200 is axially shortened and radially expanded. In some implementations, this control of the radial size of the anchor assembly 200 is used by a clinician during the process of deploying the anchor assembly 200 within the native mitral valve 17, as described further below. As described further below, the one or more control wires 142 can also be used to control some radial expansion of the anchor assembly 200 (without changing the relative distance of the anchor delivery catheter 140 in relation to the inner catheter 160).

Figure 22:
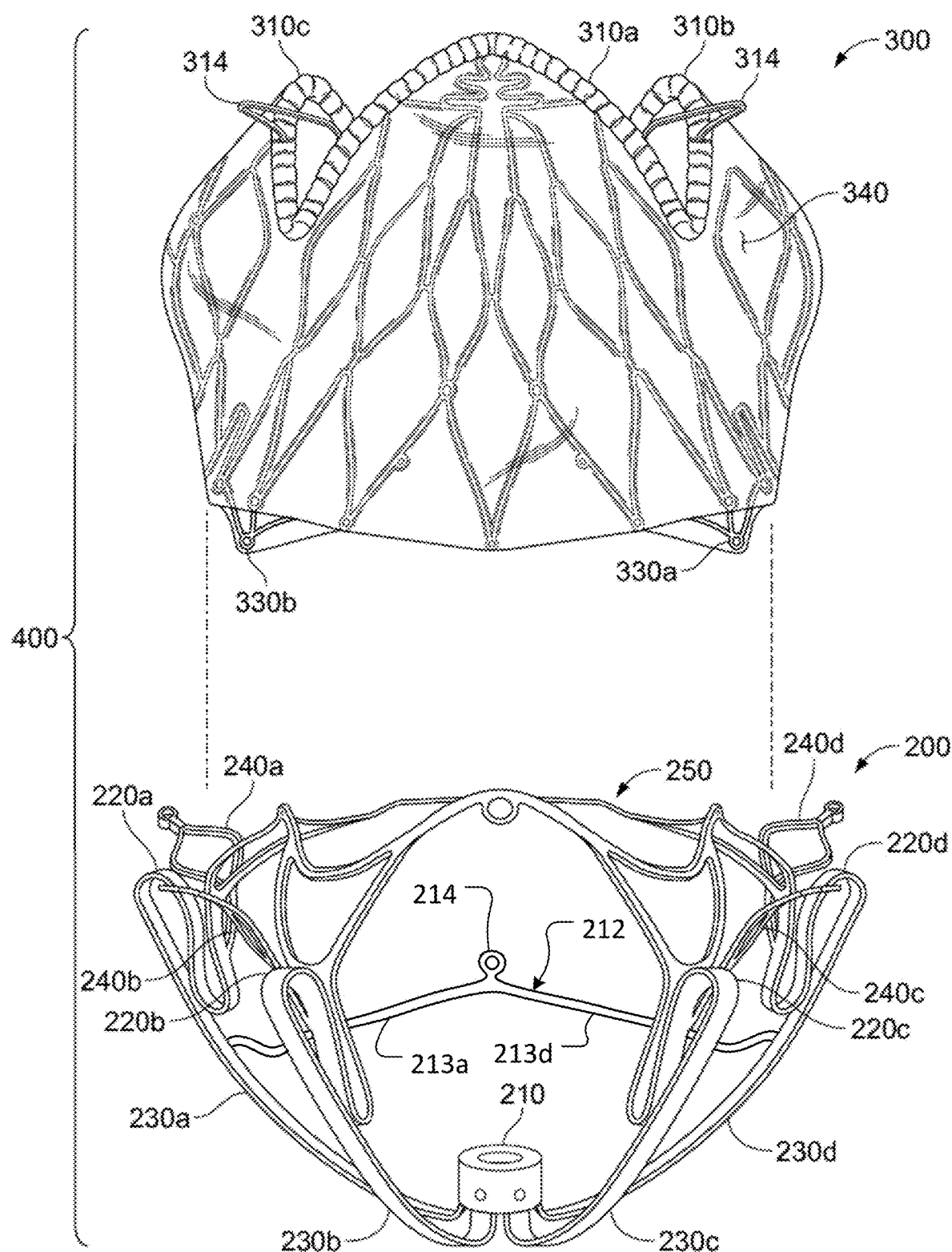
FIG. 22 is an exploded posterior side view of an anchor assembly and valve assembly of FIGS. 16-19, in accordance with some embodiments.

It should be understood that the prosthetic mitral valves provided herein are comprised of an anchor assembly 200 and a separate valve assembly (e.g., refer to FIG. 22). The anchor assembly 200 is deployed to an arrangement interfacing within the native mitral valve 17 prior to deployment of the valve assembly. Said differently, after implanting the anchor assembly 200 within the native mitral valve 17, the valve assembly can then be deployed within the anchor assembly 200 and within the native mitral valve 17 (as described further below). Therefore, it can be said that the prosthetic mitral valves provided herein are deployed using a staged implantation method. That is, the anchor assembly 200 is deployed in one stage, and the valve assembly is deployed in a subsequent stage. In some embodiments, as described further below, a SAM containment member is deployed as part of the deployment method. In some implementations, the deployment of the valve assembly takes place right after the deployment of the anchor assembly 200 (e.g., during the same medical procedure). In some implementations, the deployment of the valve assembly takes place hours, days, weeks, or even months after the deployment of the anchor assembly 200 (e.g., during a subsequent medical procedure).

The staged implantation method of the prosthetic mitral valves provided herein is facilitated by the fact that when the anchor assembly 200 itself is implanted within the native mitral valve 17, the native mitral valve 17 continues to function essentially as before the implantation of the anchor assembly 200 without a significant impact on cardiovascular physiology. That is the case because, as described further below, the anchor assembly 200 interfaces and anchors within structural aspects of the native mitral valve 17 without substantially interfering with the leaflets or chordae tendineae of the native mitral valve 17.

Still referring to FIG. 2, in the depicted arrangement the distal end portion of the secondary steerable catheter 150 is located at least partially internally within the anchor assembly 200. The secondary steerable catheter 150 can be manipulated by a clinician operator to reversibly bend (deflect) the distal end portion of the secondary steerable catheter 150. As the secondary steerable catheter 150 is bent by the clinician, other components of the delivery system 100 may deflect along with the secondary steerable catheter 150. For example, portions of one or more of the inner catheter 160 and the anchor delivery catheter 140 may bend in response to the bending of the deflectable catheter 150. Because the anchor assembly 200 is coupled to the inner catheter 160 and the anchor delivery catheter 140, the anchor assembly 200 can, in turn, be pivoted or "panned" by bending the secondary steerable catheter 150.

Figure 3:
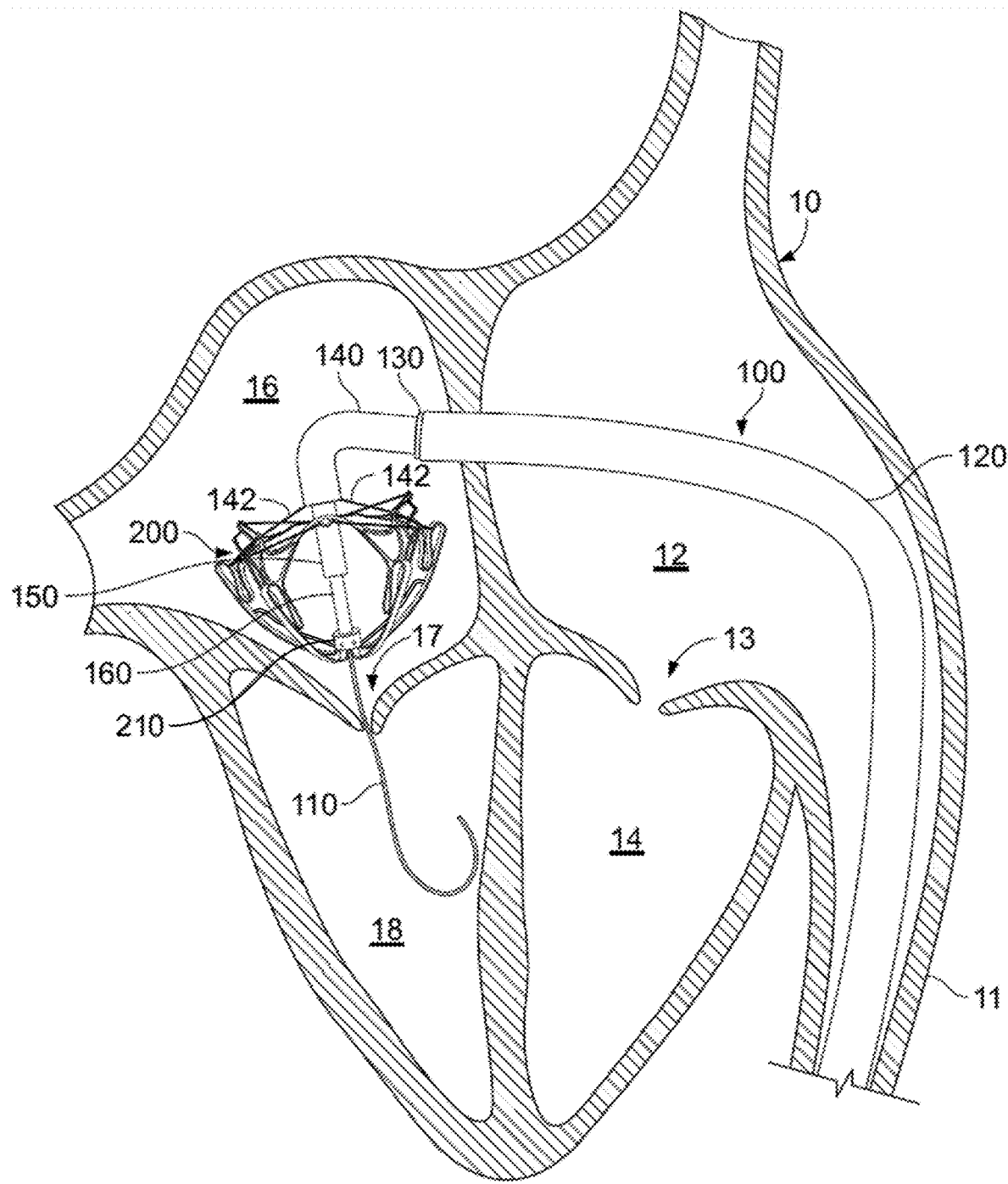
FIG. 3 shows a perspective view of the anchor assembly of FIG. 2 after being rotated/panned in the left atrium so as to orient the anchor assembly generally perpendicular to the native mitral valve.

Referring to FIG. 3, as described above, in some embodiments the secondary steerable catheter 150 can be articulated (also referred to as "steered," "deflected," "bent," "curved," and the like) to orient the anchor assembly 200 in relation to the mitral valve 17 as desired. That is, in some embodiments the secondary steerable catheter 150 has one or more deflection zones at a distal end portion of the secondary steerable catheter 150. For example, in the depicted embodiment the secondary steerable catheter 150 has two deflection zones 152 and 154 (refer to FIG. 5) at the distal end portion of the secondary steerable catheter 150. In some embodiments, the two deflection zones 152 and 154 allow for deflection of the distal end portion of the secondary steerable catheter 150 within two separate and distinct planes. For example, in the depicted embodiment deflection zone 152 allows for deflection of the distal end portion of the secondary steerable catheter 150 generally within the plane of FIGS. 1-4, while deflection zone 154 allows for deflection of the distal end portion of the secondary steerable catheter 150 generally orthogonal to the plane of FIGS. 1-4. In some implementations, a deployment frame system (such as the example deployment frame systems described below) is used to initiate and control such deflection of the secondary steerable catheter 150, including deflection of the distal end portion of the secondary steerable catheter 150 within two separate and distinct planes, individually.

In some implementations, it is desirable to orient (e.g., laterally pivot, pan, etc.) the anchor assembly 200 within the atrium 16 so that the longitudinal axis of the anchor assembly 200 is generally perpendicular to the native mitral valve 17, and coaxial with the native mitral valve 17 (e.g., to center the anchor assembly 200 with the line or coaptation of the mitral valve 17). The orienting of the partially or fully expanded anchor assembly 200 within the atrium 16 may be advantageous versus having to orient the anchor assembly 200 while it is still constrained within a delivery sheath, as the latter assembly is a relatively large and stiff catheter assembly.

In some implementations, the anchor assembly 200 within the atrium 16 can be additionally, or alternatively, oriented in relation to the native mitral valve 17 by rotating the guide catheter 120 about its longitudinal axis. Such a rotation of the guide catheter 120 about its longitudinal axis can result in a directional adjustment of the longitudinal axis of the distal tip portion of the guide catheter 120. That is, rotation of the guide catheter 120 about its longitudinal axis can result in pointing the distal tip portion of the guide catheter 120 (and the components of the delivery system 100) in a desired direction within the atrium 16. In some implementations, a deployment frame system (such as the example deployment frame systems described below) is used to initiate and control such rotation of the guide catheter 120 about its longitudinal axis.

In some implementations, the relative rotational alignment of the anchor assembly 200 in relation to the mitral valve 17 can be adjusted as desired in preparation for engaging the anchor assembly 200 with the native mitral valve 17. For example, in some implementations the anchor assembly 200 can be rotated about its longitudinal axis by rotating the inner catheter 160 and the anchor delivery catheter 140 generally in unison, while keeping the secondary steerable catheter 150 essentially stationary. In some implementations, a deployment frame system (such as the example deployment frame systems described below) is used to initiate and control such rotation of the anchor assembly 200 about its longitudinal axis.

In preparation for engaging the anchor assembly 200 with the native mitral valve 17, the clinician operator may manipulate the radial size of the anchor frame 200 so that the anchor frame 200 can be passed through the native mitral valve 17 without damaging the native mitral valve 17. For example, the clinician can move the anchor delivery catheter 140 proximally in relation to the inner catheter 160 to radially contract the anchor assembly 200. Alternatively, or additionally, the clinician can diametrically expand or retract one or more portions of the anchor assembly 200 by manipulation of the one or more control wires 142. With the anchor assembly 200 radially contracted in a desired orientation, and appropriately aligned with the mitral valve 17, the anchor frame 200 can be safely passed through the native mitral valve 17 without damaging the native mitral valve 17 and/or entangling chordae tendineae of the mitral valve 17.

Figure 4:
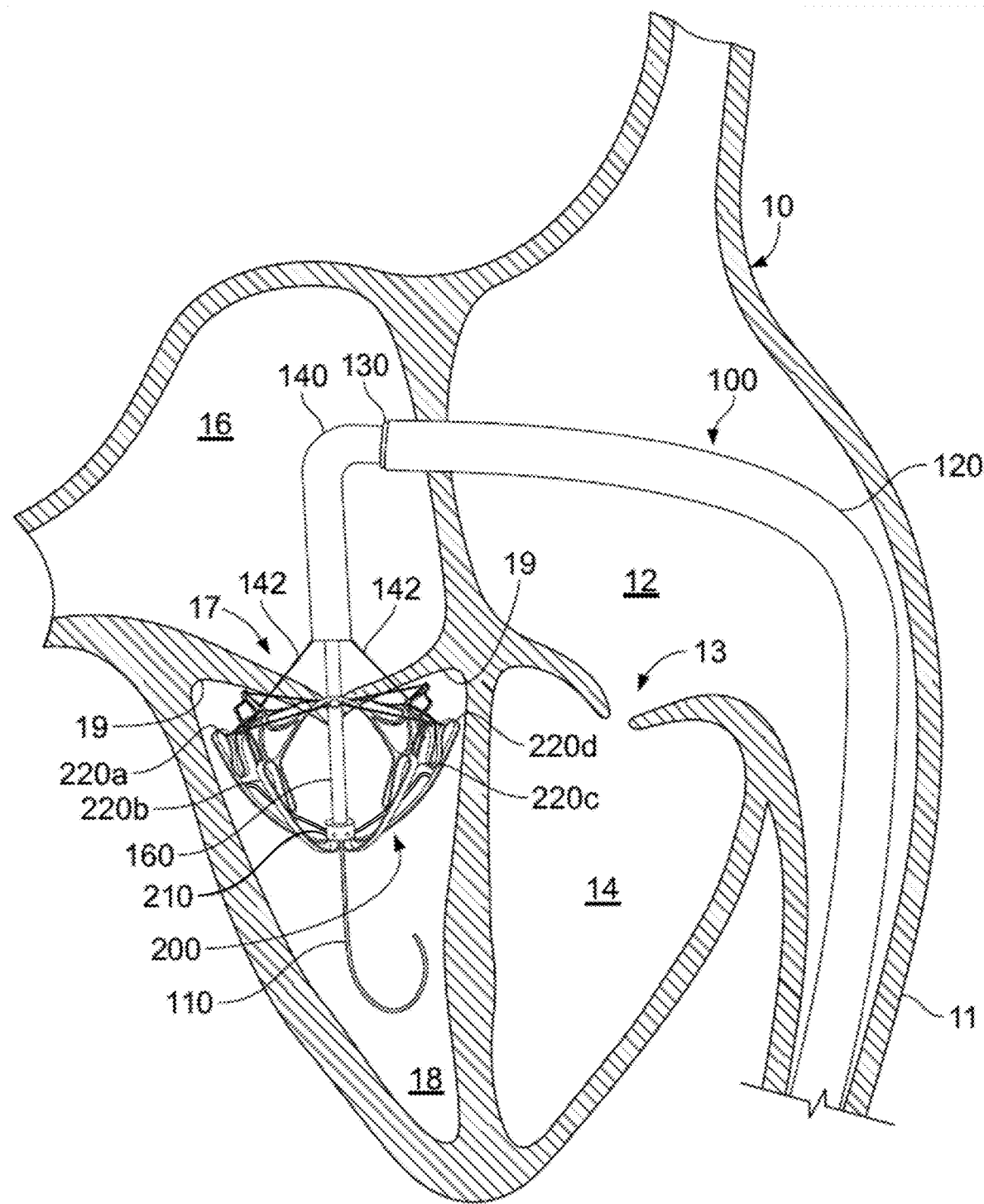
FIG. 4 shows a perspective view of the anchor assembly of FIG. 3 after being partially advanced through the native mitral valve so as to position projections of the anchor assembly below a sub-annular gutter of the native mitral valve.

Referring to FIG. 4, while the secondary steerable catheter 150 is retained in its bent (deflected) configuration as described in reference to FIG. 3, the inner catheter 160 and the anchor delivery catheter 140 can be simultaneously advanced. Because the inner catheter 160 is releasably coupled to the hub 210 of the anchor assembly 200, and because the anchor delivery catheter 140 is releasably coupled to at least the proximal end of the anchor assembly 200 via the one or more control wires 142, generally simultaneous advancement of the inner catheter 160 and the anchor delivery catheter 140 results in advancement of the anchor assembly 200. The anchor assembly 200 is advanced such that the distal end of anchor assembly 200 is within the left ventricle 18 while the proximal end of the anchor assembly 200 is within the left atrium 16. Hence, some portions of the anchor assembly 200 are on each side of the native mitral valve 17. As described further below, simultaneous movement of two or more components of the delivery system 100 (e.g., the inner catheter 160 in conjunction with the anchor delivery catheter 140) can be initiated and controlled using a deployment frame system (such as the example deployment frame systems described below) in some implementations.

In the depicted embodiment, the anchor assembly 200 includes four anchor feet: a lateral anterior foot 220a, a lateral posterior foot 220b, a medial posterior foot 220c, and a medial anterior foot 220d. In some embodiments, fewer or more anchor feet may be included (e.g., two, three, five, six, or more than six). In some embodiments, the anchor feet 220a, 220b, 220c, and 220d are portions of the anchor assembly 200 that are configured for contact with a sub-annular gutter 19 of the native mitral valve 17, without penetrating tissue of the native mitral valve 17. Accordingly, the anchor feet 220a, 220b, 220c, and 220d have atraumatic surfaces that are generally comparable to feet. However, in some embodiments one or more of the anchor feet 220a, 220b, 220c, and 220d are configured to penetrate tissue and may have anchor features such as barbs, coils, hooks, and the like.

In the arrangement of FIG. 4, the anchor feet 220a, 220b, 220c, and 220d are positioned below the sub-annular gutter 19. In this arrangement, the radial size of the anchor assembly 200 can be increased to align the anchor feet 220a, 220b, 220c, and 220d with the sub-annular gutter 19. For example, in some embodiments the clinician can move the anchor delivery catheter 140 distally in relation to the inner catheter 160 to radially expand the anchor assembly 200 to align the anchor feet 220a, 220b, 220c, and 220d with the sub-annular gutter 19. Alternatively, or additionally, in some embodiments a mid-body control wire 142 positioned on or around a mid-body portion of the anchor assembly 200 can be manipulated (e.g., slackened) to allow radial self-expansion of the anchor assembly 200, to align the anchor feet 220a, 220b, 220c, and 220d with the sub-annular gutter 19. Such alignment can be performed in preparation for seating the anchor feet 220a, 220b, 220c, and 220d within the sub-annular gutter 19.

Figure 5:
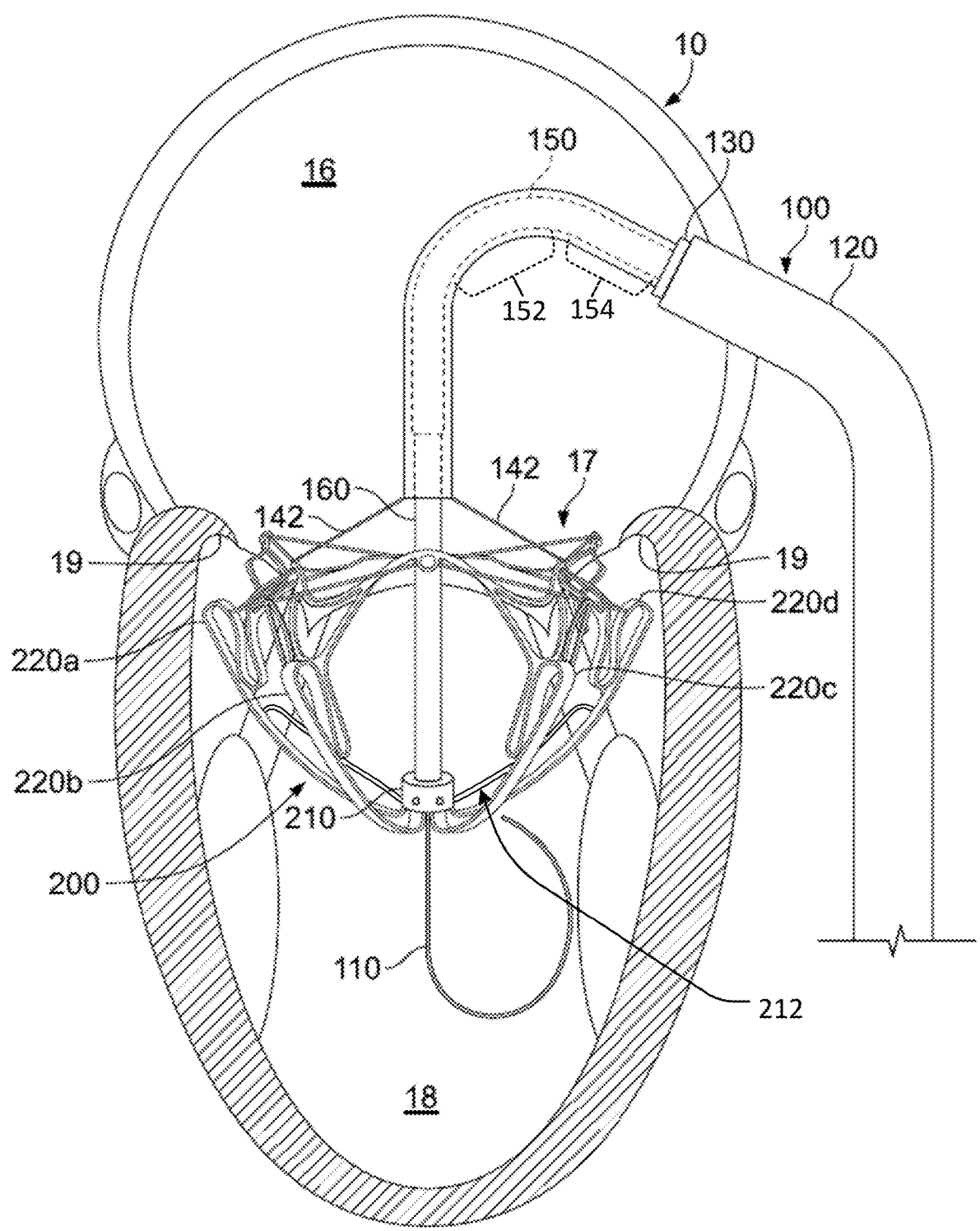
FIG. 5 shows a perspective view of the anchor assembly in a similar arrangement as shown in FIG. 4, but in a commissural cross-sectional view of the heart (from the left side of the heart).

Referring to FIG. 5, a commissural cross-sectional view of the heart 10 provides another perspective of the anchor assembly 200 in the same arrangement in relation to the native mitral valve 17 as shown in FIG. 4. This commissural cross-sectional view of the heart 10 is a cross-sectional view taken through the mitral valve 17 along a plane through the left atrium 16 and left ventricle 18 that is parallel to the line that intersects the two commissures of the mitral valve 17 (as described further in reference to FIG. 8 below). In the following FIGS. 5-7 and 15-19, the commissural cross-sectional view of the heart 10 will be used to describe the delivery system 100 and methods for deploying the prosthetic mitral valves provided herein. The view in FIGS. 5-7 and 15-19 is slightly tilted so that better visualization of the anchor assembly 200 is provided.

The anchor feet 220a, 220b, 220c, and 220d are positioned below the sub-annular gutter 19. In this position, the anchor feet 220a, 220b, 220c, and 220d are positioned under the systolic and diastolic excursions of the leaflets of the native mitral valve 17. In this orientation, the anchor feet 220a, 220b, 220c, and 220d can be aligned with the sub-annular gutter 19 in preparation for seating the anchor feet 220a, 220b, 220c, and 220d within the sub-annular gutter 19.

In this figure, portions of an example SAM containment member 212 are in view. In the depicted embodiment, the SAM containment member 212 extends from the anchor assembly 200. For example, the SAM containment member 212 comprises an elongate member with a first end that extends from a first portion of the anchor assembly 200 and a second end that extends from a second portion of the anchor assembly 200. In particular embodiments, the SAM containment member 212 is integrally formed as part of the anchor assembly 200. In specific embodiments, the SAM containment member 212, or portions thereof, may be formed separately from the anchor assembly 200 and thereafter attached to the anchor assembly 200.

The SAM containment member 212 can be arranged in a pre-deployed configuration as shown. As described further below, the SAM containment member 212 can be reconfigured to a deployed configuration such that the SAM containment member 212 physically prevents an anterior leaflet of a native mitral valve from obstructing the LVOT. In some embodiments, the SAM containment member 212 is biased to self-reconfigure to the deployed configuration when the SAM containment member 212 is unconstrained. While one particular embodiment of the SAM containment member 212 is depicted, it should be understood that multiple SAM containment member embodiments are envisioned and within the scope of this disclosure.

Figure 6:
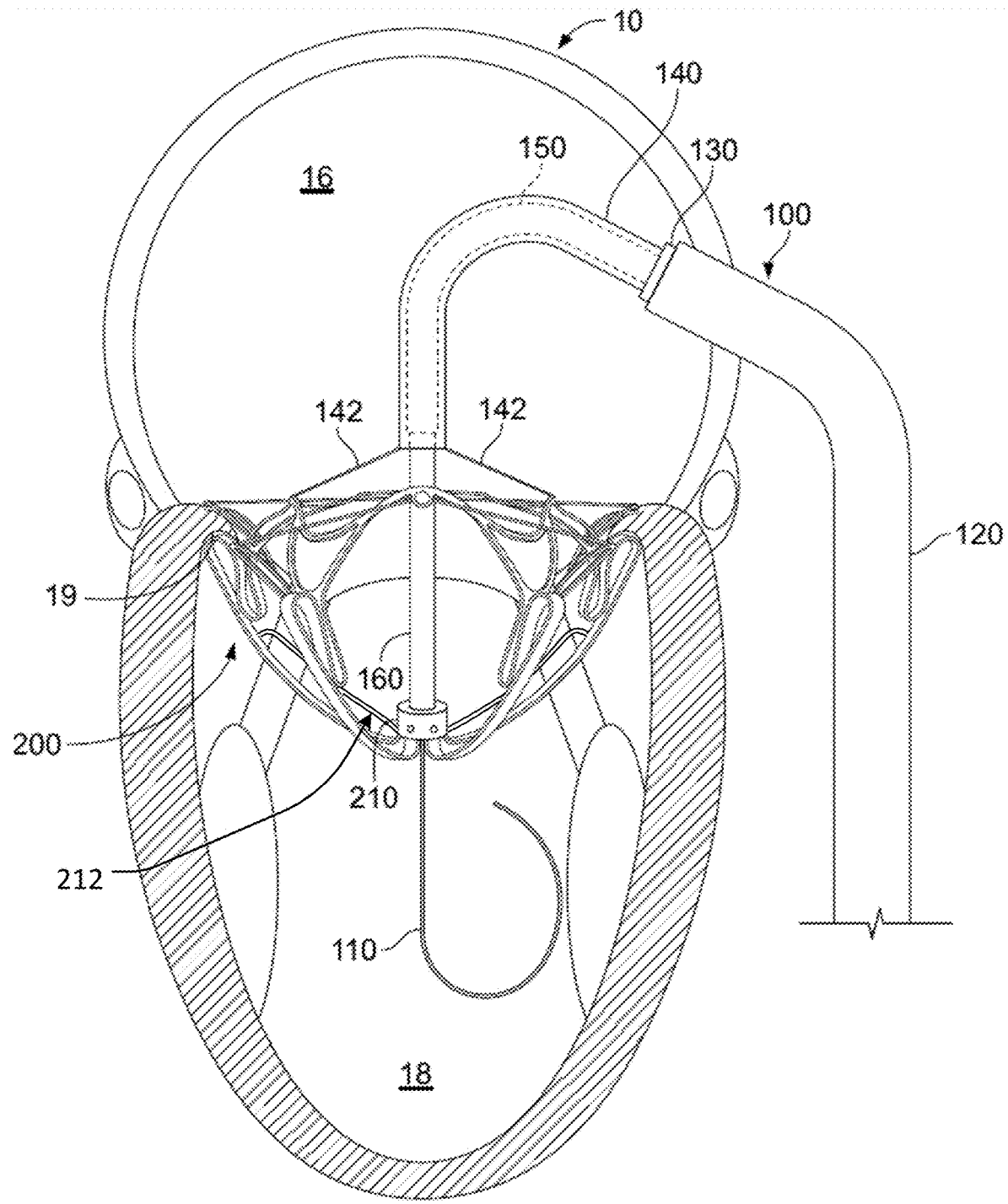
FIG. 6 shows a perspective view of the anchor assembly of FIG. 5 after being retracted so as to position the projections of the anchor assembly in the sub-annular gutter of the native mitral valve.

Referring to FIG. 6, the inner catheter 160 and the anchor delivery catheter 140 can be simultaneously retracted while maintaining the secondary steerable catheter 150 and the guide catheter 120 in fixed positions. As a result, the anchor feet 220a, 220b, 220c, and 220d become seated in the sub-annular gutter 19. As described further below, simultaneous movement of two or more components of the delivery system 100 (e.g., the inner catheter 160 in conjunction with the anchor delivery catheter 140, while maintaining the secondary steerable catheter 150 and the guide catheter 120 in fixed positions) can be initiated and controlled using a deployment frame system (such as the example deployment frame systems described below) in some implementations.

With the anchor feet 220a, 220b, 220c, and 220d seated in the sub-annular gutter 19, the anchor feet 220a, 220b, 220c, and 220d are positioned under the systolic and diastolic excursions of the leaflets of the native mitral valve 17, and the other structures of the anchor assembly 200 do not inhibit the movements of the leaflets. Therefore, with the anchor assembly 200 coupled to the structures of the mitral valve 17 as described, the mitral valve 17 can continue to function as it did before the placement of the anchor assembly 200. In addition, the manner in which the anchor assembly 200 interfaces with the native mitral valve 17 does not result in deformation of the native mitral valve 17. With the SAM containment member 212 in its pre-deployed configuration, the SAM containment member 212 does not affect the natural function of the native mitral valve 17. Therefore, the native mitral valve 17 can continue to function as it did before the placement of the anchor assembly 200.

Figure 7:
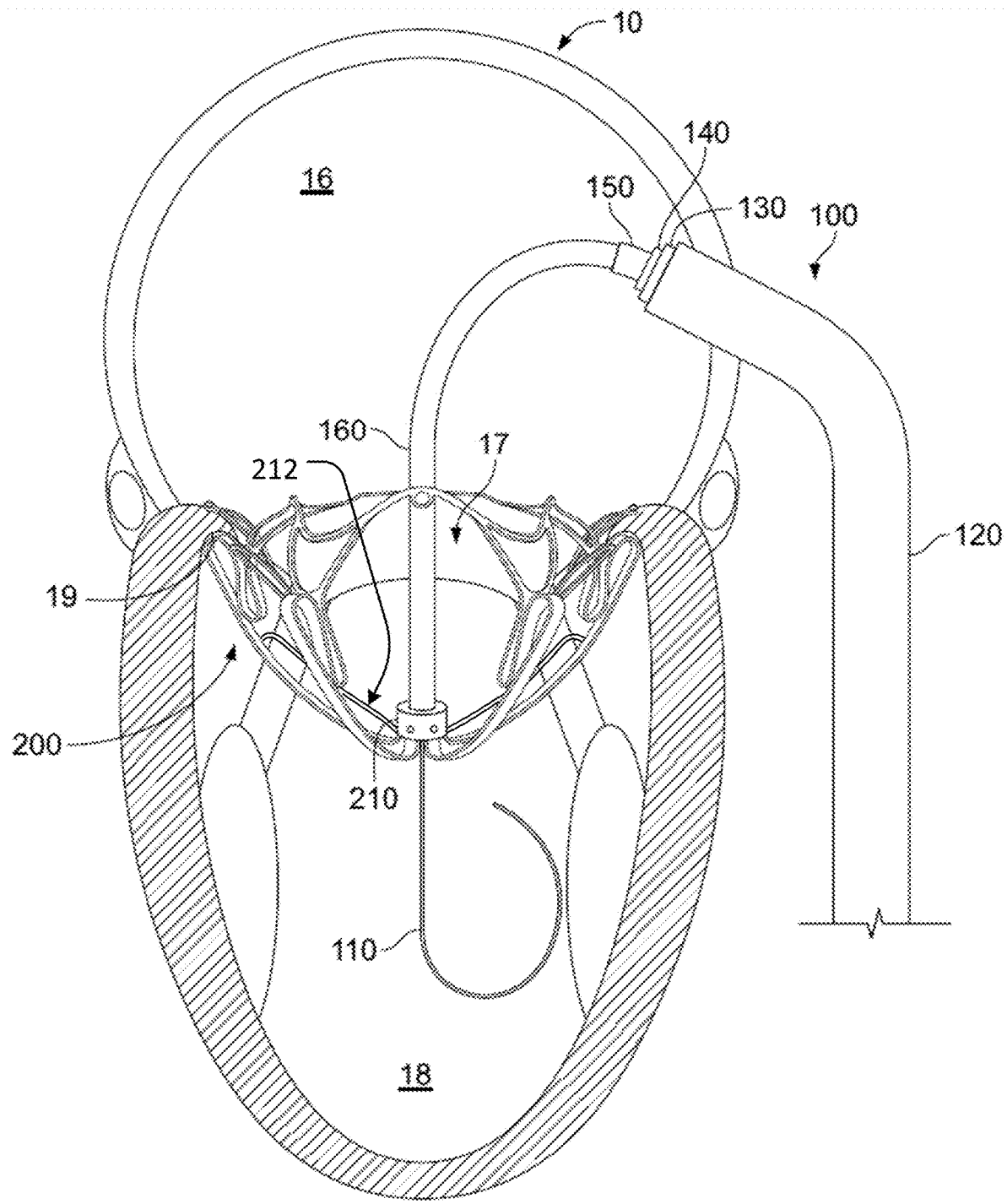
FIG. 7 shows a perspective view of the anchor assembly of FIG. 6 after the retraction of some members of the deployment system.

Referring to FIG. 7, with the anchor assembly 200 engaged within the native mitral valve 17, components of the delivery system 100 can be withdrawn from the anchor assembly 200. For example, the one or more control wires 142 can be detached from the anchor assembly 200 (e.g., from the mid-body and proximal end portions of the anchor assembly 200 in some embodiments). When the control wire 142 is detached from a proximal end portion of the anchor assembly, in some embodiments atrial holding features 240a, 240b, 240c, and 240d (refer to FIGS. 9-11) self-deploy to respective positions directly adjacent to, or spaced apart just above, the annulus of the mitral valve 17.

With the anchor assembly 200 deployed within the mitral valve 17 (as described above), the anchor delivery catheter 140 can be withdrawn, the secondary steerable catheter 150 can be withdrawn, and the anchor delivery sheath 130 can also be withdrawn. In fact, if so desired, the anchor delivery catheter 140, the secondary steerable catheter 150, and the anchor delivery sheath 130 can be completely withdrawn from the guide catheter 120. In contrast, in some implementations the inner catheter 160 is advantageously left attached to the hub 210 of the anchor assembly 200 (and left attached to the SAM containment member 212 in some implementations). As will be described further below, in some implementations the inner catheter 160 can be used as a rail on which a valve assembly is later deployed into the interior of the anchor assembly 200. However, in some implementations the anchor assembly 200 is completely detached from the delivery system 100, and the delivery system 100 is removed from the patient. After a period of minutes, hours, days, weeks, or months, subsequent to the deployment of the anchor assembly 200, a valve assembly can be installed into the anchor assembly 200 to complete the installation of the prosthetic mitral valve.

In some implementations, withdrawal of the anchor delivery catheter 140, the secondary steerable catheter 150, and the anchor delivery sheath 130 can be performed as follows. First, the anchor delivery catheter 140 can be withdrawn into the anchor delivery sheath 130. Then, the secondary steerable catheter 150 can be withdrawn into the anchor delivery sheath 130 while generally simultaneously undeflecting (relaxing) the bend(s) in the secondary steerable catheter 150. Thereafter, in some embodiments the anchor delivery catheter 140, the secondary steerable catheter 150, and the anchor delivery sheath 130 can be simultaneously withdrawn further, including up to completely from the guide catheter 120. As described further below, such individual and/or simultaneous movements of components of the delivery system 100 can be initiated and controlled using a deployment frame system (such as the example deployment frame systems described below) in some implementations.

In the depicted implementation, the SAM containment member 212 is still restrained in its pre-deployed configuration. As described further below, in some embodiments the depicted embodiment of the SAM containment member 212 is deployed after the installation of a valve assembly into the anchor assembly 200. Alternatively, as described further below, in some embodiments of the SAM containment member 212, the SAM containment member 212 is deployed prior to the installation of a valve assembly into the anchor assembly 200.

Figure 8:
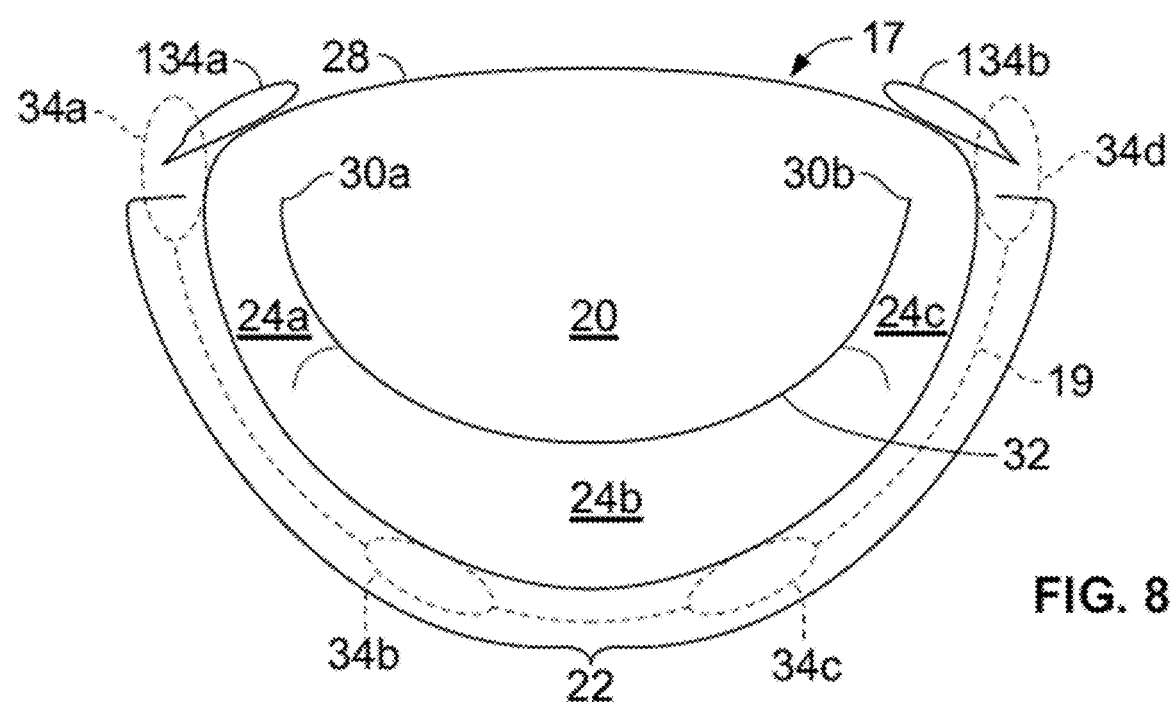
FIG. 8 is a top view of a native mitral valve and depicts a gutter perimeter of the sub-annular gutter of FIG. 7 (without the anchor assembly).

Referring to FIG. 8, the anatomy of the native mitral valve 17 includes some consistent and predictable structural features across patients that can be utilized for engaging the anchor assembly 200 therewith. For example, the native mitral valve 17 includes the aforementioned sub-annular gutter 19. In addition, the native mitral valve 17 includes a D-shaped annulus 28, an anterolateral commissure 30a, a posteromedial commissure 30b, a left fibrous trigone 134a, and a right fibrous trigone 134b. Further, the native mitral valve 17 includes an anterior leaflet 20 and a three-part posterior leaflet 22. The posterior leaflet 22 includes a lateral scallop 24a, a middle scallop 24b, and a medial scallop 24c. The free edges of the posterior leaflet 22 and the anterior leaflet 20 meet along a coaptation line 32.

The D-shaped annulus 28 defines the structure from which the anterior leaflet 20 and posterior leaflet 22 extend and articulate. The left and right fibrous trigones 134a and 134b are located near the left and right ends of the anterior leaflet 20 and generally adjacent the lateral and medial scallops 24a and 24c of the posterior leaflet 22. The sub-annular gutter 19 runs along the annulus 28 between the left and right fibrous trigones 134a and 134b along the posterior leaflet 22.

The regions at or near the high collagen annular trigones 134a and 134b can generally be relied upon to provide strong, stable anchoring locations. The muscle tissue in the regions at or near the trigones 134a and 134b also provides a good tissue ingrowth substrate for added stability and migration resistance of the anchor assembly 200. Therefore, the regions at or near the trigones 134a and 134b define a left anterior anchor zone 34a and a right anterior anchor zone 34b respectively. The left anterior anchor zone 34a and the right anterior anchor zone 34b provide advantageous target locations for placement of the lateral anterior foot 220a and the medial anterior foot 220d respectively.

Figure 9:
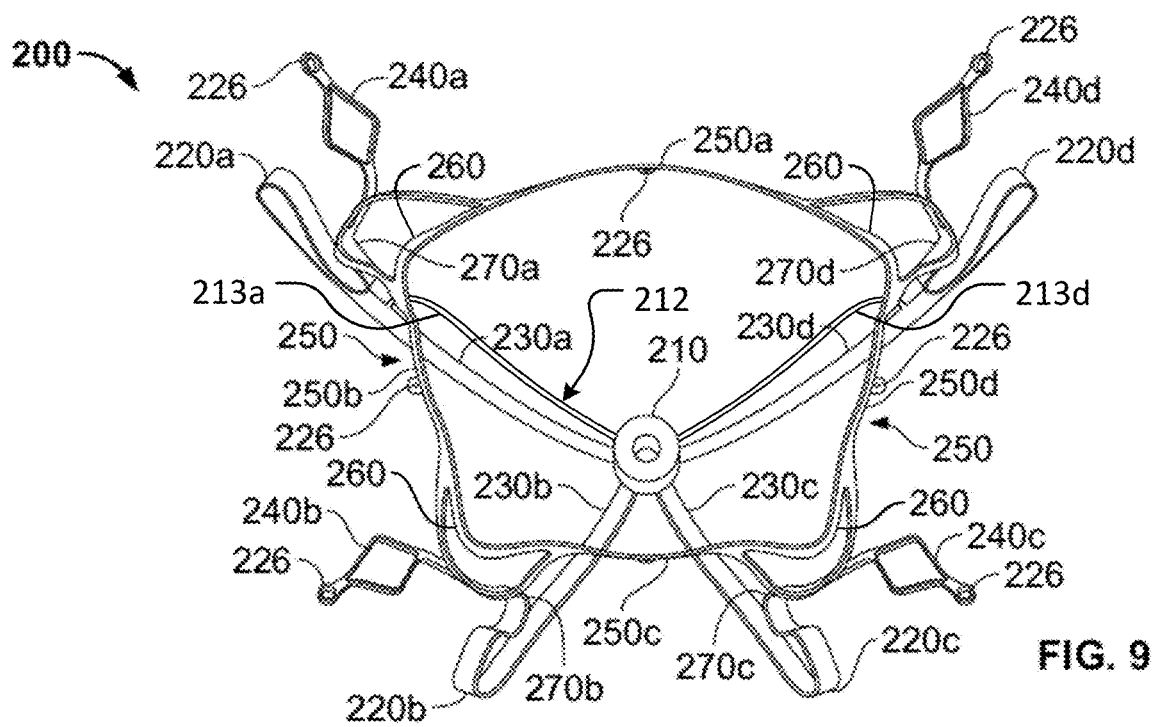
FIG. 9 shows a perspective top view of an example anchor assembly of FIGS. 2-7, including an example SAM containment member in a pre-deployed configuration, in accordance with some embodiments.

Referring also to FIG. 9, the depicted embodiment of the anchor assembly 200 also includes the lateral posterior foot 220b and the medial posterior foot 220c. As previously described, the lateral posterior foot 220b and the medial posterior foot 220c can also be advantageously positioned in the sub-annular gutter 19 in order to provide balanced and atraumatic coupling of the anchor assembly 200 to the native mitral valve 17. Therefore, a left posterior anchor zone 34b and a right anterior anchor zone 34c are defined in the sub-annular gutter 19. The left posterior anchor zone 34b and the right anterior anchor zone 34c can receive the lateral posterior foot 220b and the medial posterior foot 220c respectively. In some implementations, the locations of the left posterior anchor zone 34b and the right anterior anchor zone 34c may vary from the depicted locations while still remaining within the sub-annular gutter 19. It should be understood that the depicted anchor assembly 200 is merely one non-limiting example of the anchor assemblies provided within the scope of this disclosure.

In some embodiments, the anchor assembly 200 includes supra-annular structures and sub-annular structures. For example, the sub-annular structures of the anchor assembly 200 include the aforementioned anchor feet 220a, 220b, 220c, and 220d, the SAM containment member 212, and the hub 210. In some embodiments, as described above, the hub 210 functions as a connection structure for the delivery system 100 (e.g., refer to FIG. 2). In addition, the hub 210 can function as a stabilizing structural component from which a lateral anterior sub-annular support arm 230a, a lateral posterior sub-annular support arm 230b, a medial posterior sub-annular support arm 230c, and a medial anterior sub-annular support arm 230d extend to the anchor feet 220a, 220b, 220c, and 220d respectively.

In the depicted embodiment, the SAM containment member 212 includes a lateral anterior arm 213a and a medial anterior arm 213d. The lateral anterior arm 213a extends from the lateral anterior sub-annular support arm 230a. The medial anterior arm 213d extends from the medial anterior sub-annular support arm 230d. In some embodiments, portions of the SAM containment member 212 may extend from other areas on the anchor assembly 200.

In some embodiments, such as the depicted embodiment, the supra-annular structures of the anchor assembly 200 include: a lateral anterior atrial holding feature 240a, a lateral posterior atrial holding feature 240b, a medial posterior atrial holding feature 240c, and a medial anterior atrial holding feature 240d; an anterior anchor arch 250a, a left anchor arch 250b, a posterior anchor arch 250c, and a right anchor arch 250d; and connection bridges 260. The anterior anchor arch 250a, left anchor arch 250b, posterior anchor arch 250c, and right anchor arch 250d are joined with each other to form an undulating supra-annular ring 250 that acts as a supra-annular structural element for the anchor assembly 200. As will be described further below, the supra-annular ring 250 also defines an opening to a space within the interior of the anchor assembly 200 that is configured to receive and engage with a valve assembly. The atrial holding features 240a, 240b, 240c, and 240d are configured to contact the shelf-like supra-annular tissue surface above the mitral valve annulus, and to thereby stabilize the anchor assembly 200 in supra-annular areas that are generally opposite of the anchor feet 220a, 220b, 220c, and 220d respectively.

In some embodiments, connection bridges 260 provide enhanced stability and fatigue resistance from vertically oriented forces on a companion artificial valve assembly when the valve (not shown) is closed and blocking pressurized blood during systole. The anchor assembly 200 can also include one or more eyelets 226 in frame portions adjacent the arches, which are additional control points for delivery and retrieval of the assembly, or could be used to secure a positional delivery frame.

In some embodiments, such as the depicted embodiment, the supra-annular structures and sub-annular structures of the anchor assembly 200 are interconnected by a lateral anterior inter-annular connection 270a, a lateral posterior inter-annular connection 270b, a medial posterior inter-annular connection 270c, and a medial anterior inter-annular connection 270d. For example, the lateral anterior inter-annular connection 270a connects the lateral anterior anchor foot 220a with the lateral anterior atrial holding feature 240a. In addition, the lateral anterior inter-annular connection 270a connects the lateral anterior anchor foot 220a with the anterior anchor arch 250a and the left anchor arch 250b. In the depicted embodiment, each of the other inter-annular connections 270b, 270c, and 270d interconnect portions of the supra-annular structures and sub-annular structures in manners analogous to that of the lateral anterior inter-annular connection 270a. For example, the lateral anterior inter-annular connection 270b connects the lateral anterior anchor foot 220b with the left anchor arch 250b and the posterior anchor arch 250c; the lateral anterior inter-annular connection 270c connects the lateral anterior anchor foot 220c with the posterior anchor arch 250c and the right anchor arch 250d; and the lateral anterior inter-annular connection 270d connects the lateral anterior anchor foot 220d with the right anchor arch 250d and the anterior anchor arch 250a.

In some embodiments, the elongate members of the anchor assembly 200, including SAM containment member 212, are formed from a single piece of precursor material (e.g., sheet or tube) that is cut, expanded, and connected to the hub 210. For example, some embodiments are fabricated from a tube that is laser-cut (or machined, chemically etched, water-jet cut, etc.) and then expanded and heat-set into its final expanded size and shape. In some embodiments, the anchor assembly 200, including SAM containment member 212, is created compositely from multiple elongate members (e.g., wires or cut members) that are joined together with the hub 210 and each other to form the anchor assembly 200.

The elongate members of the anchor assembly 200 can be comprised of various materials and combinations of materials. In some embodiments, nitinol (NiTi) is used as the material of the elongate members of the anchor assembly 200, but other materials such as stainless steel, L605 steel, polymers, MP35N steel, stainless steels, titanium, cobalt/chromium alloy, polymeric materials, Pyhnox, Elgiloy, or any other appropriate biocompatible material, and combinations thereof can be used. The super-elastic properties of NiTi make it a particularly good candidate material for the elongate members of the anchor assembly 200 because, for example, NiTi can be heat-set into a desired shape. That is, NiTi can be heat-set so that the anchor assembly 200 tends to self-expand into a desired shape when the anchor assembly 200 is unconstrained, such as when the anchor assembly 200 is deployed out from the anchor delivery sheath 130. A anchor assembly 200 made of NiTi, for example, may have a spring nature that allows the anchor assembly 200 to be elastically collapsed or "crushed" to a low-profile delivery configuration and then to reconfigure to the expanded configuration as shown in FIG. 9. The anchor assembly 200 may be generally conformable, fatigue resistant, and elastic such that the anchor assembly 200 can conform to the topography of the surrounding tissue when the anchor assembly 200 is deployed in a native mitral valve of a patient.

In some embodiments, the diameter or width/thickness of one or more of the elongate members forming the anchor assembly 200 may be within a range of about 0.008" to about 0.015" (about 0.20 mm to about 0.40 mm), or about 0.009" to about 0.030" (about 0.23 mm to about 0.76 mm), or about 0.01" to about 0.06" (about 0.25 mm to about 1.52 mm), or about 0.02" to about 0.10" (about 0.51 mm to about 2.54 mm), or about 0.06" to about 0.20" (about 1.52 mm to about 5.08 mm). In some embodiments, the elongate members forming the anchor assembly 200 may have smaller or larger diameters or widths/thicknesses. In some embodiments, each of the elongate members forming the anchor assembly 200 has essentially the same diameter or width/thickness. In some embodiments, one or more of the elongate members forming the anchor assembly 200 has a different diameter or width/thickness than one or more of the other elongate members of the anchor assembly 200. In some embodiments, one or more portions of one or more of the elongate members forming the anchor assembly 200 may be tapered, widened, narrowed, curved, radiused, wavy, spiraled, angled, and/or otherwise non-linear and/or not consistent along the entire length of the elongate members of the anchor assembly 200. Such features and techniques can also be incorporated with the valve assemblies of the prosthetic mitral valves provided herein.

In some embodiments, the elongate members forming the anchor assembly 200 may vary in diameter, thickness and/or width so as to facilitate variations in the forces that are exerted by the anchor assembly 200 in specific regions thereof, to increase or decrease the flexibility of the anchor assembly 200 in certain regions, to enhance migration resistance, and/or to control the process of compression (crushability) in preparation for deployment and the process of expansion during deployment of the anchor assembly 200.

In some embodiments, one or more of the elongate members of the elongate members forming the anchor assembly 200 may have a circular cross-section. In some embodiments, one or more of the elongate members forming the anchor assembly 200 may have a rectangular cross-sectional shape, or another cross-sectional shape that is not rectangular. Examples of cross-sectional shapes that the elongate members forming the anchor assembly 200 may have include circular, C-shaped, square, ovular, rectangular, elliptical, triangular, D-shaped, trapezoidal, including irregular cross-sectional shapes formed by a braided or stranded construct, and the like. In some embodiments, one or more of the elongate members forming the anchor assembly 200 may be essentially flat (i.e., such that the width to thickness ratio is about 2:1, about 3:1, about 4:1, about 5:1, or greater than about 5:1). In some examples, one or more of the elongate members forming the anchor assembly 200 may be formed using a center-less grind technique, such that the diameter of the elongate members varies along the length of the elongate members.

The anchor assembly 200 may include features that are directed to enhancing one or more desirable functional performance characteristics of the prosthetic mitral valve devices. For example, some features of the anchor assembly 200 may be directed to enhancing the conformability of the prosthetic mitral valve devices. Such features may facilitate improved performance of the prosthetic mitral valve devices by allowing the devices to conform to irregular tissue topographies and/or dynamically variable tissue topographies, for example. Such conformability characteristics can be advantageous for providing effective and durable performance of the prosthetic mitral valve devices. In some embodiments of the anchor assembly 200, some portions of the anchor assembly 200 are designed to be more conformable than other portions of the same anchor assembly 200. That is, the conformability of a single anchor assembly 200 can be designed to be different at various areas of the anchor assembly 200.

In some embodiments, the anchor assembly 200 includes features for enhanced in vivo radiographic visibility. In some embodiments, portions of the anchor assembly 200, such as one or more of the anchor feet 220a, 220b, 220c, and 220d, and/or SAM containment member 212, may have one or more radiopaque markers attached thereto. In some embodiments, some or all portions of the anchor assembly 200 are coated (e.g., sputter coated) with a radiopaque coating.

Still referring to FIGS. 8 and 9, as described above the anchor feet 220a, 220b, 220c, and 220d are sized and shaped to engage the sub-annular gutter 19 of the mitral valve 17. In some embodiments, the anterior feet 220a and 220d are spaced apart from each other by a distance in a range of about 30 mm to about 45 mm, or about 20 mm to about 35 mm, or about 40 mm to about 55 mm. In some embodiments, the posterior feet 220b and 220c are spaced apart from each other by a distance in a range of about 20 mm to about 30 mm, or about 10 mm to about 25 mm, or about 25 mm to about 40 mm.

In some embodiments, the anchor feet 220a, 220b, 220c, and 220d have a height ranging from about 8 mm to about 12 mm, or more than about 12 mm. In some embodiments, the anchor feet 220a, 220b, 220c, and 220d have a gutter engaging surface area (when fabric covered) ranging from about 6 mm$^2$ to about 24 mm$^2$. In some embodiments, the anchor feet 220a, 220b, 220c, and 220d each have essentially the same gutter engaging surface area. In particular embodiments, one or more of the anchor feet 220a, 220b, 220c, and 220d has a different gutter engaging surface area than one or more of the other anchor feet 220a, 220b, 220c, and 220d. The anchor feet 220a, 220b, 220c, and 220d can have widths ranging within about 1.5 mm to about 4.0 mm or more, and lengths ranging within about 3 mm to about 6 mm or more. The anchor feet 220a, 220b, 220c, and 220d are sized and shaped so that the anchor assembly 200 does not significantly impair the natural function of mitral valve chordae tendineae, the native mitral valve leaflets, and papillary muscles even after the anchor assembly is anchored at the mitral valve site.

As described previously, the anchor assembly 200 is designed to avoid interference with the functioning of the native mitral valve 17. Therefore, the anchor assembly 200 can be implanted within the native mitral valve 17 some time prior to the deployment therein of a replacement valve assembly, without degradation of valve 17 function during the period of time between the anchor implantation and the valve implantation (whether that time is on the order of minutes, or even several days or months). To avoid such interference between the anchor assembly 200 and the native mitral valve 17, the inter-annular connections 270a, 270b, 270c, and 270d pass through the coaptation line 32 approximately. More particularly, the lateral anterior inter-annular connection 270a passes through the coaptation line 32 adjacent to the anterolateral commissure 30a. In like manner, the medial anterior inter-annular connection 270d passes through the coaptation line 32 adjacent to the posteromedial commissure 30b. In some implementations, the lateral posterior inter-annular connection 270b and medial posterior inter-annular connection 270c pass through the native mitral valve 17 in locations that are posteriorly biased from the natural coaptation line 32. The posterior leaflet 22 will tend to compliantly wrap around the lateral posterior inter-annular connection 270b and medial posterior inter-annular connection 270c to facilitate sealing of the mitral valve 17, with the anchor assembly 200 coupled thereto.

Figure 10:
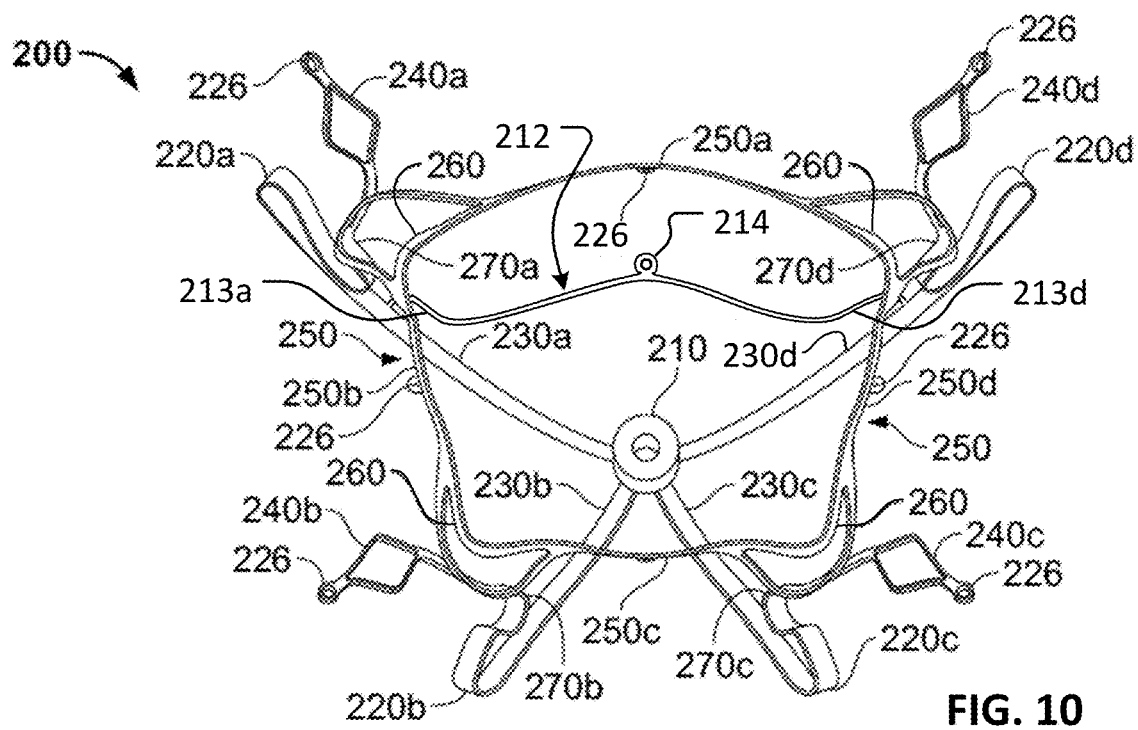
FIG. 10 shows a perspective top view of the example anchor assembly of FIG. 9, with the SAM containment member is a deployed configuration, in accordance with some embodiments.

In reference to FIGS. 9 and 10, the pre-deployed and deployed configurations of the SAM containment member 212 are illustrated respectively. The deployed configuration of the SAM containment member 212 (shown in FIG. 10) reveals that, in this embodiment, the lateral anterior arm 213a and the medial anterior arm 213d are conjoined, and that an attachment element 214 (an eyelet 214 in this embodiment) is disposed near the junction of the lateral anterior arm 213a and the medial anterior arm 213d. As described further below, the eyelet 214 provides an attachment element that can be used to control the configuration and deployment of the SAM containment member 212. In some embodiments, other types of attachment elements 214 (as alternatives to the eyelet 214) can be included on the SAM containment member 212. For example, in some embodiments one or more protrusions, ball ends, recesses, clips, breakable elements, deflectable elements, bends, and the like, and combinations thereof, can be included on the SAM containment member 212 as an attachment element 214.

In the depicted embodiment, the SAM containment member 212 is biased such that it naturally seeks to be arranged in the deployed configuration. Therefore, as described further below, in some embodiments when the SAM containment member 212 is released from being constrained in its pre-deployed configuration, the SAM containment member 212 will naturally reconfigure itself (or "self-reconfigure") into the deployed configuration (or an approximation thereof). In some embodiments, a shape-setting process is used to instill a bias so that the SAM containment member 212 tends seek its deployed configuration. Alternatively or additionally, as described further below, in some embodiments the SAM containment member 212 may be deflected into the deployed configuration by the application of one or more forces during the deployment of the SAM containment member 212.

In some implementations, while the SAM containment member 212 is deployed, the lateral anterior arm 213a and/or the medial anterior arm 213d may engage with the anterior leaflet and/or chordae to reduce the likelihood of SAM. The engagement can be anywhere along the lengths of the lateral anterior arm 213a and/or the medial anterior arm 213d, and at the juncture thereof. For example, in some implementations portions of the lateral anterior arm 213a and/or the medial anterior arm 213d that are near to the lateral anterior sub-annular support arm 230a and/or the medial anterior sub-annular support arm 230d can actually engage the lateral edge of the anterior leaflet and/or chordae to spread or widen the anterior leaflet at the lateral edges thereby restricting its movement and also reducing likelihood of SAM.

Figure 11:
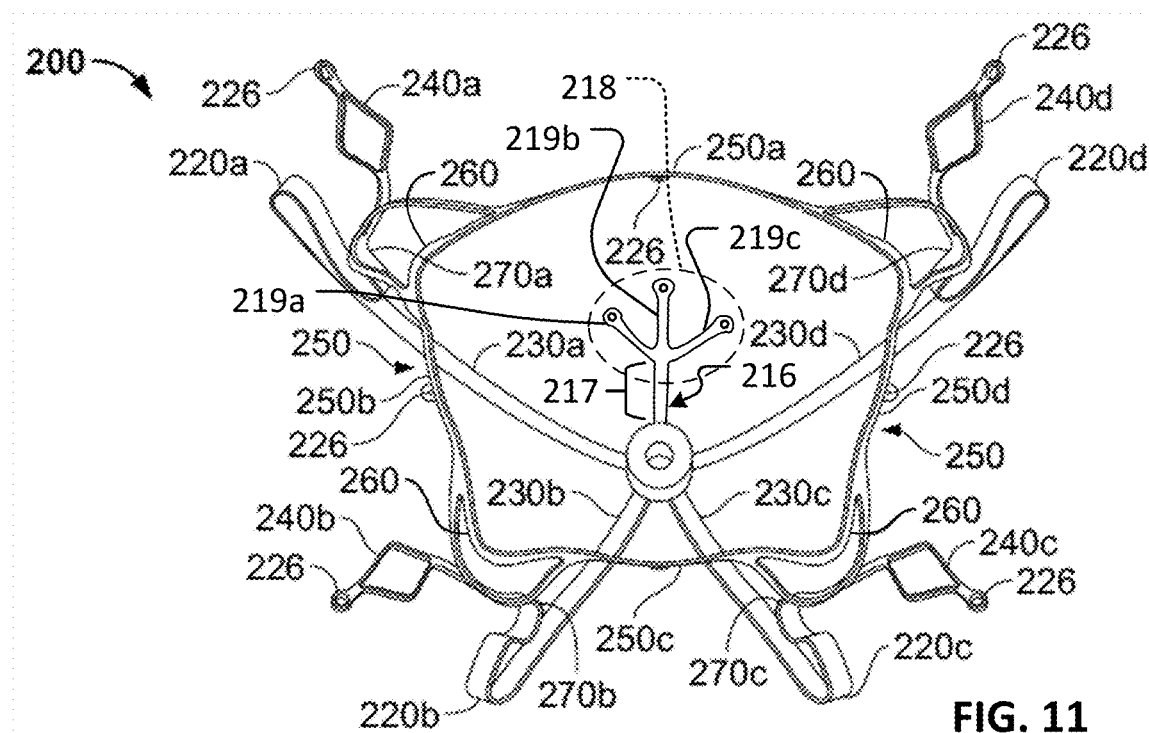
FIG. 11 shows a perspective top view of an example anchor assembly, including another example SAM containment member in a deployed configuration, in accordance with some embodiments.

In reference to FIG. 11, the anchor assembly 200 may additionally or alternately include another example embodiment of a SAM containment member 216. In the depicted embodiment, the SAM containment member 216 is fixedly attached to the hub 210, and extends in a generally anterior and superior direction from the hub 210.

The SAM containment member 216 includes an arm portion 217 attached to the hub 210, and an end portion 218 that extends from the arm portion 217. While in the depicted embodiment the arm portion 217 is a single elongate member, in some embodiments the arm portion 217 comprises two or more elongate members.

In some embodiments, as in the depicted embodiment, the end portion 218 extending from the elongate member arm portion 217 defines a width that is greater than the width of the arm portion 217. As described further below, the end portion 218 is configured to be disposed behind an anterior leaflet when the anchor assembly 200 is engaged with a native mitral valve. As used herein, "behind" an anterior leaflet refers to the aortic side of the native mitral valve leaflet when the leaflet is open.

In the depicted embodiment, the end portion 218 comprises a first elongate member 219a, a second elongate member 219b, and a third elongate member 219c (collectively referred to hereinafter as "three elongate members 219a-c"). The three elongate members 219a-c fan out from the arm portion 217. The three elongate members 219a-c thereby collectively define or encompass a broad area that will make contact with the back of the anterior leaflet of a mitral valve in situ. In some embodiments, one or more interconnecting struts may extend between the three elongate members 219a-c. In some embodiments, the fanned out arrangement of the three elongate members 219a-c is the natural or unconstrained arrangement of the three elongate members 219a-c. As described further below, prior to the deployment of the SAM containment member 216, the three elongate members 219a-c may be compressed towards each other for containment within a lumen of a low-profile delivery sheath. Upon emergence from the lumen, the three elongate members 219a-c may naturally diverge from each other into the fanned out arrangement as shown.

While the depicted embodiment of the end portion 218 includes three elongate members 219a-c that extend from the arm portion 217 in a fanned-out arrangement, various other configurations of the end portion 218 are also envisioned. For example, in some embodiments a single elongate member makes up the end portion 218. Such a single elongate member may be wider, narrower, or the same width as the arm portion 217. In some embodiments, the end portion may have two elongate members arranged in a V-shape or U-shape, and the like. In some embodiments, the end portion may include four or more elongate members. In some embodiments, the end portion may be a looped member, such as a circle, oval, triangle, rectangle, and the like. In some embodiments, the end portion 218 is generally planar. In some embodiments, the end portion 218 is contoured rather than planar. As with the three elongate members 219a-c described above, other configurations of the end portion 218 can be compressed for containment within a delivery sheath, and can self-expand into a larger (e.g., broader or wider) deployed configuration upon emergence from the delivery sheath.

While the three elongate members 219a-c of the depicted embodiment of the end portion 218 each include bulbous free ends, in some embodiments no such bulbous free ends are included. In the depicted embodiment, the bulbous free ends of the three elongate members 219a-c include eyelets. However, in some embodiments no such eyelets are included.

Figure 12:
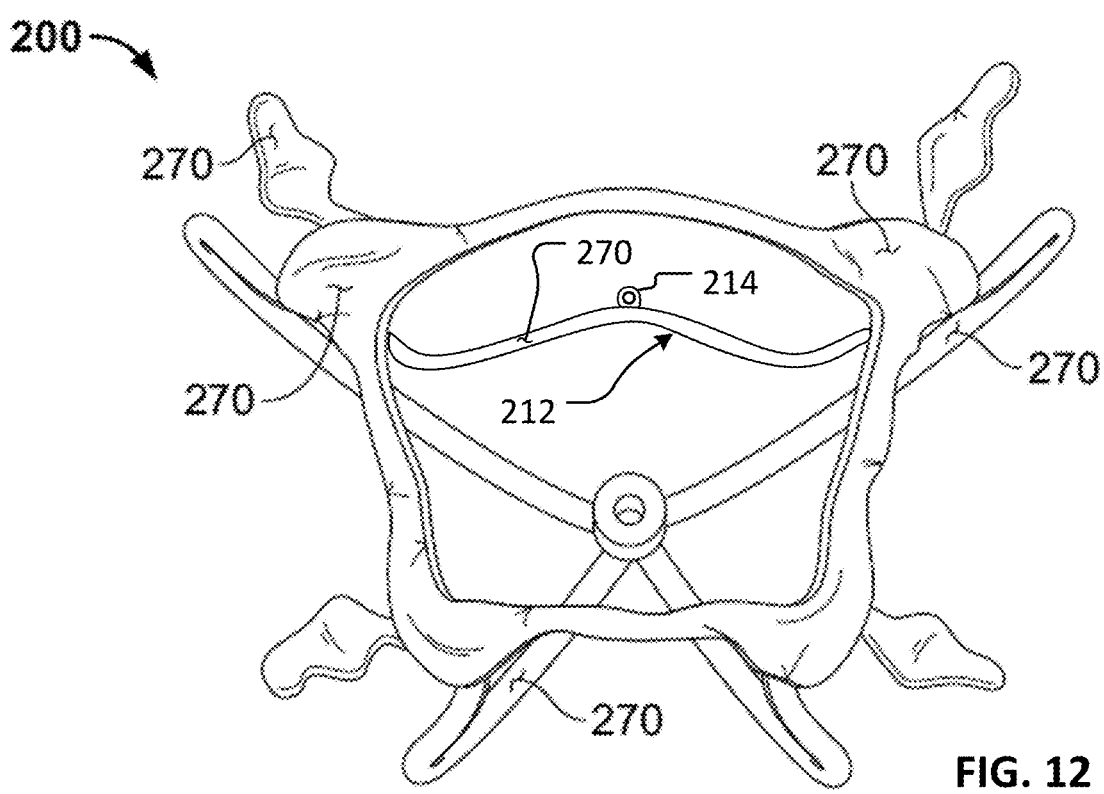
FIG. 12 shows a perspective top view of the anchor assembly of FIG. 10 with a covering material disposed on portions of the anchor frame.

In reference to FIG. 12, in some embodiments the anchor assembly 200 includes a covering material 270 disposed on one or more portions of the anchor assembly 200. The covering material 270 can provide various benefits. For example, in some implementations the covering material 270 can facilitate tissue ingrowth and/or endothelialization, thereby enhancing the migration resistance of the anchor assembly 200 and preventing thrombus formation on blood contact elements. In another example, as described further below, the covering material 270 can be used to facilitate coupling between the anchor assembly 200 and a valve assembly that is received therein. The cover material 270 also prevents or minimizes abrasion and/or fretting between the anchor assembly 200 and valve assembly 300. The cover material 270 also prevents valve outer tissue abrasion related wear, and supports to the cuff material to enhance durability. The covering material 270 may also provide redundant sealing in addition to the cuff material of the valve assembly.

In the depicted embodiment, the covering material 270 is disposed essentially on the entire anchor assembly 200, including the SAM containment member 212 (except for the eyelet 214, although in some embodiments the eyelet 214 may be essentially covered by the covering material 270). In some embodiments, the covering material 270 is disposed on one or more portions of the anchor assembly 200, while one or more other portions of the anchor assembly 200 do not have the covering material 270 disposed thereon. While the depicted embodiment includes the covering material 270, the covering material 270 is not required in all embodiments. In some embodiments, two or more portions of covering material 270, which can be separated and/or distinct from each other, can be disposed on the anchor assembly 200. That is, in some embodiments a particular type of covering material 270 is disposed on some areas of the anchor assembly 200 and a different type of covering material 270 is disposed on other areas of the anchor assembly 200.

In some embodiments, the covering material 270, or portions thereof, comprises a fluoropolymer, such as an expanded polytetrafluoroethylene (ePTFE) polymer. In some embodiments, the covering material 270, or portions thereof, comprises a polyester, a silicone, a urethane, ELAST-EON™ (a silicone and urethane polymer), another biocompatible polymer, DACRON®, polyethylene terephthalate (PET), copolymers, or combinations and subcombinations thereof. In some embodiments, the covering material 270 is manufactured using techniques such as, but not limited to, extrusion, expansion, heat-treating, sintering, knitting, braiding, weaving, chemically treating, and the like. In some embodiments, the covering material 270, or portions thereof, comprises a biological tissue. For example, in some embodiments the covering material 270 can include natural tissues such as, but not limited to, bovine, porcine, ovine, or equine pericardium. In some such embodiments, the tissues are chemically treated using glutaraldehyde, formaldehyde, or triglycidylamine (TGA) solutions, or other suitable tissue crosslinking agents.

In the depicted embodiment, the covering material 270 is disposed on the interior and the exterior of the anchor assembly 200. In some embodiments, the covering material 270 is disposed on the just the exterior of the anchor assembly 200. In some embodiments, the covering material 270 is disposed on the just the interior of the anchor assembly 200. In some embodiments, some portions of the anchor assembly 200 are covered by the covering material 270 in a different manner than other portions of the anchor assembly 200.

In some embodiments, the covering material 270 is attached to at least some portions of the anchor assembly 200 using an adhesive. In some embodiments, epoxy is used as an adhesive to attach the covering material 270 to the anchor assembly 200, or portions thereof. In some embodiments, wrapping, stitching, lashing, banding, and/or clips, and the like can be used to attach the covering material 270 to the anchor assembly 200. In some embodiments, a combination of techniques are used to attach the covering material 270 to the anchor assembly 200.

In some embodiments, the covering material 270, or portions thereof, has a microporous structure that provides a tissue ingrowth scaffold for durable sealing and/or supplemental anchoring strength of the anchor assembly 200. In some embodiments, the covering material 270 is made of a membranous material that inhibits or reduces the passage of blood through the covering material 270. In some embodiments, the covering material 270, or portions thereof, has a material composition and/or configuration that inhibits or prevents tissue ingrowth and/or endothelialization to the covering material 270.

In some embodiments, the covering material 270 can be modified by one or more chemical or physical processes that enhance certain physical properties of the covering material 270. For example, a hydrophilic coating may be applied to the covering material 270 to improve the wettability and echo translucency of the covering material 270. In some embodiments, the covering material 270 may be modified with chemical moieties that promote or inhibit one or more of endothelial cell attachment, endothelial cell migration, endothelial cell proliferation, and resistance to thrombosis. In some embodiments, the covering material 270 may be modified with covalently attached heparin or impregnated with one or more drug substances that are released in situ.

In some embodiments, covering material 270 is pre-perforated to modulate fluid flow through the covering material 270 and/or to affect the propensity for tissue ingrowth to the covering material 270. In some embodiments, the covering material 270 is treated to make the covering material 270 stiffer or to add surface texture. In some embodiments, selected portions of the covering material 270 are so treated, while other portions of the covering material 270 are not so treated. Other covering material 270 material treatment techniques can also be employed to provide beneficial mechanical properties and tissue response interactions. In some embodiments, portions of the covering material 270 have one or more radiopaque markers attached thereto to enhance in vivo radiographic visualization.

Figure 13A:
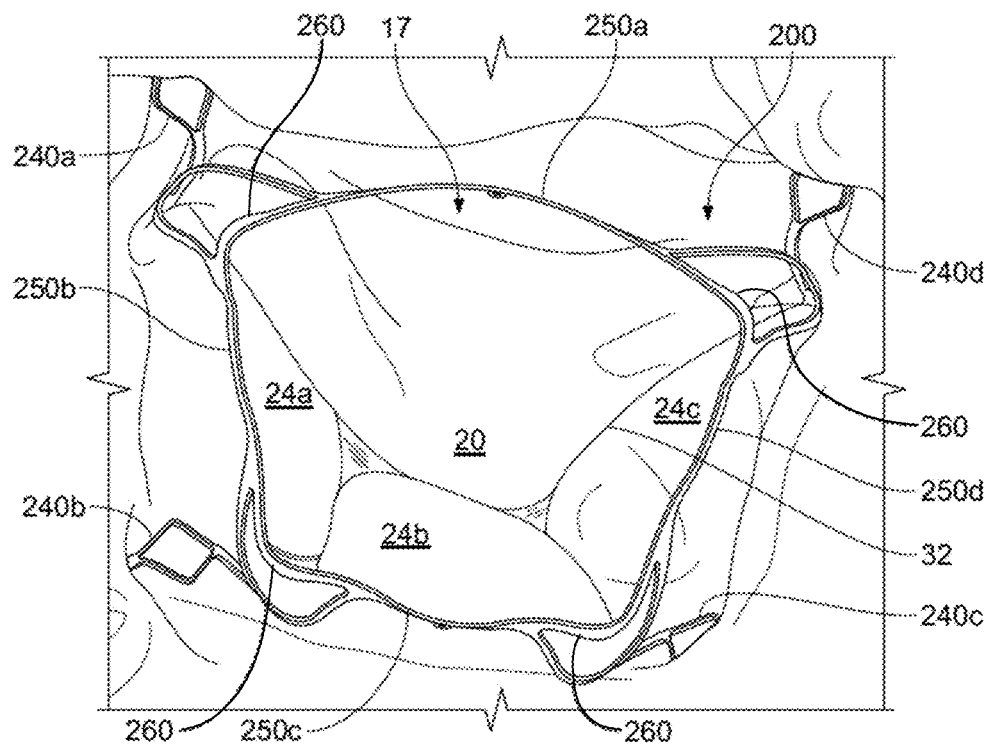
FIG. 13A shows a perspective top view of the anchor assembly of FIG. 10 implanted within a native mitral valve (with the native mitral valve leaflets in a closed state)
Figure 13B:
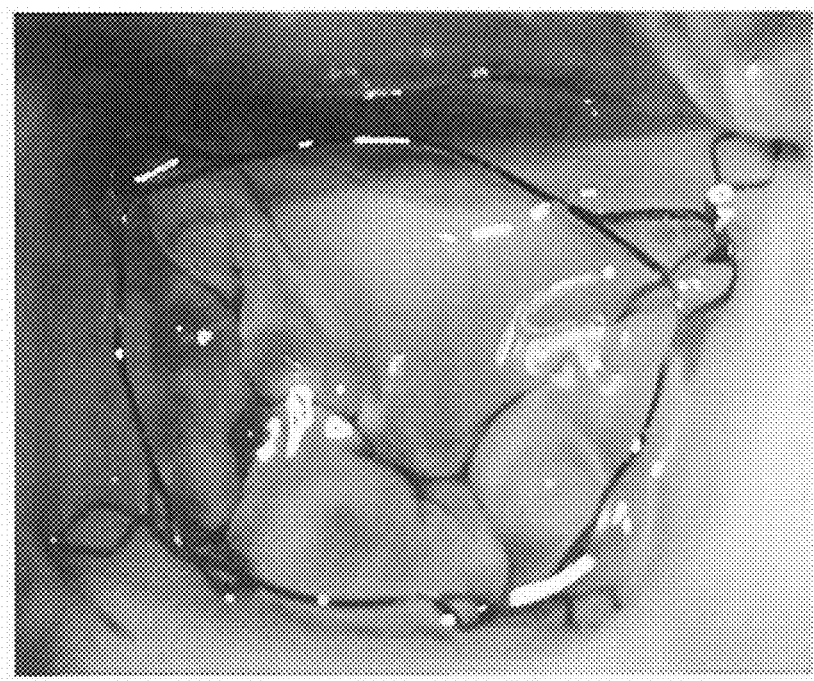
FIG. 13B shows a corresponding anatomical top view of the anchor assembly of FIG. 13A.
Figure 14A:
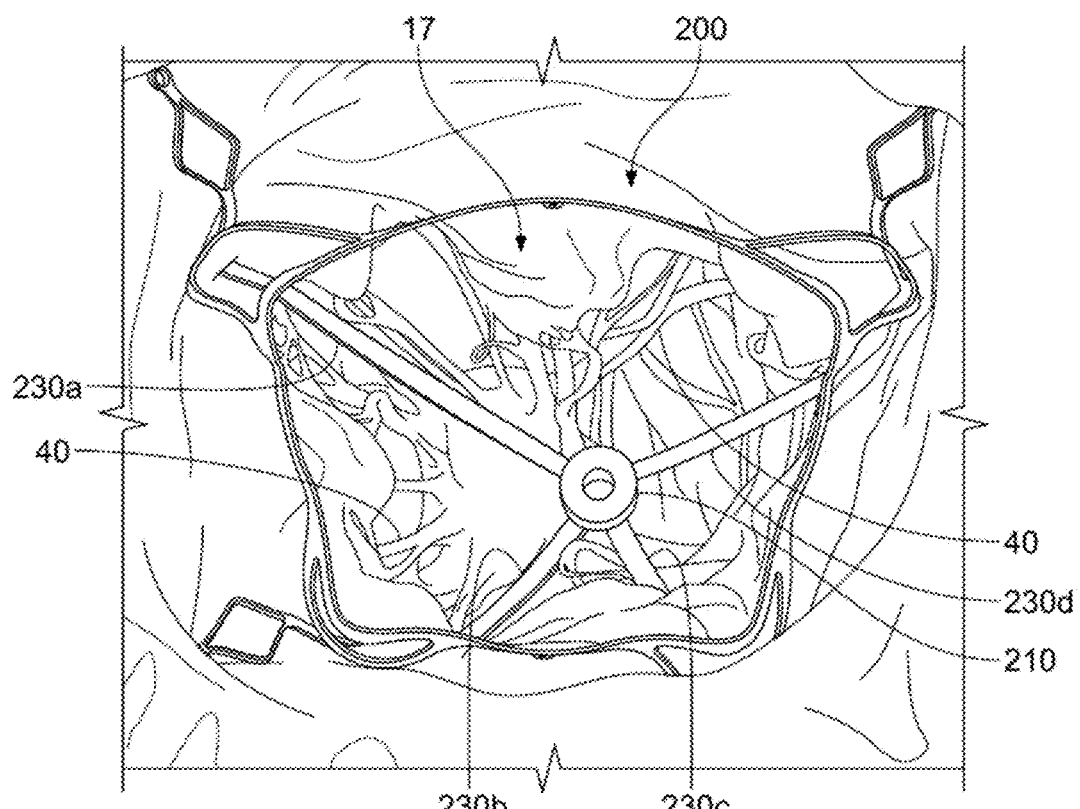
FIG. 14A shows a perspective top view of the anchor assembly of FIG. 10 implanted within the native mitral valve of FIG. 13A (with the native mitral valve leaflets in an open state)
Figure 14B:
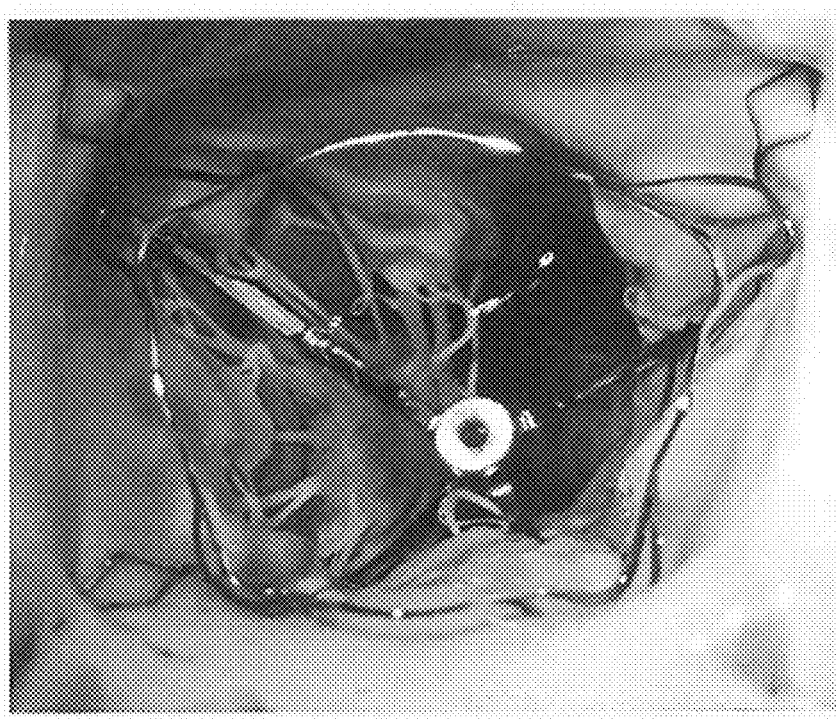
FIG. 14B shows a corresponding anatomical top view of the anchor assembly of FIG. 14A.

Referring now to FIGS. 13A and 14A, the anchor assembly 200 is shown implanted within a native mitral valve 17. FIGS. 13B and 14B are photographs that correspond to FIGS. 13A and 14A respectively. In FIG. 13A, the mitral valve 17 is shown in a closed state. In FIG. 14A, the mitral valve 17 is shown in an open state. These illustrations are from the perspective of the left atrium looking towards the mitral valve 17. For instance, in FIG. 14A chordae tendineae 40 are visible through the open leaflets of the mitral valve 17.

These figures illustrate the supra-annular structures and sub-annular structures of the anchor assembly 200 in their relationships with the native mitral valve 17. For example, the closed state of the native mitral valve 17 in FIG. 13A allows visibility of the supra-annular structures such as the lateral anterior atrial holding feature 240a, the lateral posterior atrial holding feature 240b, the medial posterior atrial holding feature 240c, and the medial anterior atrial holding feature 240d. In addition, the anterior anchor arch 250a, the left anchor arch 250b, the posterior anchor arch 250c, the right anchor arch 250d, and the connection bridges 260 are visible. However, the sub-annular structures are not visible in FIG. 13A because such structures are obstructed from view by the anterior leaflet 20 and the three-part posterior leaflet 24a, 24b, and 24c.

In contrast, in FIG. 14A certain sub-annular structures of the anchor assembly 200 are visible because the native mitral valve 17 is open. For example, sub-annular support arms 230a, 230b, 230c, and 230d and hub 210 are in view through the open mitral valve 17. Nevertheless, the anchor feet 220a, 220b, 220c, and 220d remain out of view because of their location within the sub-annular gutter of the mitral valve 17. In addition, no SAM containment member (which is a sub-annular structure) is visible in this view.

Figure 15:
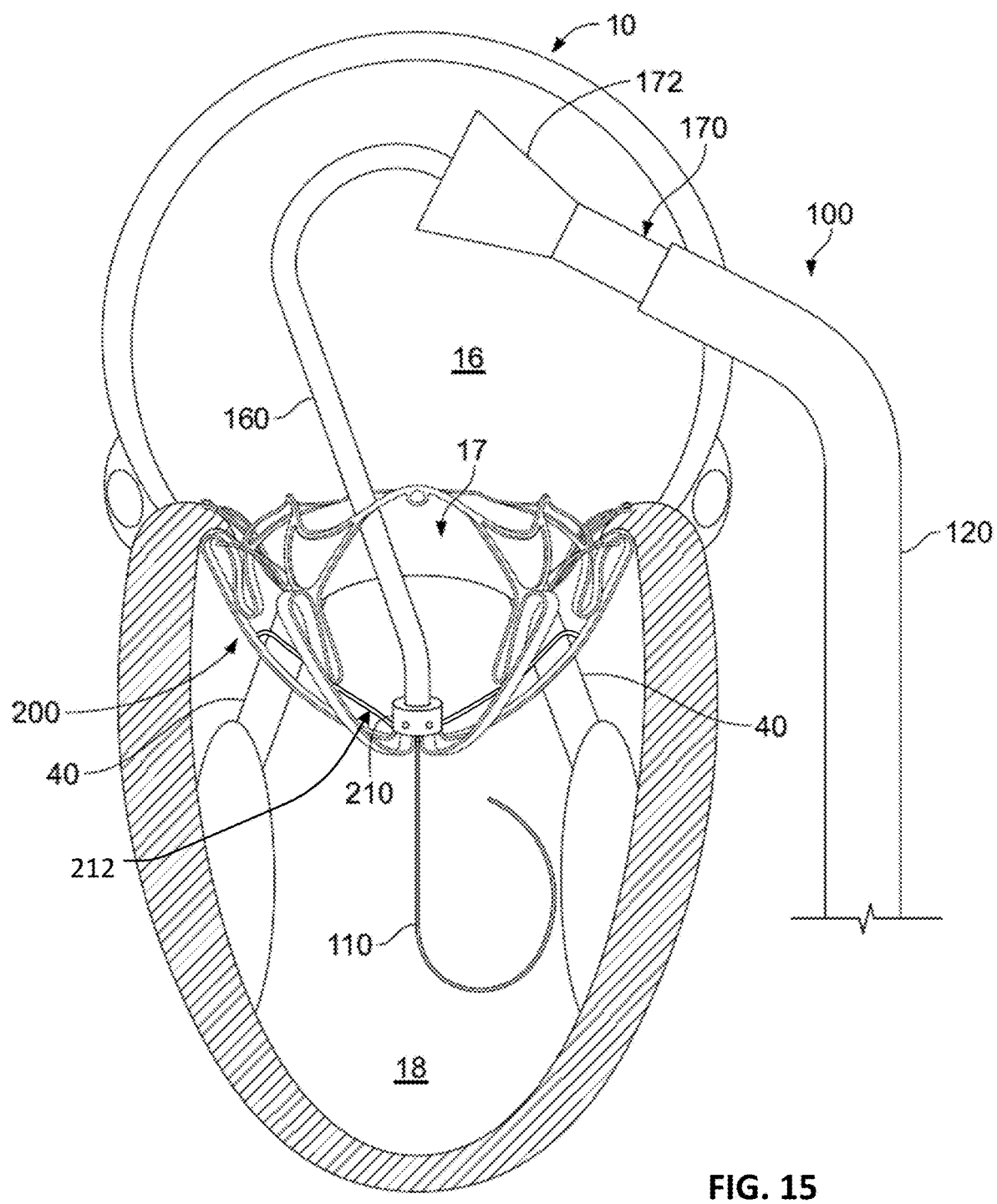
FIG. 15 shows a perspective view of the anchor assembly of FIG. 7 implanted within the native mitral valve and a valve assembly delivery sheath extending into the left atrium.

Referring to FIG. 15, after implantation of the anchor assembly 200 within the native mitral valve 17 (as performed, for example, in accordance with FIGS. 1-7 described above), a valve delivery sheath 170 of the delivery system 100 can be used to deploy a valve assembly within the anchor assembly 200. As described above in reference to FIG. 7, with the inner catheter 160 coupled with the hub 210 of the anchor assembly 200, the inner catheter 160 can be used to guide the valve assembly into the interior of the anchor assembly 200.

In the depicted embodiment, the SAM containment member 212 is constrained in its pre-deployed configuration. However, in some other SAM containment member embodiments, the SAM containment member may be deployed prior to installation of a valve assembly within the anchor assembly 200. Generally speaking, depending on the SAM containment member embodiment's design, if the SAM containment member may potentially interfere with the function of the anterior leaflet, it may be preferable to wait until the valve is implanted to deploy the SAM containment member. But, if the SAM containment member does not or is unlikely to interfere with the leaflet function, the SAM containment member may be deployed prior to valve implant (which may be beneficial for situations where the anchor is implanted in a separate procedure from the valve implantation).

In some implementations, with the guide catheter 120 positioned with its distal end in the left atrium 16, the valve delivery sheath 170 is installed into a lumen of the guide catheter 120 (over the inner catheter 160) and advanced through the guide catheter 120. As described further below, in some embodiments the valve delivery sheath 170 is preloaded with a prosthetic valve assembly and other components of the delivery system 100. The guide catheter 120 may be the same catheter that was used to deliver the anchor assembly 200, or it may be a different catheter (but still referred to here as the guide catheter 120 for simplicity sake). Depending on the time interval between implantation of the anchor assembly 200 and the valve assembly 300, it may also be desirable to leave the same guide catheter 120 in situ during the time between the deliveries of each assembly.

In some embodiments, the valve delivery sheath 170 can be made from the materials described above in reference to the guide catheter 120. In some embodiments, the valve delivery sheath 170 has an outer diameter in the range of about 20 Fr to about 28 Fr (about 6.7 mm to about 9.3 mm). In some embodiments, the valve delivery sheath 170 has an outer diameter in the range of about 14 Fr to about 24 Fr (about 4.7 mm to about 8.0 mm).

In the depicted embodiment, the valve delivery sheath 170 includes a flared distal end portion 172. In some embodiments, no such flared distal end portion 172 is included. The flared distal end portion 172 can collapse to a lower profile when constrained within the guide catheter 120. When the flared distal end portion 172 is expressed from the guide catheter 120, the flared distal end portion 172 can self-expand to the flared shape. In some embodiments, the material of the flared distal end portion 172 includes pleats or folds, may be a continuous flared end or may be separated into sections such as flower pedals, and may include one or more resilient elements that bias the flared distal end portion 172 to assume the flared configuration in the absence of restraining forces (such as from containment within the guide catheter 120). The flared distal end portion 172 can be advantageous, for example, for recapturing the valve assembly (if desired) within the lumen of the valve delivery sheath 170 after the valve assembly has been expressed from the flared distal end portion 172.

In some embodiments, the maximum outer diameter of the flared distal end portion 172 is in a range of about 30 Fr to about 34 Fr (about 10.0 mm to about 11.3 mm). In some embodiments, the maximum outer diameter of the flared distal end portion 172 is in a range of about 32 Fr to about 44 Fr (about 10.7 mm to about 14.7 mm). In some embodiments, the maximum outer diameter of the flared distal end portion 172 is in a range of about 24 Fr to about 30 Fr (about 8.0 mm to about 10.0 mm). In some embodiments, the maximum outer diameter of the flared distal end portion 172 is less than about 24 Fr (about 8.0 mm) or greater than about 44 Fr (about 14.7 mm).

Figure 16:
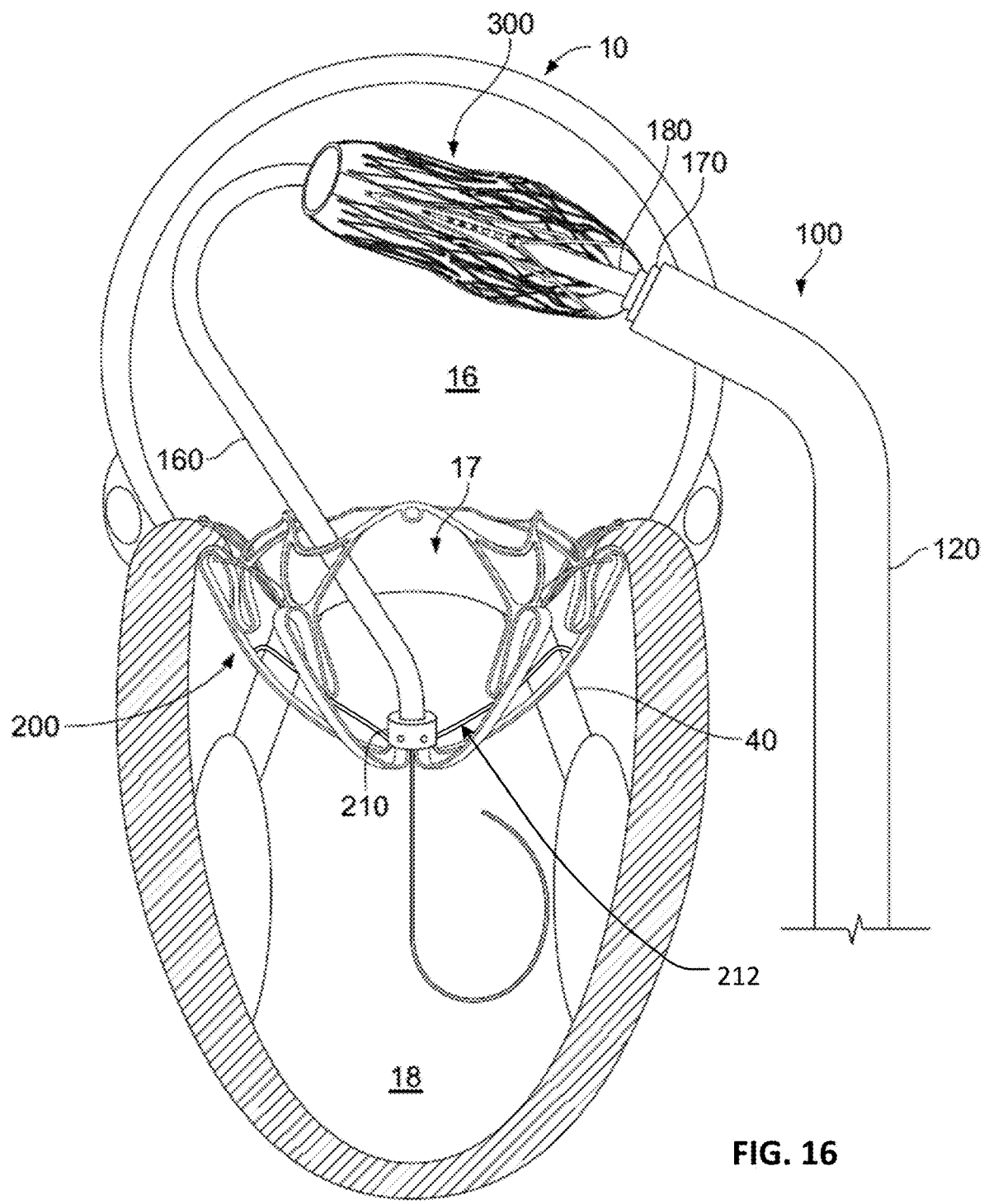
FIG. 16 shows a perspective view of a valve assembly in the left atrium after partial emergence from the valve assembly delivery sheath of FIG. 15. The valve assembly is configured in a first (partially expanded) arrangement.

Referring to FIG. 16, in some implementations the valve delivery sheath 170 can be withdrawn into the guide catheter 120 while a valve delivery catheter 180 is held substantially stationary to thereby express a valve assembly 300 from a lumen of the valve delivery sheath 170. The valve delivery sheath 170 and the valve delivery catheter 180 are additional components in some embodiments of the example delivery system 100. It should be understood that movements of the components (e.g., the valve delivery sheath 170 and the valve delivery catheter 180) of the delivery system 100, whether the movements be those of individual components or two or more components in combination with each other, can in some embodiments be initiated and controlled using a deployment frame system (such as the example deployment frame systems described below).

The valve assembly 300 can be releasably coupled to the valve delivery catheter 180 and retained in a low-profile configuration. In some embodiments, both the distal and proximal ends of the valve assembly 300 are releasably coupled to the valve delivery catheter 180. In some embodiments, just one of the distal end or the proximal end of the valve assembly 300 is releasably coupled to the valve delivery catheter 180. In particular embodiments, one or more control wires may be included to releasably couple one or more portions of the valve assembly 300 to the valve delivery catheter 180. In some such embodiments, the one or more control wires may act as lassos to radially constrain the bias of the valve assembly 300 to radially self-expand. Hence, a release of tension on the one or more control wires may allow at least a portion of the valve assembly 300 to radially self-expand.

Figure 17:
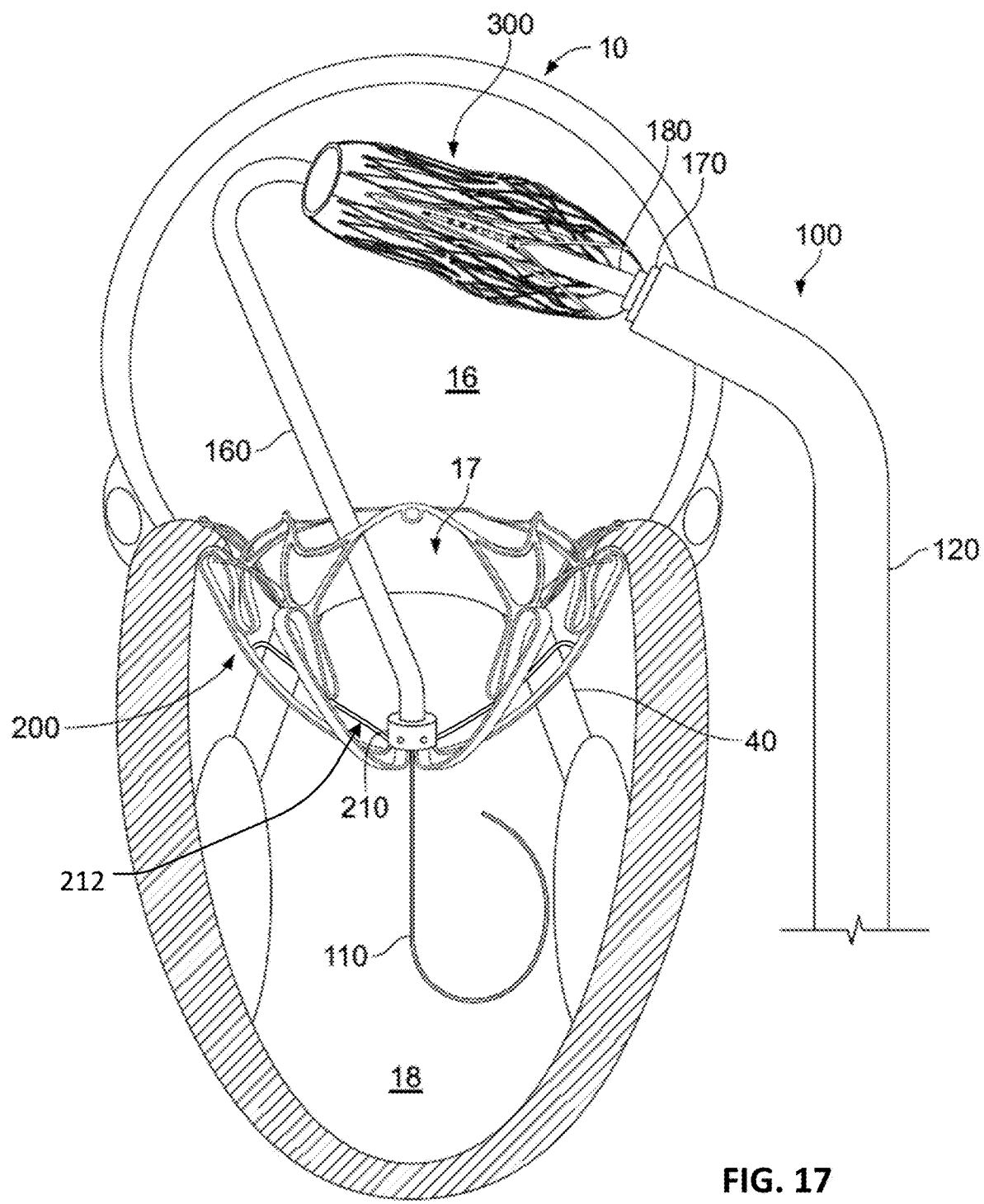
FIG. 17 shows a perspective view of the valve assembly of FIG. 16 with the valve deployment system being manipulated in preparation for the installation of the valve assembly into the anchor assembly.
Figure 18:
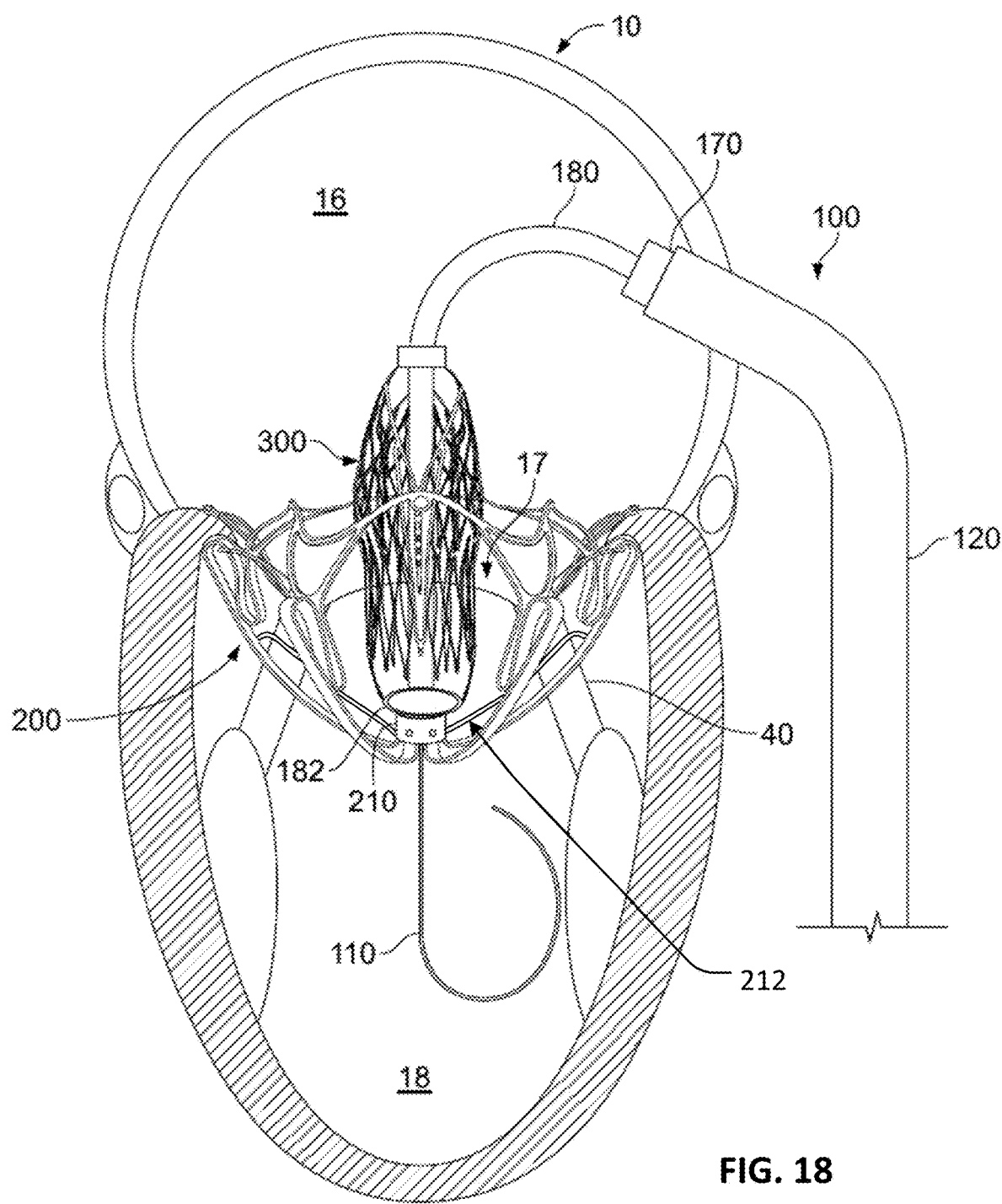
FIG. 18 shows a perspective view of the valve assembly of FIG. 17 (while still in the first (partially expanded) arrangement) being positioned within the anchor assembly.

Referring to FIGS. 17 and 18, the delivery system 100 can be manipulated by a clinician operator to perform a lateral pivot (panning, rotation, etc.) of the valve assembly 300 within the left atrium 16. The rotation of the valve assembly 300 changes the alignment of the valve assembly 300 from being generally axial with the distal end portion of the guide catheter 120 to being generally axial with the anchor assembly 200 (in preparation for installation of the valve assembly 300 into the interior of the anchor assembly 200).

In some implementations, the aforementioned rotation of the valve assembly 300 can be performed as follows. As shown in FIG. 17, because of the influence from the guide catheter 120 on the valve delivery catheter 180, the axis of the valve assembly 300 is initially in general alignment with the axis of the distal end portion of the guide catheter 120. From this arrangement, a generally simultaneous counter-movement of/between the inner catheter 160 and the valve delivery catheter 180 can be performed by the clinician to rotate the valve assembly 300. That is, as the inner catheter 160 is pulled proximally, the valve delivery catheter 180 is pushed distally. As a result of that counter movement, the valve assembly 300 rotates/pans in a relatively tight radius within the left atrium 16, as required by the confines of the left atrium 16. Thereafter, the valve delivery catheter 180 can be advanced further so that the valve assembly 300 is coaxially positioned within the interior of the anchor assembly 200 as shown in FIG. 18. As with other movements of the components of the delivery system 100 described herein (and other movements of the components of the delivery system 100 that are like those described herein), the generally simultaneous counter-movements of/between the inner catheter 160 and the valve delivery catheter 180 can be initiated and controlled using a deployment frame system (such as the example deployment frame systems described below) in some implementations.

Figure 19:
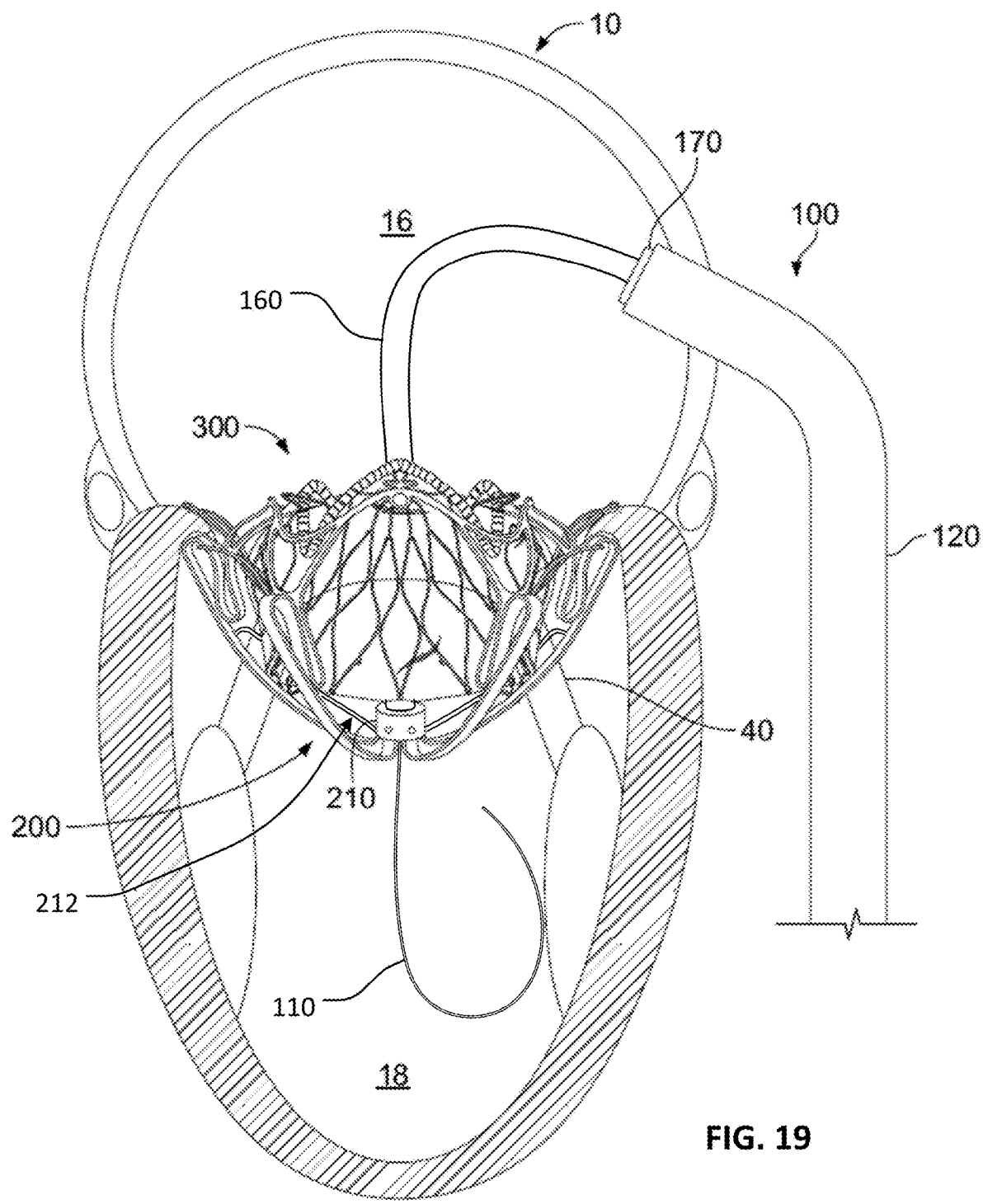
FIG. 19 shows a perspective view of the valve assembly of FIG. 18, with the valve assembly expanded within the anchor assembly and detached from the deployment system, but prior to deployment of the SAM containment member.

Referring now also to FIG. 19, in some embodiments the valve assembly 300 and the anchor assembly 200 become aligned with each other coaxially, linearly (along their axes), and rotationally prior to or during the expansion of the valve assembly 300, resulting in engagement between the valve assembly 300 and the anchor assembly 200.

Coaxial alignment between the valve assembly 300 and the anchor assembly 200, as described above, is achieved by virtue of the valve delivery catheter 180 being slidably disposed over the inner catheter 160. Linear alignment between the valve assembly 300 and the anchor assembly 200 can be achieved by the interaction of a distal end feature 182 of the valve delivery catheter 180 and the hub 210 of the anchor assembly 200. For example, in some embodiments an abutting of the distal end feature 182 and the hub 210 can result in proper linear alignment between the valve assembly 300 and the anchor assembly 200. Such abutting of the distal end feature 182 and the hub 210 can be attained by translating the valve delivery catheter 180 distally until the distal end feature 182 abuts the hub 210.

Relative rotational alignment between the valve assembly 300 and the anchor assembly 200 (about their longitudinal axes) can be achieved in various manners. For example, in some embodiments the valve delivery catheter 180 is mechanically keyed to the inner catheter 160 to slidably fix a desired rotational alignment between the valve assembly 300 and the anchor assembly 200. In some embodiments, other types of mechanical features (e.g., pins/holes, protrusions/receptacles, etc.) can be included to facilitate a desired rotational/spin alignment between the valve assembly 300 and the anchor assembly 200. Alternatively, or additionally, radiopaque markers can be included on the valve assembly 300 and on the anchor assembly 200 (including on the SAM containment member) in locations and/or patterns that are indicative of the relative rotational orientation (about their axes) of the valve assembly 300 and the anchor assembly 200. In some embodiments (e.g., when the valve delivery catheter 180 is configured to be "torqueable"), the valve delivery catheter 180 can be rotated about its longitudinal axis until the radiopaque markers are in proper position relative to the anchor assembly 200, prior to final expansion of valve assembly 300. Such rotation of the valve delivery catheter 180 can, in some implementations, be initiated and controlled using a deployment frame system (such as the example deployment frame systems described below). Fluoroscopy can be used to attain a desired relative orientation of the radiopaque markers, and of the valve assembly 300 and the anchor assembly 200 (including on the SAM containment member) correspondingly.

In the depicted implementation, the SAM containment member 212 is still in its pre-deployed configuration. Therefore, the depicted embodiment of the SAM containment member 212 is deployed after the valve assembly 300 is engaged within the anchor assembly 200. However, for some alternative embodiments of the SAM containment member (as described further below) the SAM containment member is deployed prior to the engagement of the valve assembly 300 within the anchor assembly 200.

After proper alignment between the valve assembly 300 and the anchor assembly 200 is achieved, the valve assembly 300 can be expanded within the interior of the anchor assembly 200 such that the valve assembly 300 and anchor assembly 200 become releasably coupled to each other. In some embodiments, force(s) are applied to the valve assembly 300 to cause it to expand. In some embodiments, the valve assembly 300 is biased to self-expand. The expansion of a self-expanding valve assembly 300 can be initiated by releasing tension on the one or more control wires of the valve delivery catheter 180. For example, in some embodiments the valve delivery catheter 180 includes a first control wire that restrains the proximal end portion of the valve assembly 300, and a second control wire that restrains the distal end portion of the valve assembly 300. As tension on the first control wire is released, the proximal end portion of the valve assembly 300 is allowed to radially expand. Similarly, as tension on the second control wire is released, the distal end portion of the valve assembly 300 is allowed to radially expand. The expansions of the portions of the valve assembly 300 may be allowed to take place sequentially, concurrently, or partially concurrently. As described further below, such individual and/or simultaneous movements of components of the delivery system 100 (such as the one or more control wires of the valve delivery catheter 180) can be initiated and controlled using a deployment frame system (such as the example deployment frame systems described below) in some implementations.

After the valve assembly 300 has been expanded into a coupled relationship with the anchor assembly 200, the clinician can verify that the anchor assembly 200 and the valve assembly 300 are in the desired positions. Additionally, the clinician may verify other aspects such as, but not limited to, the hemodynamic performance and sealing of the anchor assembly 200 and the valve assembly 300.

In some embodiments, the SAM containment member 212 is deployed after the valve assembly 300 has been expanded into a coupled relationship with the anchor assembly 200. To deploy the SAM containment member 212, in some embodiments the inner catheter 160 is rotated about its longitudinal axis so that the distal end of the inner catheter 160 is unthreaded from the hub 210 of the anchor assembly 200. Then, in some embodiments the guidewire 110 is retracted to allow full deployment of the SAM containment member 212

With the valve assembly 300 and the anchor assembly 200 fully deployed and functioning as desired, the remaining components of the delivery system 100 can be withdrawn. To do so, the valve delivery catheter 180 and the inner catheter 160 can be retracted into the guide catheter 120. Then the valve delivery catheter 180, the inner catheter 160, and the guide catheter 120 can be jointly or individually withdrawn from the patient.

Figure 20:
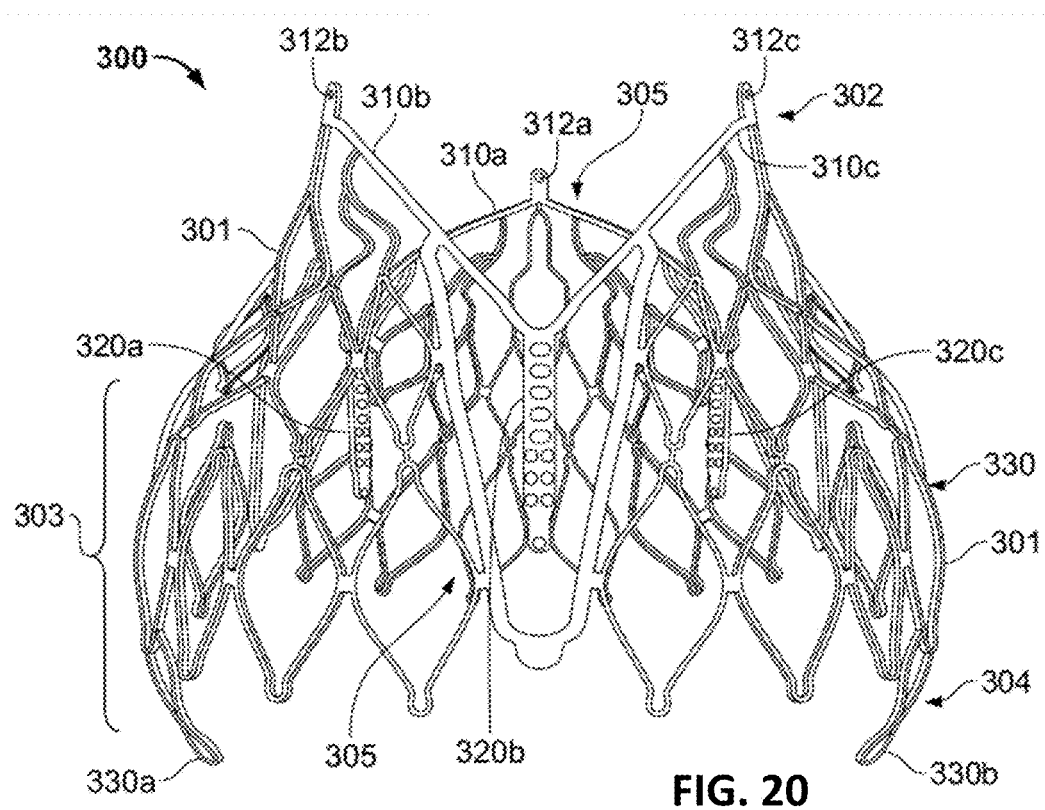
FIG. 20 shows an anterior side view of a valve frame of a valve assembly of FIGS. 16-19, in accordance with some embodiments.
Figure 21:
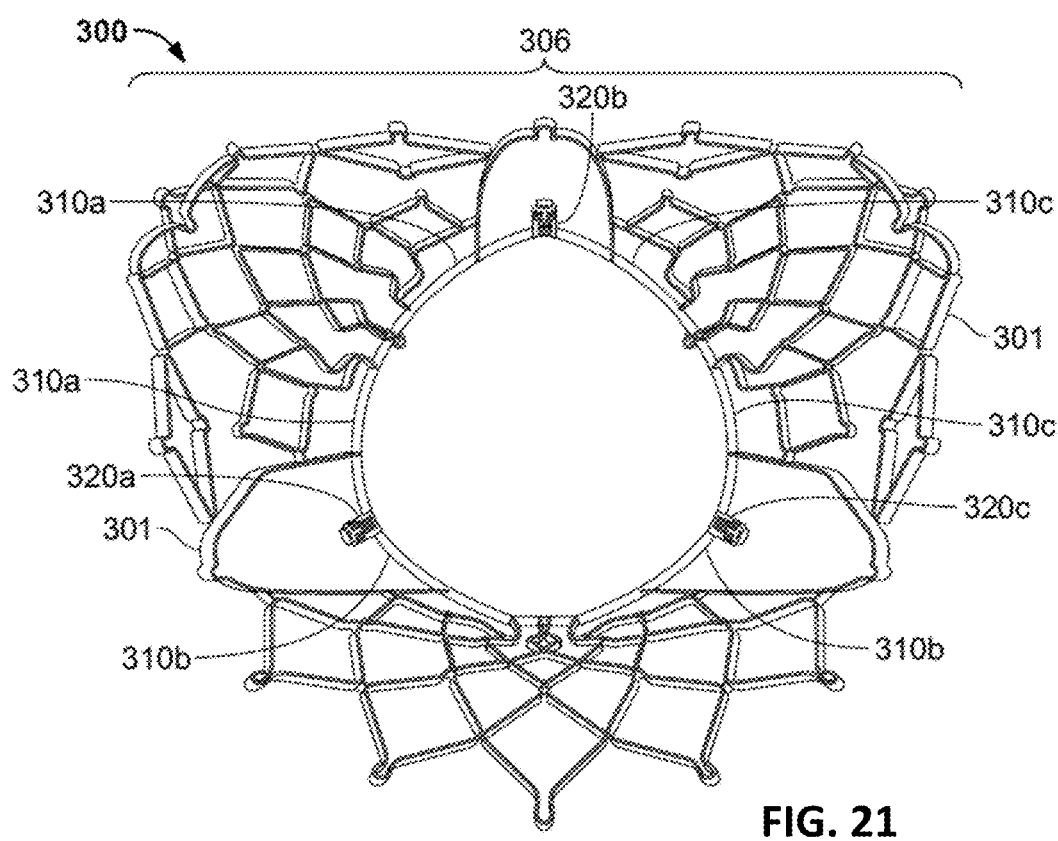
FIG. 21 shows a bottom view of the valve frame of FIG. 20.

Referring to FIGS. 20 and 21, an example valve assembly 300 is shown without any covering or valve/occluder leaflets. Hence, a valve assembly frame 301 of the valve assembly 300 is shown. FIG. 20 shows an anterior side view of the valve assembly frame 301, and FIG. 21 shows a bottom view of the valve assembly frame 301. The valve assembly 300 can be constructed using any of the various materials and manufacturing techniques described above in reference to the anchor frame 200 (e.g., refer to FIG. 9). It should be understood that the depicted valve assembly 300 is merely one non-limiting example of the valve assemblies provided within the scope of this disclosure.

The valve assembly 300 includes a proximal end portion 302 and a distal end portion 304. The valve assembly includes a flared external skirt portion 303 and defines an interior orifice portion 305. When the valve assembly 300 is implanted in a native mitral valve, the proximal end portion 302 is located supra-annular (in the left atrium) and the distal end portion 304 is located sub-annular (in the left ventricle). The proximal end portion 302 defines the generally circular entrance orifice of the valve assembly 300, as described further below.

In the depicted embodiment, the valve assembly 300 generally flares outward along a distal direction. Said differently, the distal end portion 304 is flared outward in comparison to the proximal end portion 302. Accordingly, the proximal end portion 302 defines a smaller outer profile in comparison to the distal end portion 304. However, some regions of the distal end portion 304 bow inwardly. In particular, for example, a posteromedial commissural corner 330a and anterolateral commissural corner 330b of the valve assembly 300 may bow inwardly. It should be understood that the outward flare of the distal end portion 304 in comparison to the proximal end portion 302 is merely one example configuration for a profile of the valve assembly 300. In some embodiments, for example, a shoulder (a portion of the valve assembly 300 having the largest outer periphery) is located proximal of the middle of the valve assembly 300.

The valve assembly 300 also includes an anterior side 306 between the posteromedial commissural corner 330a and anterolateral commissural corner 330b. When the valve assembly 300 is implanted in a native mitral valve, the anterior side 306 faces the anterior leaflet of the native mitral valve. The anterior side 306 of the distal end portion 304 defines a generally flat surface, whereas the other sides of the distal end portion 304 are rounded. Hence, the periphery of the distal end portion 304 is generally D-shaped. The D-shaped periphery of the distal end portion 304 provides the valve assembly 300 with an advantageous outer profile for interfacing and sealing with the native mitral valve. As described further below, sealing is attained by coaptation between the D-shaped periphery of the distal end portion 304 and the leaflets of the native mitral valve, and, in some embodiments, between the D-shaped periphery in the region of the skirt 303 with the native valve annulus.

In the depicted embodiment, the proximal end portion 302 of the valve assembly 300 includes three atrial leaflet arches 310a, 310b, and 310c that together define an undulating ring at the proximal end portion 302. Each of the leaflet arches 310a, 310b, and 310c includes an apex having an attachment hole 312a, 312b, and 312c respectively. In some embodiments, the attachment holes 312a, 312b, and 312c are used for coupling the proximal end of the valve assembly 300 to a delivery catheter (e.g., valve delivery catheter 180 of FIGS. 16-18).

The valve assembly 300 also includes three commissural posts 320a, 320b, and 320c that each extend distally from the intersections of the three leaflet arches 310a, 310b, and 310c. The commissural posts 320a, 320b, and 320c are disposed at about 120° apart from each other. The commissural posts 320a, 320b, and 320c each have a series of holes that can be used for attachment of leaflets, such as by suturing. The three leaflet arches 310a, 310b, and 310c and the three commissural posts 320a, 320b, and 320c are areas on the valve assembly 300 to which three prosthetic valve leaflets become attached to comprise a tri-leaflet occluder (e.g., refer to FIGS. 23-26).

As seen in FIG. 21, the three leaflet arches 310a, 310b, and 310c and the commissural posts 320a, 320b, and 320c define a generally cylindrical frame for the tri-leaflet occluder construct. As such, the valve assembly 300 provides a proven and advantageous frame configuration for the tri-leaflet occluder. The tri-leaflet occluder provides open flow during diastole and occlusion of flow during systole.

Referring to FIG. 22, an exploded depiction of an example prosthetic mitral valve 400 includes an anchor assembly 200 and a valve assembly 300. This figure provides a posterior side view of the anchor assembly 200 and the valve assembly 300.

The valve assembly 300 includes a covering 340. The covering 340 can be made of any of the materials and constructed using any of the techniques described above in reference to covering 270. Additionally, in some embodiments the covering 340 can comprise natural tissues such as, but not limited to, bovine, porcine, ovine, or equine pericardium. In some such embodiments, the tissues are chemically cross-linked using glutaraldehyde, formaldehyde, or triglycidyl amine solution, or other suitable crosslinking agents.

When the valve assembly 300 and the anchor assembly 200 are coupled together, the valve assembly 300 is geometrically interlocked within the interior of the anchor assembly 200 (e.g., in some embodiments by virtue of the tapered shape of the valve assembly 300 within the supra-annular ring and interior space of the anchor assembly 200).

In particular, in some embodiments the valve assembly 300 is contained within the interior space between the supra-annular ring 250 and the sub-annular support arms 230a, 230b, 230c, and 230d. As described above, the interlocked arrangement between the valve assembly 300 and the anchor assembly 200 is accomplished by positioning a valve assembly 300 in a low-profile configuration within the interior of the anchor assembly 200 and then allowing expansion of the valve assembly 300 within the interior of the anchor assembly 200 (e.g., refer to FIGS. 18 and 19).

Figure 23:
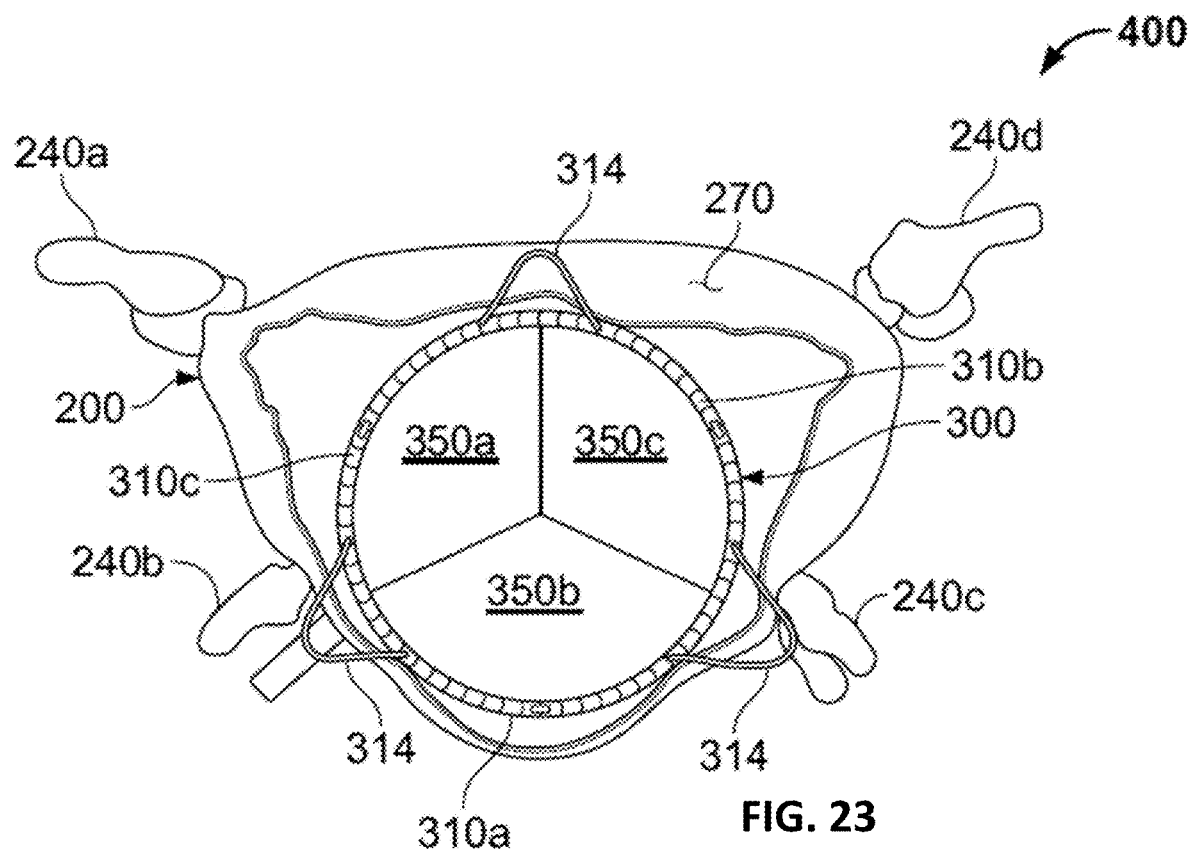
FIG. 23 is a top view of an example prosthetic mitral valve system that includes a valve assembly engaged with an anchor assembly, in accordance with some embodiments.
Figure 24:
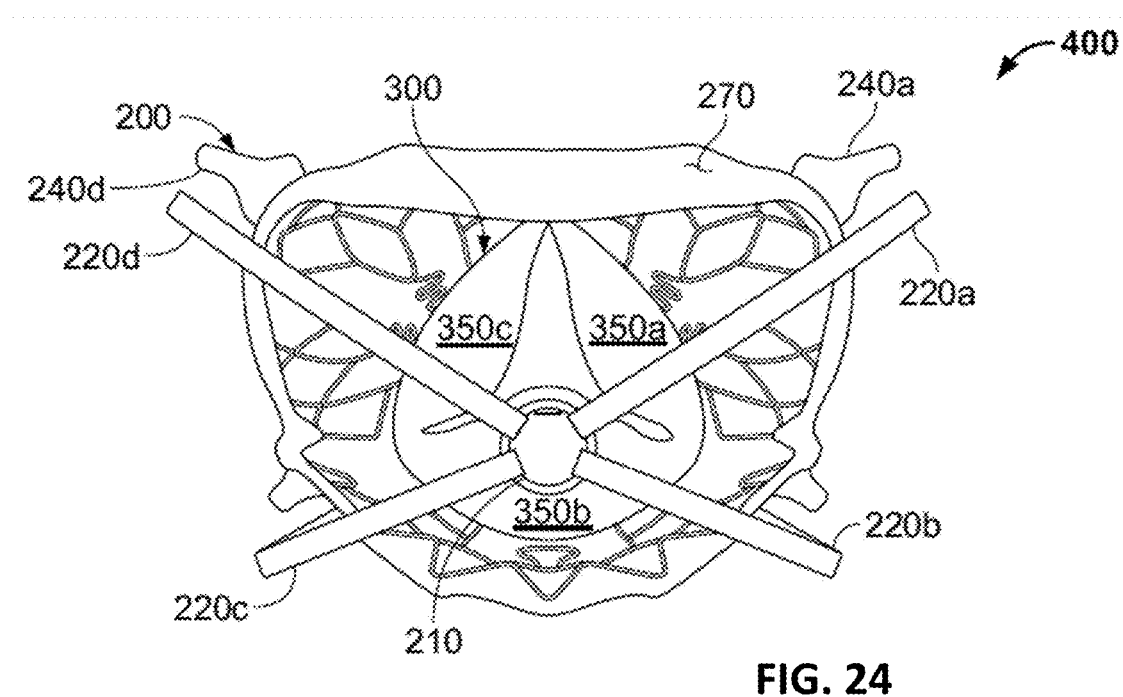
FIG. 24 is a bottom view of the example prosthetic mitral valve system of FIG. 23.

Referring to FIGS. 23 and 24, a deployed configuration of the example prosthetic mitral valve 400 includes the valve assembly 300 engaged within the anchor assembly 200. FIG. 23 shows a top (atrial) view of the prosthetic mitral valve 400, and FIG. 24 shows a bottom (ventricle) view of the prosthetic mitral valve 400.

In some embodiments, such as the depicted embodiment, valve assembly 300 includes three leaflets 350a, 350b, and 350c that perform the occluding function of the prosthetic mitral valve 400. The cusps of the three leaflets 350a, 350b, and 350c are fixed to the three atrial leaflet arches 310a, 310b, and 310c, and to the three commissural posts 320a, 320b, and 320c (refer to FIGS. 20 and 21). The free edges of the three leaflets 350a, 350b, and 350c can seal by coaptation with each other during systole and open during diastole.

The three leaflets 350a, 350b, and 350c can be comprised of natural or synthetic materials. For example, the three leaflets 350a, 350b, and 350c can be comprised of any of the materials described above in reference to the covering 340, including the natural tissues such as, but not limited to, bovine, porcine, ovine, or equine pericardium. In some such embodiments, the tissues are chemically cross-linked using glutaraldehyde, formaldehyde, or triglycidyl amine solution, or other suitable crosslinking agents. In some embodiments, the leaflets 350a, 350b, and 350c have a thickness in a range of about 0.005" to about 0.020" (about 0.13 mm to about 0.51 mm), or about 0.008" to about 0.012" (about 0.20 mm to about 0.31 mm). In some embodiments, the leaflets 350a, 350b, and 350c have a thickness that is less than about 0.005" (about 0.13 mm) or greater than about 0.020" (about 0.51 mm).

In some embodiments, the occluding function of the prosthetic mitral valve 400 can be performed using configurations other than a tri-leaflet occluder. For example, bi-leaflet, quad-leaflet, or mechanical valve constructs can be used in some embodiments.

In some embodiments, a SAM containment member is included as part of the anchor assembly 200 (e.g., refer to FIGS. 10 and 11). In the depicted embodiment, no SAM containment member is included.

Figure 25:
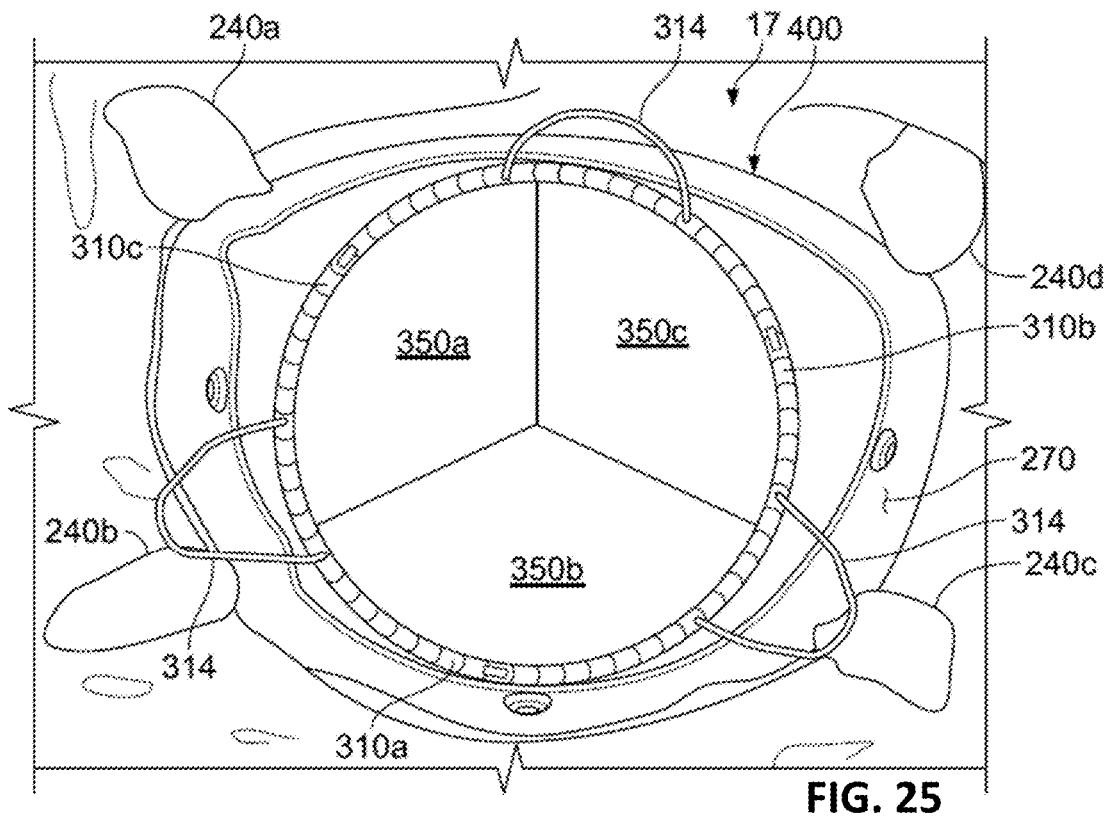
FIG. 25 shows a top view of the prosthetic mitral valve system of FIG. 23 implanted within a native mitral valve. The occluder portion of prosthetic mitral valve system is shown in a closed state.
Figure 26:
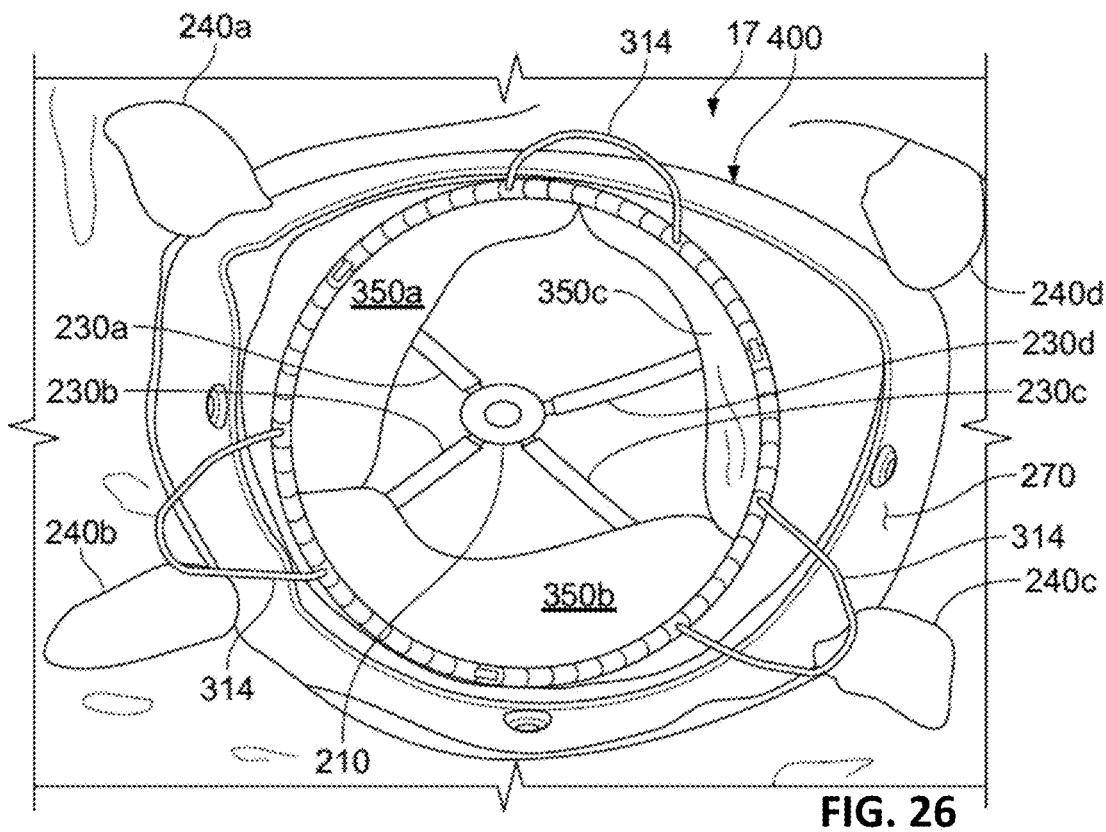
FIG. 26 shows a top view of the prosthetic mitral valve system of FIG. 23 implanted within a native mitral valve. The occluder portion of the prosthetic mitral valve system is shown in an open state.

Referring to FIGS. 25 and 26, the prosthetic mitral valve 400 is shown implanted within a native mitral valve 17. In FIG. 25, the prosthetic mitral valve 400 is shown in a closed state (occluded). In FIG. 26, the prosthetic mitral valve 400 is shown in an open state. These illustrations are from the perspective of the left atrium looking towards the mitral valve 17. For instance, in FIG. 26 the hub 210 and the sub-annular support arms 230a, 230b, 230c, and 230d of the anchor assembly 200 are visible through the open leaflets 350a, 350b, and 350c of the prosthetic mitral valve 400, whereas in FIG. 25 the hub 210 and the sub-annular support arms 230a, 230b, 230c, and 230d are not visible because the closed leaflets 350a, 350b, and 350c block the hub 210 from view.

Referring to FIG. 27, in some implementations the prosthetic mitral valve 400 is deployed in a patient 1 using the transcatheter delivery system 100 as described above. In some implementations, the prosthetic mitral valve 400 is percutaneously deployed via a femoral or iliac vein through a groin opening/incision 2 in the patient 1. In particular implementations, a deployment frame system 6 is used to initiate and/or control the movements of various components of the transcatheter delivery system 100.

While the deployment frame systems provided herein are described in the context of the deployment of the prosthetic mitral valve 400 using the transcatheter delivery system 100, it should be understood that the practical applications of the inventive concepts associated with the deployment frame systems provided herein are not limited to such a context. That is, the inventive concepts associated with the deployment frame systems provided herein can be applied to contexts such as, but not limited to, other types of delivery systems for prosthetic heart valves of any type, deployment systems for other types of medical devices/implants, and so on.

In the depicted embodiment, the deployment frame system 6 is attached or releasably attached to an operating table 4 on which the patient 1 is laying. In some embodiments, the deployment frame system 6 is separated or substantially separated from the operating table 4.

As described above in reference to FIGS. 1-7 and 15-19, the deployment of the prosthetic mitral valve 400 is, in summary, a two-step process. The first step is the deployment of the anchor assembly 200, and the second step is the deployment of the valve assembly 300. As described further below, some components of the deployment frame systems provided herein may be used for both steps, while other components of the deployment frame systems provided herein may be used for one or the other of the two steps.

In general, the configurations of the deployment frame systems 6 provided herein are different for the two deployment steps (i.e., the first step being the deployment of the anchor assembly 200, and the second step being the deployment of the valve assembly 300). That is, the configuration of the deployment frame system 6 for delivering the anchor assembly 200 is different than the configuration of the deployment frame system 6 for delivering the valve assembly 300.

Figure 28A:
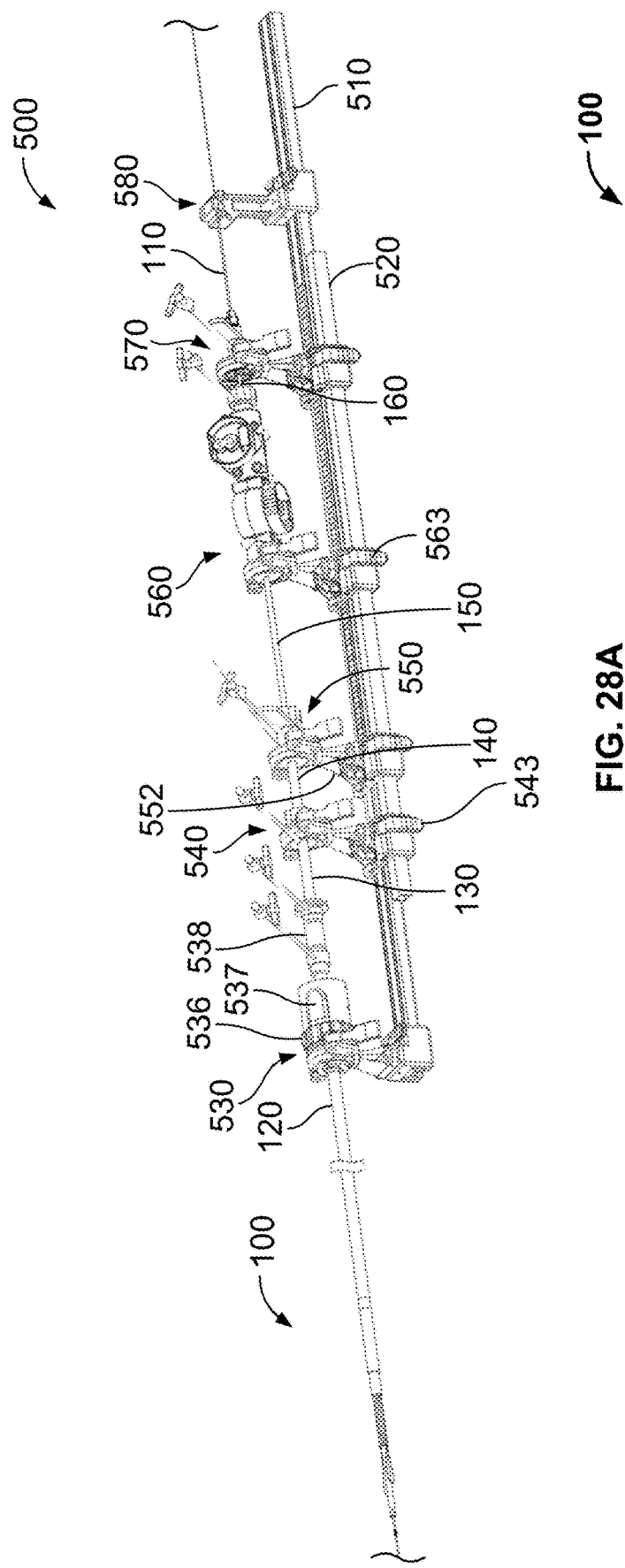
FIG. 28A shows a perspective view of an example deployment frame system configuration in accordance with some embodiments.

Referring to FIG. 28A, an example deployment frame system 500 can be configured to deploy a prosthetic mitral valve anchor assembly 200 (refer to FIGS. 1-14B) using the transcatheter delivery system 100. While the depicted deployment frame system 500 is configured for deploying the anchor assembly 200, it should be understood that this context is one illustrative example of how the inventive concepts provided herein can be implemented. That is, the inventive concepts described in the context of deployment frame system 500 can be adapted and implemented for the percutaneous deployment of many other types of prosthetic implants, medical devices, and the like, either via percutaneous, endovascular, minimally invasive, or open surgical procedures, and the like.

The deployment frame system 500 can be implemented, for example, as generally depicted in FIG. 27. That is, in some embodiments deployment frame system 500 can be affixed to an operating table 4 (or another type of mounting base), in a desired positional relationship with a patient 1. For example, in some implementations deployment frame system 500 is positioned relative to the patient 1 so that the implantable device (e.g., example prosthetic mitral valve 400) is percutaneously inserted into a femoral or iliac vein via a groin incision 2 in a patient 1.

Figure 28B:
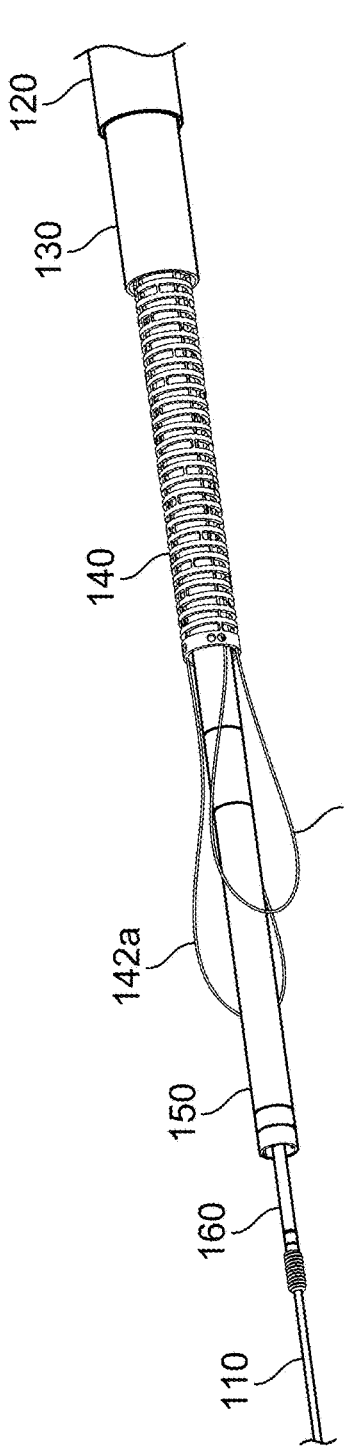
FIGS. 28B and 28C show enlarged views of portions of the deployment frame system of FIG. 28A.

Referring also to FIG. 28B, transcatheter delivery system 100 can be releasably coupled with deployment frame system 500, as described further below. The deployment frame system 500 can be used by one or more clinicians to initiate and control movements of the components of the delivery system 100. Some such movements of the components of the delivery system 100 are described above in reference to FIGS. 1-7 and 15-19.

As described above, the example transcatheter delivery system 100 includes the guidewire 110, the guide catheter 120, the anchor delivery sheath 130, the anchor delivery catheter 140, the secondary steerable catheter 150, and the inner catheter 160. In general, in the depicted embodiment those components of delivery system 100 are disposed in a telescopic fashion in relation to each other. That is, the guidewire 110 is slidably disposed within the inner catheter 160; the inner catheter 160 is slidably disposed within the secondary steerable catheter 150; the secondary steerable catheter 150 is slidably disposed within the anchor delivery catheter 140; the anchor delivery catheter 140 is slidably disposed within the anchor delivery sheath 130; and the anchor delivery sheath 130 is slidably disposed within the guide catheter 120.

A proximal end portion of each of those components (the guidewire 110, the guide catheter 120, the anchor delivery sheath 130, the anchor delivery catheter 140, the secondary steerable catheter 150, and the inner catheter 160) is terminated at a respective location along the deployment frame system 500. As described further below, by manipulating the respective components' proximal end portions (individually or in unison) using the deployment frame system 500, clinicians can initiate and control movements of the delivery system 100.

The example deployment frame system 500 includes a main frame 510, a secondary frame 520, a guide catheter control assembly 530, an anchor delivery sheath control assembly 540, an anchor delivery catheter control assembly 550, a secondary steerable catheter control assembly 560, an inner catheter control assembly 570, and a guidewire control assembly 580. Each of the guide catheter control assembly 530, the anchor delivery sheath control assembly 540, the anchor delivery catheter control assembly 550, the secondary steerable catheter control assembly 560, the inner catheter control assembly 570, and the guidewire control assembly 580 is releasably coupled to the main frame 510. In addition, the anchor delivery sheath control assembly 540, the anchor delivery catheter control assembly 550, the secondary steerable catheter control assembly 560, and the inner catheter control assembly 570 are also releasably coupled to the secondary frame 510. In some implementations of deployment frame system 500 for deploying the anchor assembly 200, no inner catheter control assembly 570 is included. Rather, the inner catheter 160 can be floating on the guidewire 110.

In the depicted embodiment, the proximal end of the guide catheter 120 terminates at the guide catheter control assembly 530, which is releasably coupled to the main frame 510. Proximal end portions of other components of the delivery system (e.g., the anchor delivery sheath 130, the anchor delivery catheter 140, the secondary steerable catheter 150, the inner catheter 160, and the guidewire 110) extend proximally past the guide catheter control assembly 530 (by virtue of the other components' telescopic relationship to the guide catheter 120).

In the depicted embodiment, the proximal end of the anchor delivery sheath 130 terminates at the anchor delivery sheath control assembly 540, which is releasably coupled to the main frame 510 and to the secondary frame 520. Proximal end portions of other components of the delivery system (e.g., the anchor delivery catheter 140, the secondary steerable catheter 150, the inner catheter 160, and the guidewire 110) extend proximally past the anchor delivery sheath control assembly 540 (by virtue of the other components' telescopic relationship to the anchor delivery sheath 130).

In the depicted embodiment, the proximal end of the anchor delivery catheter 140 terminates at the anchor delivery catheter control assembly 550, which is releasably coupled to the main frame 510 and to the secondary frame 520. Proximal end portions of other components of the delivery system (e.g., the secondary steerable catheter 150, the inner catheter 160, and the guidewire 110) extend proximally past the anchor delivery catheter control assembly 550 (by virtue of the other components' telescopic relationship to the anchor delivery catheter 140).

In the depicted embodiment, the proximal end of the secondary steerable catheter 150 terminates at the secondary steerable catheter control assembly 560, which is releasably coupled to the main frame 510 and to the secondary frame 520. Proximal end portions of other components of the delivery system (e.g., the inner catheter 160, and the guidewire 110) extend proximally past the secondary steerable catheter control assembly 560 (by virtue of the other components' telescopic relationship to the secondary steerable catheter 150).

In the depicted embodiment, the proximal end of the inner catheter 160 terminates at the inner catheter control assembly 570, which is releasably coupled to the main frame 510 and to the secondary frame 520. A proximal end portion of the guidewire 110 extends proximally past the inner catheter control assembly 570 (by virtue of the guidewire's telescopic relationship to the inner catheter 160).

In the depicted embodiment, a proximal end portion of the guidewire 110 extends through (e.g., releasably clamped) the guidewire control assembly 580, which is releasably coupled to the main frame 510.

As described above in reference to FIGS. 1-7 and 15-19, various movements of the components of the delivery system 100 may be desired during the process of deploying (or retrieving) a medical device, such as the anchor assembly 200 and valve assembly 300 of prosthetic mitral valve 400 (refer to FIG. 22). For example, the types of desired movements of the components of the delivery system 100 may include, but are not limited to: (i) a distal longitudinal translation, (ii) a proximal longitudinal translation, (iii) rotations about the longitudinal axis in either direction, (iv) a deflection of one or more portions of a component (e.g., steering or bending), and (v) a tensioning or untensioning of a control wire.

In some implementations, it may be desirable to initiate some of such movements (e.g., example movements (i)-(v) above) in synchronization (e.g., generally simultaneously) with one or more other such movements. One example, of desirable simultaneous movement of two or more components of the delivery system 100 was described above in reference to FIG. 4. In that example, the inner catheter 160 and the anchor delivery catheter 140 were translated distally in conjunction with each other, while maintaining the positions of the other components of the delivery system 100 (e.g., the secondary steerable catheter 150) generally stationary. As described further below, the secondary frame 520 can be advantageously utilized to facilitate such synchronization of movements of two or more components of the delivery system 100.

Figure 28C:
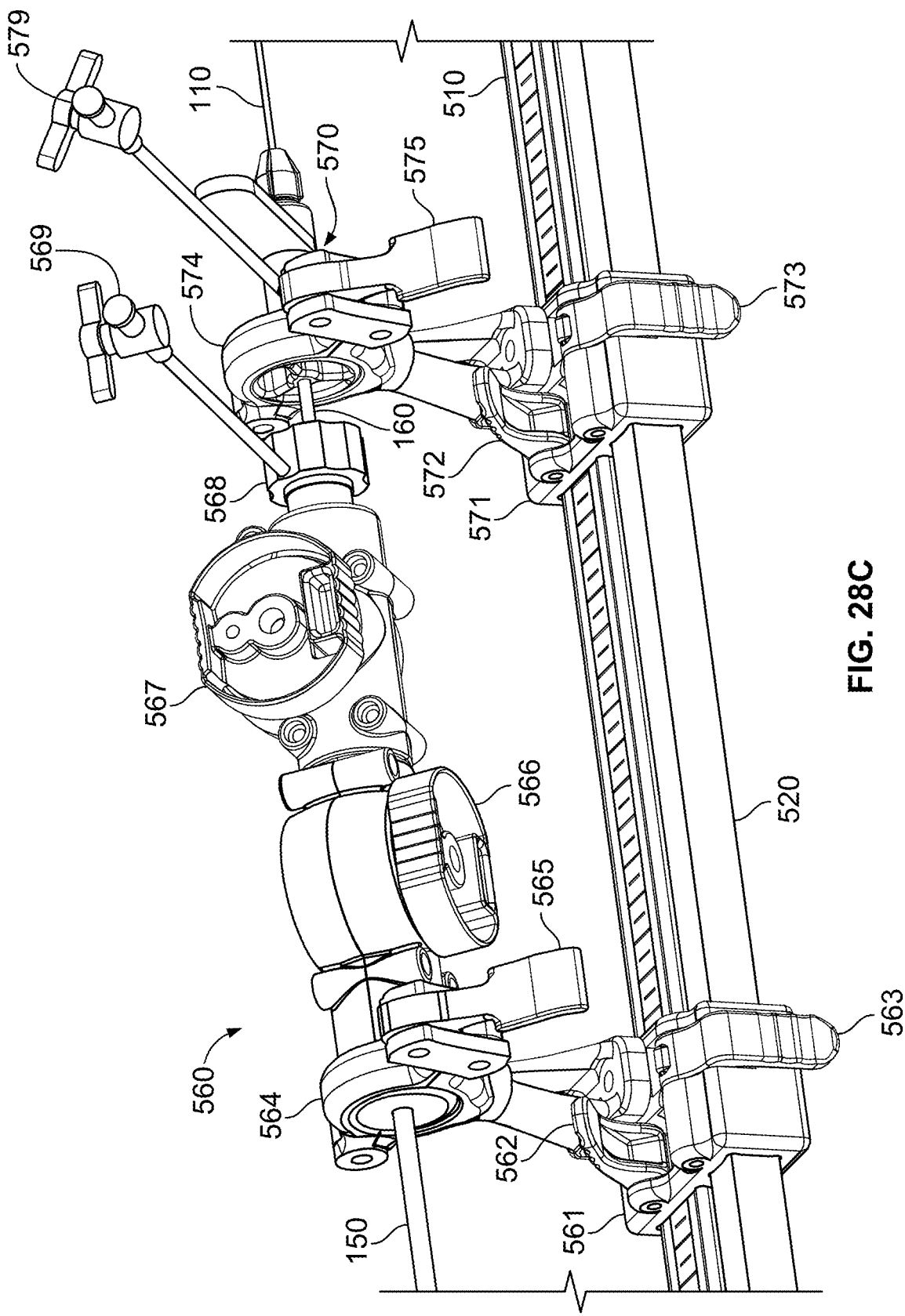

Referring also to FIG. 28C, in the depicted embodiment of the deployment frame system 500 each control assembly (e.g., the guide catheter control assembly 530, the anchor delivery sheath control assembly 540, the anchor delivery catheter control assembly 550, the secondary steerable catheter control assembly 560, the inner catheter control assembly 570, and the guidewire control assembly 580) is releasably coupled to one or both of the main frame 510 and the secondary frame 520. For example, the secondary steerable catheter control assembly 560 is coupled to both the main frame 510 and the secondary frame 520. In particular, the secondary steerable catheter control assembly 560 is coupled to the main frame 510 via a clamp base 561 and a pivotable toggle clamp 562. An upward or downward pivoting motion of the toggle clamp 562 effectuates an unlocking and a locking of the clamp base 561 in relation to the main frame 510. The toggle clamp 562 (and other toggle clamps described herein) may include a cam profile surface that can be pivoted into place to create a friction fit between two components that effectively locks the two components together. Moreover, in the depicted embodiment the secondary steerable catheter control assembly 560 is also coupled to the secondary frame 520, via the clamp base 561 and a pivotable toggle clamp 563. An upward or downward pivoting motion of the toggle clamp 563 effectuates an unlocking and a locking of the clamp base 561 in relation to the secondary frame 520. When the secondary steerable catheter control assembly 560 is unlocked from both the main frame 510 and the secondary frame 520, the secondary steerable catheter control assembly 560 is essentially free to be translated (e.g., slid) distally or proximally in relation to both the main frame 510 and the secondary frame 520.

In the depicted embodiment, the other control assemblies (e.g., the guide catheter control assembly 530, the anchor delivery sheath control assembly 540, the anchor delivery catheter control assembly 550, the inner catheter control assembly 570, and the guidewire control assembly 580) are similarly releasably coupled to one or both of the main frame 510 and the secondary frame 520. For example, the inner catheter control assembly 570 is releasably coupled to both the main frame 510 and the secondary frame 520. In particular, the inner catheter control assembly 570 is coupled to the main frame 510 via a clamp base 571 and a pivotable toggle clamp 572. An upward or downward pivoting motion of the toggle clamp 572 effectuates an unlocking and a locking of the clamp base 571 in relation to the main frame 510. Moreover, in the depicted embodiment the inner catheter control assembly 570 is also coupled to the secondary frame 520, via the clamp base 571 and a pivotable toggle clamp 573. An upward or downward pivoting motion of the toggle clamp 573 effectuates an unlocking and a locking of the clamp base 571 in relation to the secondary frame 520. When the inner catheter control assembly 570 is unlocked from both the main frame 510 and the secondary frame 520, the inner catheter control assembly 570 is essentially free to be translated (e.g., slid) distally or proximally in relation to both the main frame 510 and the secondary frame 520.

While in the depicted embodiment the control assemblies 530, 540, 550, 560, 570, and 580 are releasably coupled to one or both of the main frame 510 and the secondary frame 520 using a toggle clamp mechanism, it should be understood that additionally, or alternatively, other types of mechanisms can be used. For example, in some embodiments mechanisms such as, but not limited to, spring detents, set screws, collar clamps, gears (e.g., a rack and pinion), pins, and the like, can be used.

One of skill in the art will recognize that various individual and/or group movements of the control assemblies 530, 540, 550, 560, 570, and 580 can be facilitated by locking and/or unlocking the couplings of particular ones of the control assemblies 530, 540, 550, 560, 570, and 580 from one or both of the main frame 510 and the secondary frame 520, as described in the following example.

To distally translate the anchor delivery catheter 140 and the inner catheter 160 in conjunction with each other, while maintaining the positions of the other components of the delivery system 100 stationary (i.e., to facilitate the movement described above in reference to FIG. 4) the clinician can perform the following actions. To start with, all the clamps are in their locked configurations. The clamp 552 that locks the anchor delivery catheter control assembly 550 to the main frame 510, and the clamp 572 that locks the inner catheter control assembly 570 to the main frame 510 should both be unlocked. With clamps 552 and 572 unlocked, the anchor delivery catheter control assembly 550 and the inner catheter control assembly 570 are free to be moved in relation to the main frame 510. Then, the clamp 543 that locks the anchor delivery sheath control assembly 540 to the secondary frame 520, and the clamp 563 that locks the secondary steerable catheter control assembly 560 to the secondary frame 520 should both be unlocked (leaving the anchor delivery catheter 140 and inner catheter 160 both secured to the secondary frame 520). With the clamps 543 and 563 unlocked, the secondary frame 520 is free to move in relation to the anchor delivery sheath control assembly 540 and the secondary steerable catheter control assembly 560. Now, a movement of either the anchor delivery catheter control assembly 550 or the inner catheter control assembly 570 will result in synchronous movement of both the inner catheter 160 and the anchor delivery catheter 140, while the other components of the delivery system 100 remain generally stationary. This synchronous movement of both the inner catheter 160 and the anchor delivery catheter 140 is facilitated by the secondary frame 520. That is, the secondary frame 520 is used to lock the anchor delivery catheter control assembly 550 and the inner catheter control assembly 570 in fixed positions relation to each other.

Referring to FIG. 29A, a schematic depiction of an example catheter system 600 coupled to an example deployment system 700 will now be used to further illustrate the functionality of the deployment frame systems provided herein.

Catheter system 600 includes a plurality of component devices such as catheters 610, 620, 630, 640, 650, and 660 that are slidably coupled with each other as depicted. It should be understood that catheter system 600 is merely an illustrative example, and that the deployment frame systems provided herein can be used with many other types of catheter systems that have other numbers and/or types of component devices.

Deployment system 700 includes a plurality of component devices such as a main frame 710, a secondary frame 720, and couplings 730, 740, 750, 760, 770, and 780. It should be understood that deployment system 700 is merely an illustrative example, and that the deployment frame systems provided herein can, alternately or additionally, be designed to include other types of component devices and to be arranged in different configurations.

Coupling 730 is releasably fixed to catheter 660 and main frame 710 (but not to secondary frame 720). Coupling 740 is releasably fixed to catheter 650, to main frame 710, and to secondary frame 720. Coupling 750 is releasably fixed to catheter 640, to main frame 710, and to secondary frame 720. Coupling 760 is releasably fixed to catheter 630, to main frame 710, and to secondary frame 720. Coupling 770 is releasably fixed to catheter 620, to main frame 710, and to secondary frame 720. Coupling 780 is releasably fixed to catheter 610 and main frame 710 (but not to secondary frame 720).

In the schematic depiction, a circle containing an "x" indicates that the respective coupling is locked (affixed) to the respective other component. In contrast, an open circle indicates that the respective coupling is not locked (not affixed) to the respective other component (i.e., the respective coupling and respective other coupling are free to move in relation to each other). In FIG. 29A, each of the couplings 730, 740, 750, 760, 770, and 780 is locked with one catheter 660, 650, 640, 630, 620, and 610 (respectively). In addition, each of the couplings 730, 740, 750, 760, 770, and 780 is locked with the main frame 710. Lastly, couplings 740, 750, 760, and 770 are also locked with the secondary frame 720.

Referring also to FIG. 29B, in a first example the deployment system 700 can be configured to facilitate movement of a single coupling/catheter. In this example, coupling 740 and catheter 650 are depicted as undergoing a proximal translational movement. To facilitate this movement, coupling 740 is unlocked from each of the main frame 710 and the secondary frame 720. Hence, the coupling 740 (and the catheter 650 to which the coupling 740 is affixed) are free to move relative to the main frame 710 and to the secondary frame 720. Arrows 651 and 741 represent the proximal movements of the catheter 650 and the coupling 740 respectively. It can be seen that the main frame 710 and the secondary frame 720 are stationary, while the catheter 650 and the coupling 740 move proximally in relation to the main frame 710 and the secondary frame 720. All of the other couplings and catheters (other than the catheter 650 and the coupling 740) are also stationary, while the catheter 650 and the coupling 740 move proximally in relation to all of the other couplings and catheters. It should be understood that this illustrative example can be extrapolated such that movements of one or more of the other couplings/catheters can be activated and controlled.

Referring to FIG. 30A, the catheter system 600 and the deployment system 700 are configured in another arrangement. As with the arrangement of FIG. 29A, each of the couplings 730, 740, 750, 760, 770, and 780 is locked with one catheter 660, 650, 640, 630, 620, and 610 (respectively). In addition, each of the couplings 730, 740, 750, 760, 770, and 780 is locked with the main frame 710. Lastly, couplings 740, 750, 760, and 770 are also locked with the secondary frame 720.

Referring also to FIG. 30B, in a second example the deployment system 700 can be configured to facilitate the synchronous movement of a grouping of two couplings/catheters. In this example, the following components are depicted as undergoing a distal translational movement: (i) coupling 750 and catheter 640, (ii) coupling 770 and catheter 620, and (iii) secondary frame 720.

To facilitate the aforementioned movements, the following couplings are unlocked from a respective component: (a) coupling 740 is unlocked from the secondary frame 720, (b) coupling 750 is unlocked from the main frame 710, (c) coupling 760 is unlocked from the secondary frame 720, and (d) coupling 770 is unlocked from the main frame 710. Hence, couplings 750 and 770 are free to move relative to the main frame 710, and the secondary frame 720 is free to move relative to couplings 740 and 760.

As either one (or both) of couplings 750 and 770 are translated distally (such as by a manual force exerted by a clinician), all of the following components will undergo a distal translation: (i) coupling 750 and catheter 640, (ii) coupling 770 and catheter 620, and (iii) secondary frame 720. In this arrangement, the secondary frame 720 effectively becomes a rigid mechanical linkage that interlocks couplings 750 and 770 together, while being free to move relative to the other couplings 740, 760, and 780 (which remain stationary along with the main frame 710).

Arrows 751 and 771 represent the distal movements of the couplings 750 and 770 respectively. Arrows 621 and 641 represent the distal movements of the catheters 620 and 640 respectively. Arrow 721 represents the distal movement of the secondary frame 720. It can be seen that the main frame 710 and couplings 740, 760, and 780 are stationary, while the catheters 640 and 620, couplings 750 and 770, and secondary frame 720 move distally in relation thereto. It should be understood that concepts illustrated in this example can be extrapolated to one or more of the other couplings/catheters such that synchronous movements of various other groupings of delivery system components can be activated and controlled.

Referring again to FIGS. 28A-28C, in additional to facilitating distal and/or proximal translational movements of various individual components or groups of components of the delivery system 100, the deployment frame system 500 can facilitate other types of movements of the components of the delivery system 100. For example, the other types of movements of the components of the delivery system 100 may include, but are not limited to: (i) rotations about the longitudinal axis in either direction, (ii) a deflection (e.g., steering or bending) of one or more portions of a component, and (iii) a tensioning or untensioning of control wires.

An example technique for facilitating rotations of a component of the delivery system 100 about its longitudinal axis will now be explained. As seen in FIG. 28C, the proximal portion of the secondary steerable catheter 150 is releasably coupled within a clamp collar 564 of the secondary steerable catheter control assembly 560. The clamp collar 564 is locked and/or unlocked in relation to the proximal portion of the secondary steerable catheter 150 using a pivotable toggle clamp 565. When the clamp collar 564 is locked on the distal portion of the secondary steerable catheter 150 (by actuating pivotable toggle clamp 565 to a locked position), the secondary steerable catheter 150 is prevented by the clamp collar 564 from rotating about its longitudinal axis. However, when the clamp collar 564 is unlocked in relation to the proximal portion of the secondary steerable catheter 150 (by actuating pivotable toggle clamp 565 to an unlocked position), the secondary steerable catheter 150 is free to be rotated about its longitudinal axis. That is, the proximal portion of the secondary steerable catheter 150 is free to be rotated within the clamp collar 564. After actuating a desired rotation of the secondary steerable catheter 150 by rotating the proximal portion of the secondary steerable catheter 150, the pivotable toggle clamp 565 can be actuated to a locked position to rigidly hold the secondary steerable catheter 150 in the desired rotational position.

In another example, the proximal portion of the inner catheter 160 is releasably coupled within a clamp collar 574 of the inner catheter control assembly 570. The clamp collar 574 is locked and/or unlocked in relation to the proximal portion of the inner catheter 160 using a pivotable toggle clamp 575. When the clamp collar 574 is locked on the proximal portion of the inner catheter 160 (by actuating pivotable toggle clamp 575 to a locked position), the inner catheter 160 is prevented by the clamp collar 574 from rotating about its longitudinal axis. However, when the clamp collar 574 is unlocked in relation to the proximal portion of the inner catheter 160 (by actuating pivotable toggle clamp 575 to an unlocked position), the inner catheter 160 is free to be rotated about its longitudinal axis. That is, the distal portion of the inner catheter 160 is free to be rotated within the clamp collar 574. After actuating a desired rotation of the inner catheter 160 by rotating the proximal portion of the inner catheter 160, the pivotable toggle clamp 575 can be actuated to a locked position to rigidly hold the inner catheter 160 in the desired rotational position.

In some embodiments, such as the depicted embodiment, one or more (or all, in some embodiments) of the other components of the delivery system 100 can be rotationally positioned as desired using the techniques described above in relation to the secondary steerable catheter 150 and the inner catheter 160. For example, in the depicted embodiment the guide catheter 120, the anchor delivery sheath 130, and the anchor delivery catheter 140 can be rotationally positioned as desired using the techniques described above in relation to the secondary steerable catheter 150 and the inner catheter 160. In the depicted embodiment, the guidewire control assembly 580 is configured differently than the other control assemblies, nevertheless, the guidewire control assembly 580 includes a clamp that can be released to allow for a rotation of the guidewire 110 about its longitudinal axis if so desired.

Still referring to FIGS. 28A-28C, the deployment frame system 500 can also facilitate a deflection (e.g., a steering or bending) of one or more portions of a component of the delivery system 100. For example, as described above in reference to FIG. 3, the secondary steerable catheter 150 is articulable to facilitate orientation of the anchor assembly 200 in relation to the mitral valve 17 as desired. That is, in some embodiments (such as the depicted embodiment) the secondary steerable catheter 150 (and/or other components of the delivery system 100) has one or more deflection zones at a distal end portion of the secondary steerable catheter 150. For example, in the depicted embodiment the secondary steerable catheter 150 has two deflection zones 152 and 154 (refer to FIG. 5) at the distal end portion of the secondary steerable catheter 150. In the depicted embodiment, the two deflection zones 152 and 154 allow for deflection of the distal end portion of the secondary steerable catheter 150 within two separate and distinct planes.

The secondary steerable catheter control assembly 560 is configured to actuate deflection motions within the two deflection zones 152 and 154 of the secondary steerable catheter 150. That is, as seen in FIG. 28C, the secondary steerable catheter control assembly 560 a first deflection actuator 566 and a second deflection actuator 567. By turning the knobs of the first deflection actuator 566 and the second deflection actuator 567, the deflection motions within the two deflection zones 152 and 154 of the secondary steerable catheter 150 can be actuated and controlled. In general, each of the deflection zones 152 and 154 includes a collar to which two wires are attached. The two wires are disposed about 180° apart from each other on the collar. The wires run through lumens in the wall of the secondary steerable catheter 150 from the collar to the first deflection actuator 566 or the second deflection actuator 567. A rotation of the deflection actuators 566 and 567 tensions one of the wires and relaxes the other wire. Hence, the deflection can be actuated and controlled.

While in the depicted embodiment the two deflection zones 152 and 154 are generally orthogonal to each other, in some embodiments the two deflection zones 152 and 154 are oriented at angles other than 90° to each other (e.g., about 70°-90°, or about 60°-80°, or about 50°-70°, or about 40°-60°, or less than about 40°).

In the depicted embodiment, the guide catheter control assembly 530 is also configured with a deflection actuator 536 to actuate a deflection of the guide catheter 102. The guide catheter control assembly 530 also includes a deflection plane orientation indicator 537. It should be understood that any of the components of the delivery system 100 can be configured to be steerable.

The deployment frame system 500 can also facilitate a tensioning or untensioning of control wires 142a and 142b (such as to control the radial expansion of the anchor assembly 200 as described above in reference to FIGS. 3 and 4). Further description of tensioning or untensioning of control wires is provided below in reference to FIG. 31.

Still referring to FIGS. 28A-28C, the proximal ends of the catheters and sheaths of the delivery system 100 may include a seal. For example, as seen in FIG. 28C, the proximal end of the secondary steerable catheter 150 has a seal 568. The seal 568 functions to inhibit or prevent fluids from exiting the catheter or sheath, and to inhibit or prevent air ingress into the catheter or sheath. In some embodiments, one or more of the seals may be adjustable to provide varying amounts of sealing pressure.

In the depicted embodiment, the proximal end of the guide catheter 120 also includes a flexible zone 538. The flexible zone 538 can be used to temporarily clamp (e.g., with a hemostat device and the like) the guide catheter 120 substantially closed during and after the removal one or more of the catheters or sheaths from within the guide catheter 120. This feature may be beneficial, for example, when changing over from the deployment frame system 500 to the deployment frame system 700 (as described further below) to substantially maintain a seal of guide catheter 120.

The proximal ends of the catheters and sheaths of the delivery system 100 may also include one or more flushing ports. For example, as seen in FIG. 28C, the proximal end of the secondary steerable catheter 150 has a flushing port 569, and the proximal end of the inner catheter 160 has a flushing port 579. Such flushing ports facilitate liquid flushing of the respective catheter or sheath so as to substantially eliminate air from within the catheter or sheath. In some embodiments, one or more of the seals may be adjustable to provide varying amounts of sealing pressure.

In some embodiments, at least one (or both) of the main frame 510 and the secondary frame 520 include visual indicators thereon. For example, as seen in FIG. 28C, in the depicted embodiment the main frame 510 has a series of hash marks that serve as a linear scale to assist the clinician with having an understanding of the relative positions of the components of deployment system 100 and of the movements made thereto. In some embodiments, other types of visual indicators are included such as, but not limited to, dial gauges, digital gauges, numerical scales, indicator lights, labels, color codes, and the like.

Figure 31:
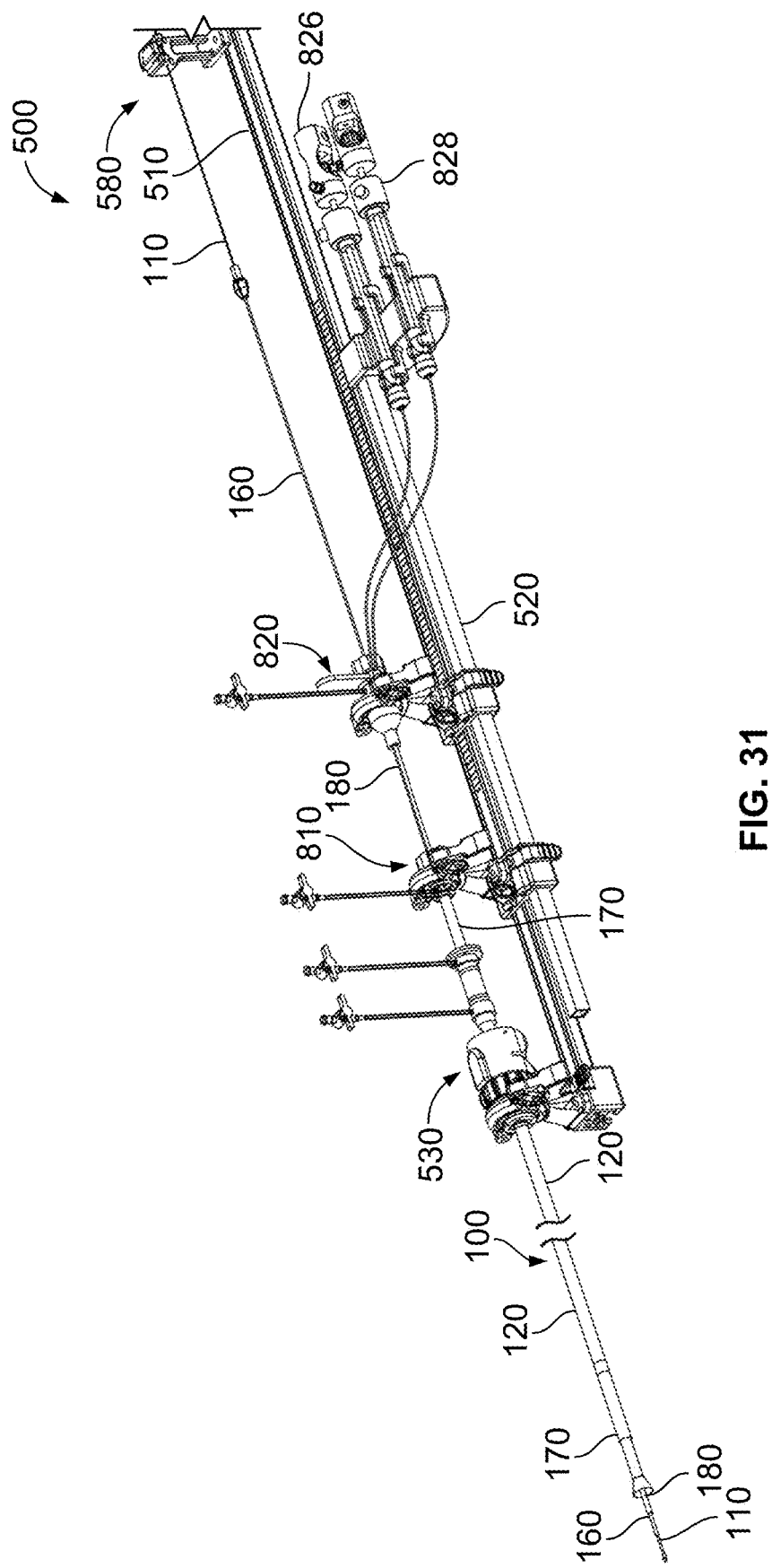
FIG. 31 shows a perspective view of another example deployment frame system configuration in accordance with some embodiments.

Referring to FIG. 31, after the deployment of the anchor assembly 200 (as described above in reference to FIGS. 1-7 and 13A-14B), the example deployment frame system 500 can be configured to deploy a prosthetic mitral valve assembly 300 (refer to FIGS. 15-26) using the transcatheter delivery system 100. While the depicted deployment frame system 500 is configured for deploying the valve assembly 300, it should be understood that this context is one illustrative example of how the inventive concepts provided herein can be implemented. That is, the inventive concepts described in the context of deployment frame system 500 can be adapted and implemented for the percutaneous deployment of many other types of prosthetic implants, medical devices, and the like.

In the depicted configuration (which is arranged for deploying the valve assembly 300), deployment frame system 500 includes the main frame 510, the secondary frame 520, the guide catheter control assembly 530, the guidewire control assembly 580, a valve delivery sheath control assembly 810, a valve delivery catheter control assembly 820, a first control wire handle 826, and a second control wire handle 828.

In some implementations, after the deployment of the anchor assembly 200 using the deployment frame system 500 in the configuration of FIGS. 28A-28C, the deployment frame system 500 can be reconfigured to the configuration of the deployment frame system 500 as shown in FIG. 31 for the deployment of the valve assembly 300. In some example implementations, the steps for reconfiguring the deployment frame system 500 from the anchor deployment configuration to the valve deployment configuration are as follows. Referring also to FIG. 28A, the clamp collars of the anchor delivery sheath control assembly 540, the anchor delivery catheter control assembly 550, the secondary steerable catheter control assembly 560, the inner catheter control assembly 570, and the guidewire control assembly 580 can be opened. Then, the anchor delivery sheath 130, the anchor delivery catheter 140, and the secondary steerable catheter 150 can be pulled back from engagement with the other members of the deployment system 100 (while leaving the guide catheter 120, inner catheter 160 and guidewire 110 in place). Next the valve delivery sheath 170 (containing the valve assembly 300 in some implementations) and the valve delivery catheter 180 can be installed within the guide catheter 120 and over the inner catheter 160. The valve delivery sheath control assembly 810 and the valve delivery catheter control assembly 820 can then be clamped to the main frame 510 and the secondary frame 520 as shown in FIG. 31. In some implementations, the inner catheter 160 is allowed to float on the guidewire 110 (i.e., in some embodiments no inner catheter control assembly is used, as shown in FIG. 31). In some implementations of the deployment frame system 500 for deployment of the anchor assembly 200, the inner catheter 160 is allowed to float on the guidewire 110.

In the depicted embodiment, the valve delivery catheter control assembly 820 is coupled with the first control wire handle 826, and the second control wire handle 828. The first control wire handle 826 and the second control wire handle 828 can be used to actuate and control the control wires the one or more control wires of the valve delivery catheter 180. For example, as described in reference to FIG. 19, in some embodiments the valve delivery catheter 180 includes a first control wire that restrains the proximal end portion of the valve assembly 300, and a second control wire that restrains the distal end portion of the valve assembly 300. As tension on the first control wire is released, the proximal end portion of the valve assembly 300 is allowed to radially expand. Similarly, as tension on the second control wire is released, the distal end portion of the valve assembly 300 is allowed to radially expand. The first control wire handle 826 and the second control wire handle 828 can be used by the clinician to actuate and control the expansions of the portions of the valve assembly 300 sequentially, concurrently, or partially concurrently. Such control wire handles 826 and 828 may also be included in the anchor assembly deployment configuration of the deployment frame system 500 (refer to FIGS. 28A-28C) for control of the control wires 142a and 142b.

Figure 32:
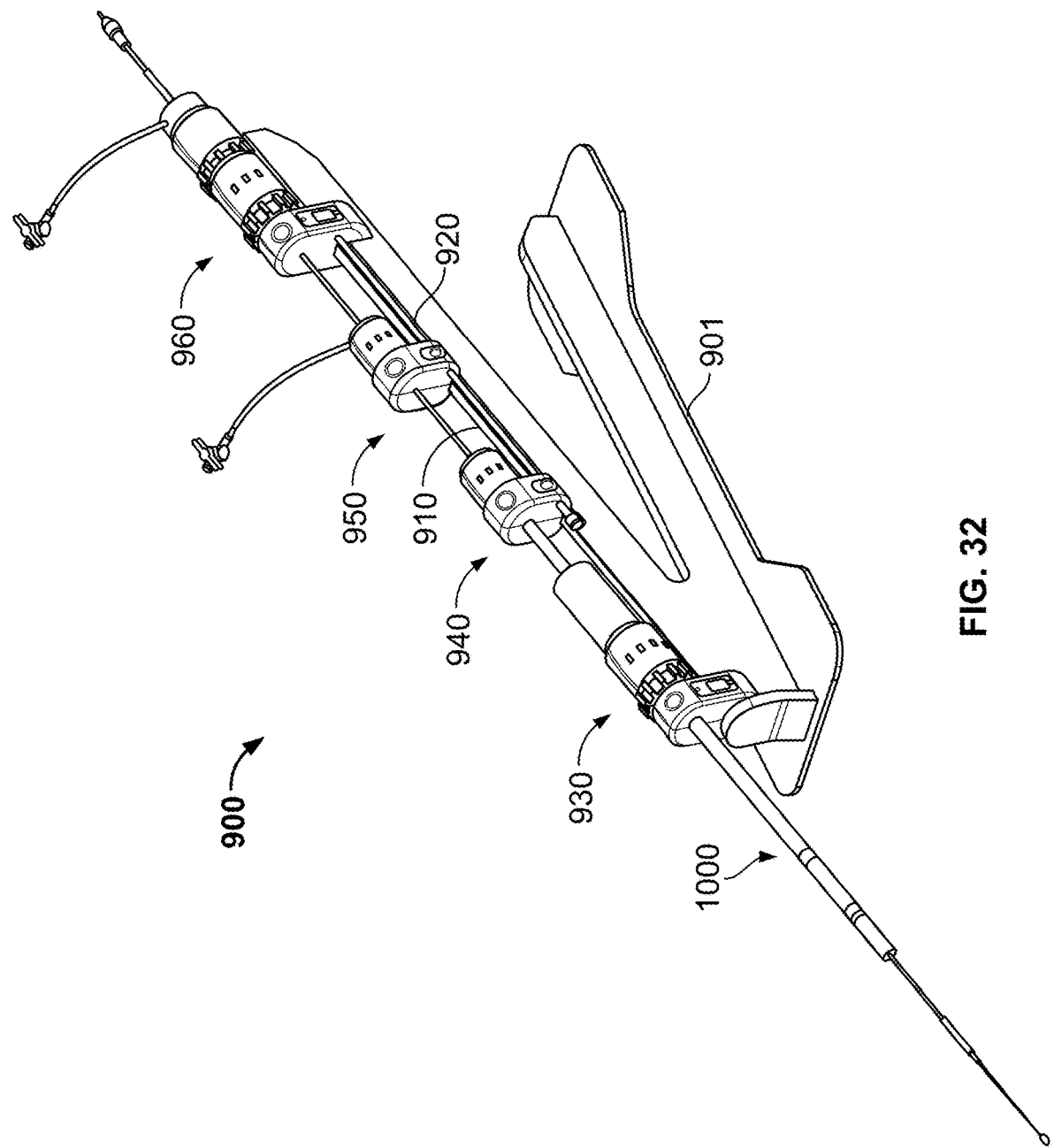
FIG. 32 shows a perspective view of another example deployment frame system configuration in accordance with some embodiments.
Figure 33:
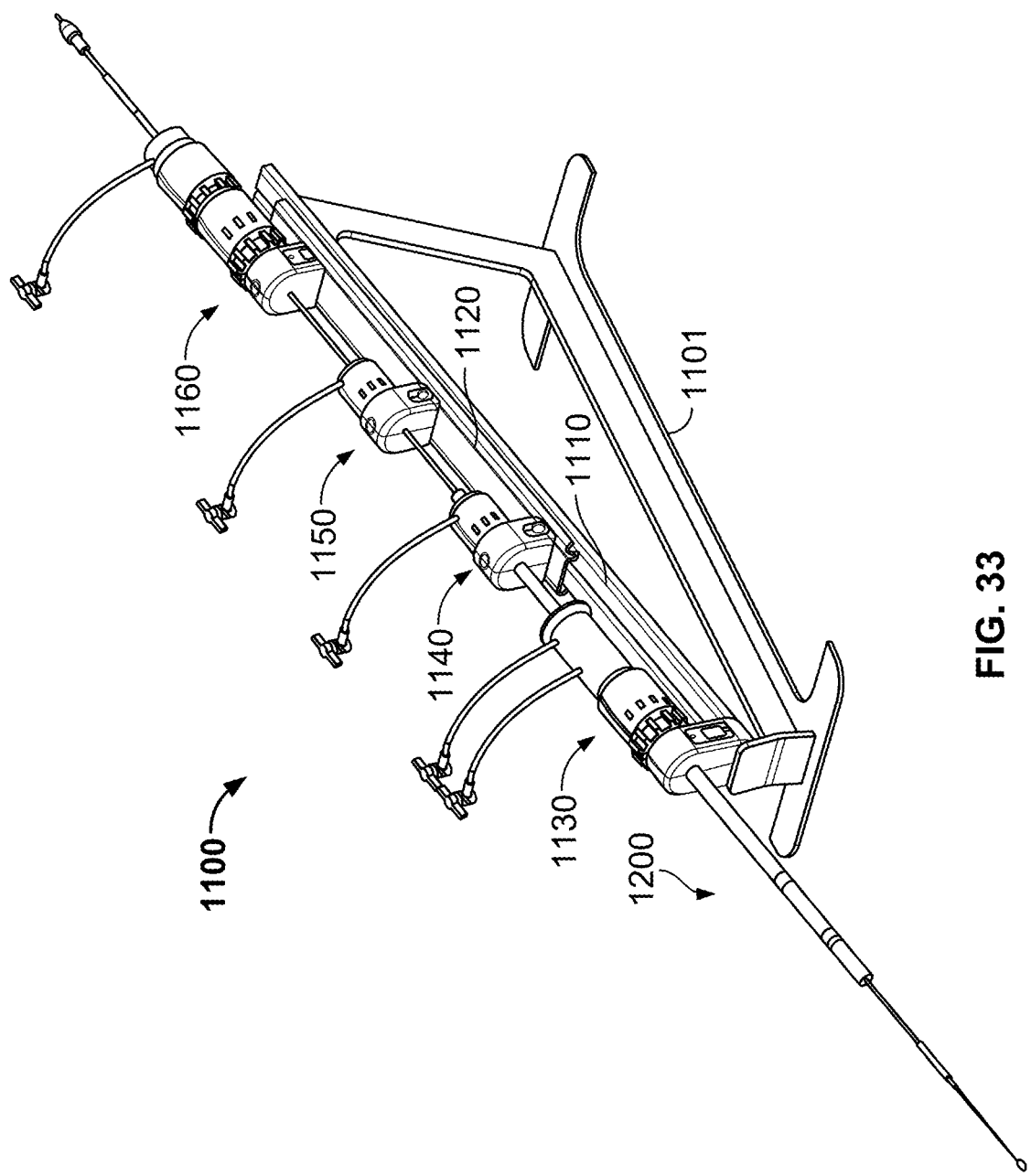
FIG. 33 shows a perspective view of another example deployment frame system configuration in accordance with some embodiments.
Figure 34:
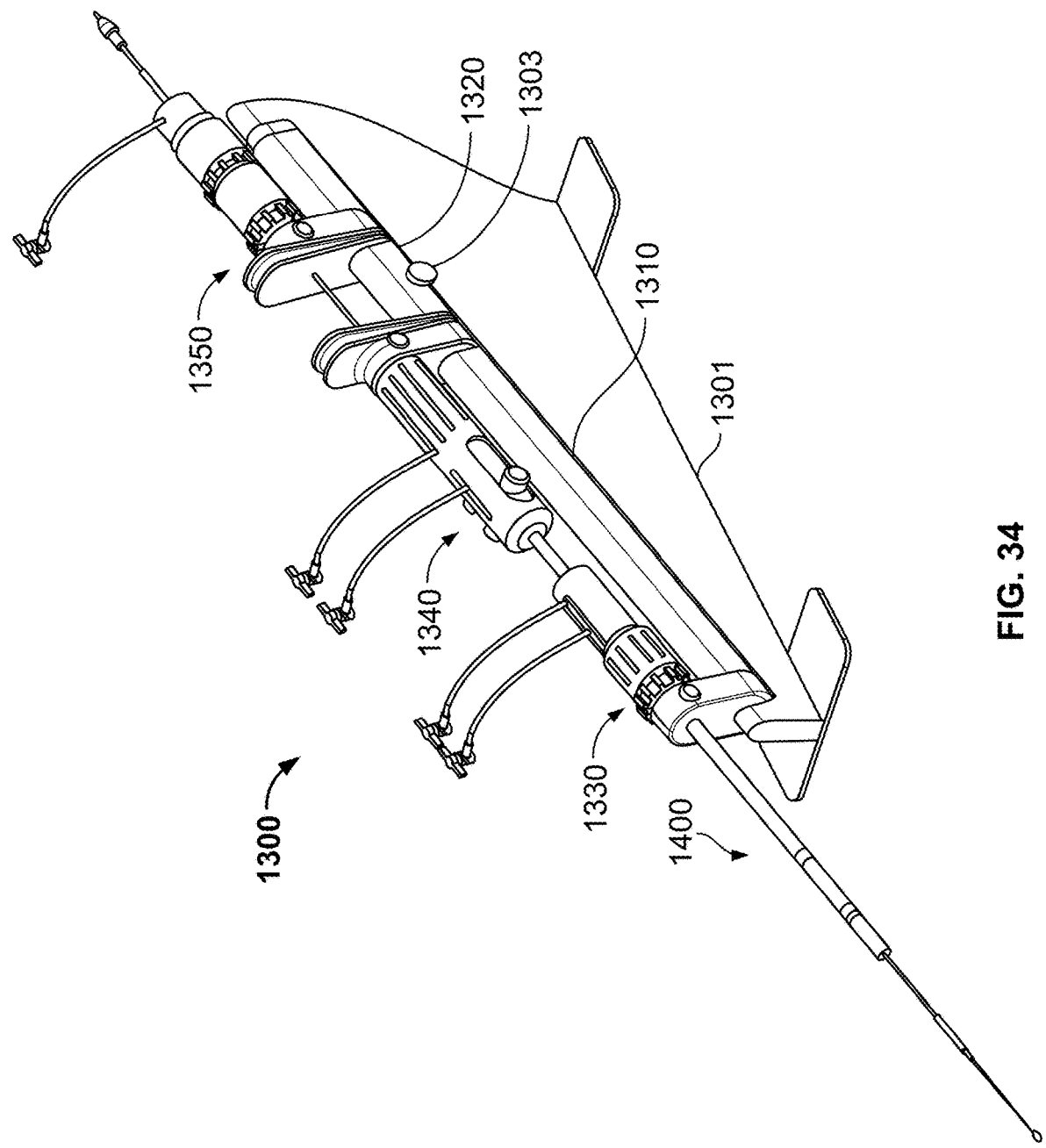
FIG. 34 shows a perspective view of another example deployment frame system configuration in accordance with some embodiments.

Referring to FIGS. 32-34, additional example embodiments of deployment frame systems are depicted. It should be understood that one or more features of one example deployment frame system described herein can be combined with one or more features of one or more other example deployment frame systems described herein. Accordingly, deployment frame system hybrid designs can be created which are entirely within the scope of this disclosure.

FIG. 32 depicts an example deployment frame system 900 that is shown in conjunction with an example catheter system 1000. The deployment frame system 900 includes a main frame 910, a secondary frame 920, and catheter control assemblies 930, 940, 950, and 960. The catheter control assembly 930 is longitudinally slidable in relation to the main frame 910. The catheter control assemblies 940, 950, and 960 are longitudinally slidable in relation to the main frame 910 and the secondary frame 920. The catheter control assemblies 930, 940, 950, and 960 are each individually releasably lockable to the main frame 910. The catheter control assemblies 940, 950, and 960 are each individually releasably lockable to the secondary frame 920. In the depicted embodiment, the deployment frame system 900 includes a support structure 901 which orients the main frame 910 and the secondary frame 920 at an acute angle in relation to horizontal. In some embodiments, the acute angle is selectively adjustable.

FIG. 33 depicts another example deployment frame system 1100 that is shown in conjunction with an example catheter system 1200. The deployment frame system 1100 includes a main frame 1110, a secondary frame 1120, and catheter control assemblies 1130, 1140, 1150, and 1160. The catheter control assembly 1130 is longitudinally slidable in relation to the main frame 1110. In some embodiments, the catheter control assemblies 1140, 1150, and 1160 are longitudinally slidable in relation to the main frame 1110 and the secondary frame 1120. In some embodiments, the catheter control assemblies 1130, 1140, 1150, and 1160 are each individually releasably lockable to the main frame 1110. The catheter control assemblies 1140, 1150, and 1160 are each individually releasably lockable to the secondary frame 1120. In the depicted embodiment, the deployment frame system 1100 includes a support structure 1101 which orients the main frame 1110 and the secondary frame 1120 at an acute angle in relation to horizontal. In some embodiments, the acute angle is selectively adjustable.

In the depicted embodiment of the deployment frame system 1100, the secondary frame 1120 is slidably disposed on top of a portion of the main frame 1110. Hence, in this embodiment the main and secondary frames are not spaced apart, horizontally side-by-side as in some other deployment frame system embodiments described herein. In some embodiments, the arrangement of the deployment frame system 1100 with the secondary frame 1120 slidably disposed on top of a portion of the main frame 1110 may provide for a more compact configuration than some spaced apart, horizontally side-by-side deployment frame system configurations.

FIG. 34 depicts another example deployment frame system 1300 that is shown in conjunction with an example catheter system 1400. The deployment frame system 1300 includes a main frame 1310, a secondary frame 1320, and catheter control assemblies 1330, 1340, and 1350. In this embodiment, the control assemblies of two catheters are combined into the single catheter control assembly 1340. The catheter control assembly 1330 is longitudinally slidable in relation to the main frame 1310. In some embodiments, the catheter control assemblies 1340 and 1350 are longitudinally slidable in relation to the main frame 1310 and the secondary frame 1320. In some embodiments, the catheter control assemblies 1330, 1340, and 1350 are each individually releasably lockable to the main frame 1310. In some embodiments, the catheter control assemblies 1340 and 1350 are each individually releasably lockable to the secondary frame 1320. In the depicted embodiment, the deployment frame system 1300 includes a support structure 1301 which orients the main frame 1310 and the secondary frame 1320 at an acute angle in relation to horizontal. In some embodiments, the acute angle is selectively adjustable.

In the depicted embodiment of the deployment frame system 1300, the secondary frame 1320 is slidably disposed on top of a portion of the main frame 1310. Hence, in this embodiment the main and secondary frames are not spaced apart, horizontally side-by-side as in some other deployment frame system embodiments described herein. In some embodiments, the arrangement of the deployment frame system 1300 with the secondary frame 1320 slidably disposed on top of a portion of the main frame 1310 may provide for a more compact configuration than some spaced apart, horizontally side-by-side deployment frame system configurations. In the depicted embodiment, a locking device 1303 is included that can releasably lock the secondary frame 1320 and the main frame 1310 together.

Figure 35:
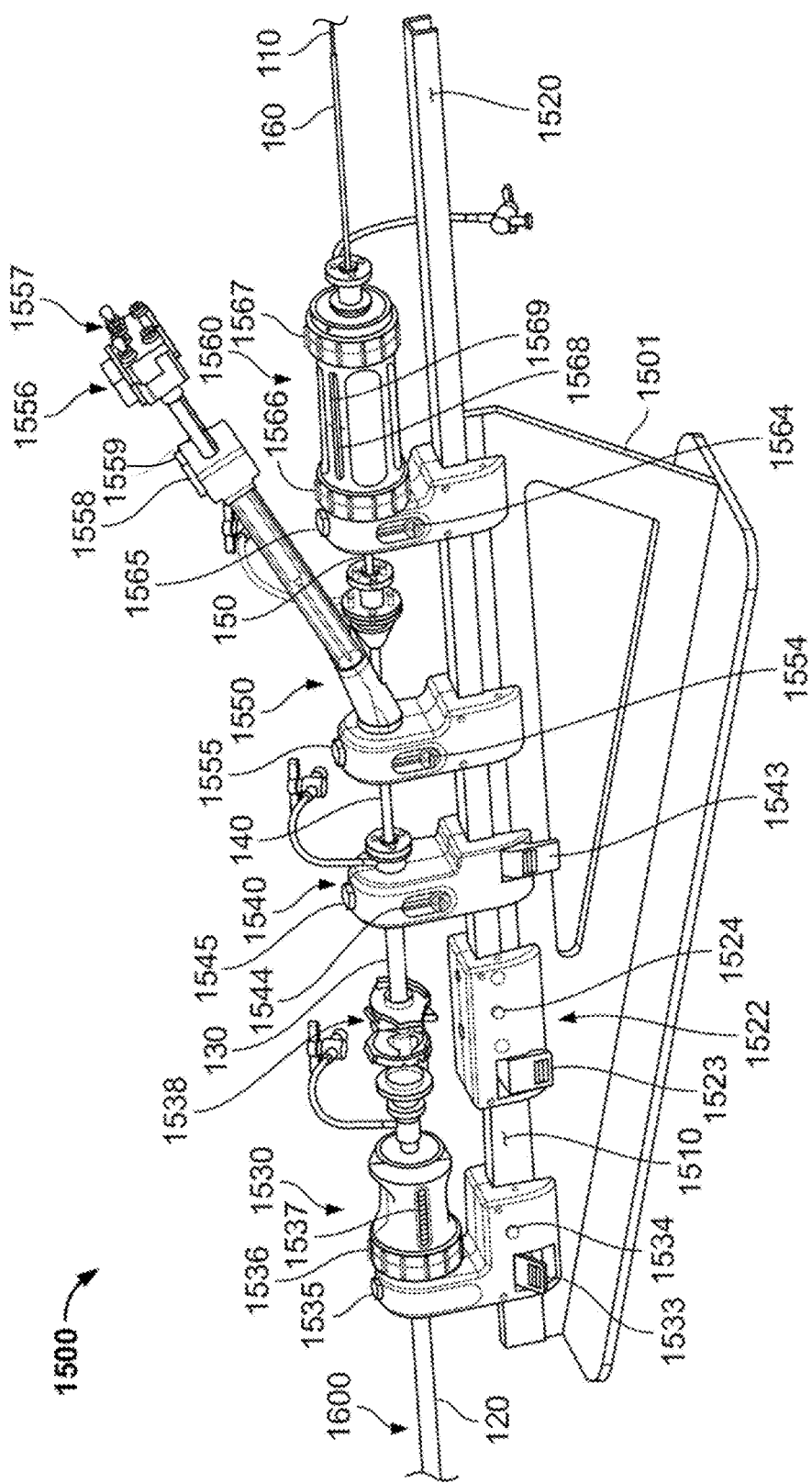
FIG. 35 shows a perspective view of another example deployment frame system configuration in accordance with some embodiments.

FIG. 35 depicts another example deployment frame system 1500. The deployment frame system 1500 is shown in conjunction with an example catheter system 1600. In the depicted embodiment, the deployment frame system 1500 is configured to be able to percutaneously deploy a device such as the anchor assembly 200 described above. In such a case, the catheter system 1600 can be configured like the delivery system 100 described above (i.e., a guidewire 110, a guide catheter 120, an anchor delivery sheath 130, an anchor delivery catheter 140, a secondary steerable catheter 150, and an inner catheter 160).

In the depicted configuration, the deployment frame system 1500 includes a main frame 1510, a secondary frame 1520, and a support structure 1501. The main frame 1510 can be releasably coupled to the support structure 1501. That is, in some embodiments the main frame 1510 can be detached from the support structure 1501. In some such embodiments, the main frame 1510 is a single-use component, while the support structure 1501 is a sterilizable, reusable component. While in use, the main frame 1510 remains stationary in relation to the support structure 1501. In some embodiments, the main frame 1510 is a portion of the support structure 1501.

In the depicted embodiment, the secondary frame 1520 is an inverted u-channel that is slidably coupled directly on the main frame 1510. Other arrangements can also be used (e.g., side-by-side, etc.). The secondary frame 1520 can be selectively longitudinally translated (proximally and distally) in relation to the main frame 1510. In the depicted embodiment, the secondary frame 1520 includes a frame clamp assembly 1522 disposed at a distal end of the second frame 1520. The frame clamp assembly 1522 is releasably clampable at any position along the main frame 1510. That is, the frame clamp assembly 1522 is slidable along the main frame 1510 (along with the rest of the secondary frame 1520) while the frame clamp assembly 1522 is unclamped from the main frame 1510, and the frame clamp assembly 1522 will be held stationary in relation to the main frame 1510 while the frame clamp assembly 1522 is clamped to the main frame 1510. In the depicted embodiment, a pivotable toggle clamp 1523 is used to manually clamp and unclamp the frame clamp assembly 1522 (and the secondary frame 1520 as a whole)

to the main frame 1510. With toggle clamp 1523 unclamped, the secondary frame 1520 is free to translate proximally and distally in relation to the main frame 1510.

In the depicted embodiment, the frame clamp assembly 1522 also includes a latch mechanism 1524. The latch mechanism 1524 can be manually actuated to facilitate the complete detachment of the secondary frame 1520 from the main frame 1510. In other words, when the latch mechanism 1524 is actuated (e.g., the button(s) is/are pressed) the secondary frame 1520 can be separated from its engagement with the main frame 1510. This functionality can be advantageous, for example, when converting from the arrangement of FIG. 35 to the arrangement of FIG. 36, as described further below. The latch mechanism 1524 can be spring-biased such that its default arrangement (i.e., while unactuated) is to be latched to the main frame 1510.

The deployment frame system 1500 also includes a guide catheter control assembly 1530, an anchor delivery sheath control assembly 1540, an anchor delivery catheter control assembly 1550, and a secondary steerable catheter control assembly 1560. The guide catheter 120 extends through the guide catheter control assembly 1530 and terminates at a guide catheter seal device 1538. A proximal end of the anchor delivery sheath 130 is terminated at the anchor delivery sheath control assembly 1540. A proximal end of the anchor delivery catheter 140 is terminated at the anchor delivery catheter control assembly 1550. A proximal end of the secondary steerable catheter 150 is terminated at the secondary steerable catheter control assembly 1560.

In the depicted embodiment, the proximal end of the inner catheter 160 is "floating" on the guidewire 110. That is, the inner catheter 160 and guidewire 110 are not terminated at a control assembly that is coupled to the main frame 1510 or the secondary frame 1520. In some embodiments, control assemblies for one or both of the inner catheter 160 and guidewire 110 are included such that the inner catheter 160 and/or guidewire 110 are terminated at a control assembly that is coupled to the main frame 1510, or the secondary frame 1520, or both.

The guide catheter control assembly 1530 is releasably clampable to the main frame 1510. A pivotable toggle clamp 1533 is actuatable whereby the guide catheter control assembly 1530 can be selectively clamped and unclamped in relation to the main frame 1510. While the toggle clamp 1533 is oriented such that the guide catheter control assembly 1530 is unclamped in relation to the main frame 1510, the guide catheter control assembly 1530 can be translated distally and proximally along the longitudinal axis of the main frame 1510. While the toggle clamp 1533 is oriented such that the guide catheter control assembly 1530 is clamped in relation to the main frame 1510, the guide catheter control assembly 1530 is detained from being translated distally and proximally along the longitudinal axis of the main frame 1510.

In the depicted embodiment, the guide catheter control assembly 1530 also includes a latch mechanism 1534. The latch mechanism 1534 can be manually actuated to facilitate the detachment of the guide catheter control assembly 1530 from the main frame 1510. In other words, when the latch mechanism 1534 is actuated (e.g., the button(s) is/are pressed) the guide catheter control assembly 1530 can be separated from its engagement with the main frame 1510. The latch mechanism 1534 can be spring-biased such that its default arrangement (i.e., while unactuated) is to be latched to the main frame 1510.

In the depicted embodiment, the anchor delivery sheath control assembly 1540 is releasably clampable to the main frame 1510 and to the secondary frame 1520. A pivotable toggle clamp 1543 is actuatable whereby the anchor delivery sheath control assembly 1540 can be selectively clamped and unclamped in relation to the main frame 1510. In addition, the anchor delivery sheath control assembly 1540 includes a latch mechanism 1544. The latch mechanism 1544 is actuatable such that the anchor delivery sheath control assembly 1540 can be selectively clamped and unclamped in relation to the secondary frame 1520. In the depicted arrangement, the latch mechanism 1544 is in the clamped position. By sliding the knob of the latch mechanism 1544 upward (i.e., away from the secondary frame 1520), the anchor delivery sheath control assembly 1540 will become unclamped from the secondary frame 1520.

In the depicted embodiment, the anchor delivery catheter control assembly 1550 is releasably clampable to the secondary frame 1520. However, in the depicted embodiment the anchor delivery catheter control assembly 1550 is not clampable to the main frame 1510. In some embodiments, the anchor delivery catheter control assembly 1550 is releasably clampable to the main frame 1510. The anchor delivery catheter control assembly 1550 includes a latch mechanism 1554. The latch mechanism 1554 is actuatable such that the anchor delivery catheter control assembly 1550 can be selectively clamped and unclamped in relation to the secondary frame 1520. In the depicted arrangement, the latch mechanism 1554 is in the clamped position. By sliding the knob of the latch mechanism 1554 away from the secondary frame 1520, the anchor delivery catheter control assembly 1550 will become unclamped from the secondary frame 1520 such that the anchor delivery catheter control assembly 1550 can be translated proximally and distally along the axes of the main frame 1510 and the secondary frame 1520.

In the depicted embodiment, the secondary steerable catheter control assembly 1560 is releasably clampable to the secondary frame 1520. However, in the depicted embodiment the secondary steerable catheter control assembly 1560 is not clampable to the main frame 1510. In some embodiments, the secondary steerable catheter control assembly 1560 is releasably clampable to the main frame 1510. The secondary steerable catheter control assembly 1560 includes a latch mechanism 1564. The latch mechanism 1564 is actuatable such that the secondary steerable catheter control assembly 1560 can be selectively clamped and unclamped in relation to the secondary frame 1520. In the depicted arrangement, the latch mechanism 1564 is in the clamped position. By sliding the knob of the latch mechanism 1564 away from the secondary frame 1520, the secondary steerable catheter control assembly 1560 will become unclamped from the secondary frame 1520 such that the secondary steerable catheter control assembly 1560 can be translated proximally and distally along the axes of the main frame 1510 and the secondary frame 1520.

As described above, such as in reference to FIGS. 29A-30B, the toggle clamps 1533, 1523, and 1543 and the latch mechanisms 1544, 1554, and 1564 can be selectively clamped and/or unclamped to facilitate longitudinal translations in the proximal and distal directions of a single one of the guide catheter control assembly 1530, the anchor delivery sheath control assembly 1540, the anchor delivery catheter control assembly 1550, or the secondary steerable catheter control assembly 1560, or of multiple ones of the guide catheter control assembly 1530, the anchor delivery sheath control assembly 1540, the anchor delivery catheter control assembly 1550, and the secondary steerable catheter control assembly 1560 synchronously. In one example of synchronous translation, while the toggle clamps 1523 and 1543 are unclamped and the toggle clamp 1533 and the latch mechanisms 1544, 1554, and 1564 are clamped, the anchor delivery sheath control assembly 1540, the anchor delivery catheter control assembly 1550, and the secondary steerable catheter control assembly 1560 can be synchronously translated proximally and distally by sliding the secondary frame 1520 along the main frame 1510.

In the depicted embodiment of the deployment frame system 1500, each of the catheter control assemblies 1530, 1540, 1550, and 1560 can be individually selectively actuated to allow rotation of the catheter that is terminated at the respective control assembly 1530, 1540, 1550, or 1560. For example, the guide catheter control assembly 1530 includes a latch mechanism 1535 that can be manually actuated to allow the guide catheter 120 to be manually rotated about its longitudinal axis while the other components of the catheter system 1600 are held stationary by latch mechanisms 1545, 1555, and 1565 such that they do not rotate. In the depicted embodiment, the latch mechanism 1535 includes a button that can be depressed to unlatch the guide catheter 120 so it can be rotated. The button of the latch mechanism 1535 can be spring-biased to the latched configuration such that releasing the button latches the guide catheter 120 to prevent its rotation. The other latch mechanisms 1545, 1555, and 1565 can function analogously to that of the latch mechanism 1535.

As described above, some components of the catheter systems described herein can include one or more deflection zones that are controllably deflectable. For example, the distal end portion of the guide catheter 120 can be deflected to navigate the patient's anatomy and/or to be positioned in relation to the patient's anatomy as desired. Additionally, the secondary steerable catheter 150 has two deflection zones 152 and 154 (refer to FIG. 5) at the distal end portion of the secondary steerable catheter 150. In some embodiments, the two deflection zones 152 and 154 allow for deflection of the distal end portion of the secondary steerable catheter 150 within two separate and distinct planes.

The deployment frame system 1500 is also configured to allow a clinician to controllably deflect some components of the catheter system 1600. For example, the guide catheter control assembly 1530 includes a rotary deflection actuator 1536 that can be manually rotated to control the deflection of the distal end portion of the guide catheter 120. Additionally, the secondary steerable catheter control assembly 1560 includes a first deflection actuator 1566 and a second rotary deflection actuator 1567 that can be manually rotated to control the deflection of the deflection zones 152 and 154 at the distal end portion of the secondary steerable catheter 150.

In some embodiments, catheter control assemblies that include one or more rotary deflection actuators (e.g., catheter control assemblies 1530 and 1560) can include visual indicators to provide clinicians with a visual indication of how much the respective catheter is deflected. For example, the guide catheter control assembly 1530 includes a deflection indicator 1537. The deflection indicator 1537 includes a window and a translating marker that act together like a gauge to provide a visual indication of how much the guide catheter 120 is deflected. Similarly, the secondary steerable catheter control assembly 1560 includes a first deflection indicator 1568 and a second deflection indicator 1569 that provide a visual indication of how much the deflection zones 152 and 154 at the distal end portion of the secondary steerable catheter 150 are deflected.

The deployment frame system 1500 is also configured to allow a clinician to make adjustments to the tension of the control wires of the catheter system 1600. For example, as described above in reference to FIG. 2, in some embodiments one or more portions of the anchor assembly 200 can be releasably coupled to the anchor delivery catheter 140 by two control wires 142. In one such example, one of the two control wires 142 is releasably coupled with a proximal end of the anchor assembly 200, and a second of the two control wires 142 is releasably coupled with a mid-body portion of the anchor assembly 200. A clinician can separately control the two control wires 142 using a first control wire adjustment assembly 1556 and a second control wire adjustment assembly 1557. In the depicted embodiment, the ends of the control wires 142 are fixedly terminated at the proximal ends of the control wire adjustment assemblies 1556, 1557. Then, to add tension to or to release tension from the control wires 142, the proximal ends of the control wire adjustment assemblies 1556, 1557 can be translated proximally or distally, respectively, in relation to the anchor delivery catheter control assembly 1550. In the depicted embodiment, the control wire adjustment assemblies 1556, 1557 each include a latch mechanism 1558, 1559, respectively. The latch mechanisms 1558, 1559 can be used to detain the proximal ends of the control wire adjustment assemblies 1556, 1557 in a desired orientation in relation to the anchor delivery catheter control assembly 1550 such that the desired tension of the respective control wire is releasably maintained.

Figure 36:
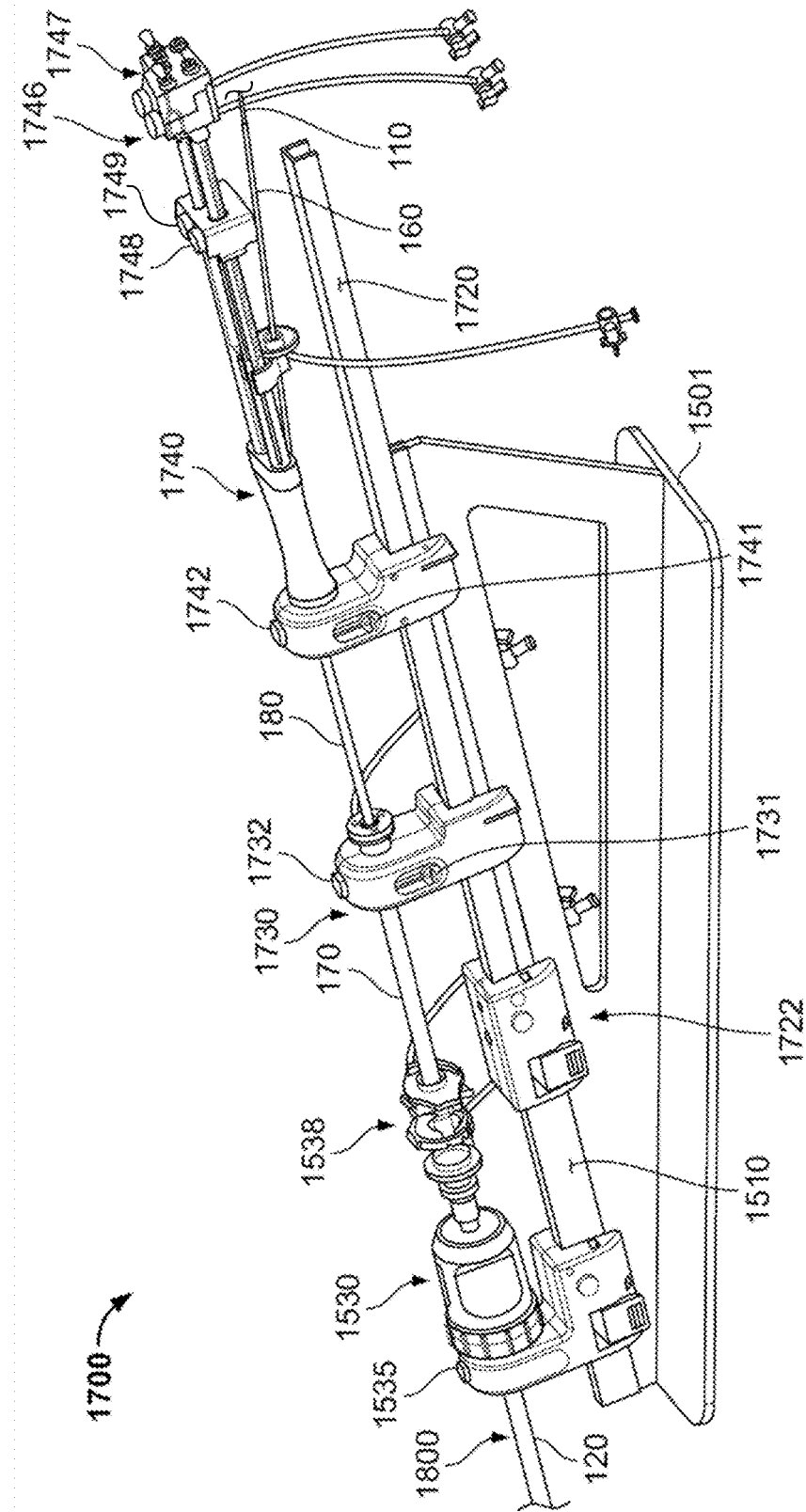
FIG. 36 shows a perspective view of another example deployment frame system configuration in accordance with some embodiments.

FIG. 36 depicts another example deployment frame system 1700. The deployment frame system 1700 is shown in conjunction with an example catheter system 1800. In the depicted embodiment, the deployment frame system 1700 is configured to be able to percutaneously deploy a device such as the valve assembly 300 described above. In such a case, the catheter system 1800 can be configured like the delivery system 100 described above (i.e., a guidewire 110, a guide catheter 120, an inner catheter 160, a valve delivery sheath 170, and a valve delivery catheter 180).

In the depicted configuration, the deployment frame system 1700 includes the main frame 1510 (which may be the same main frame 1510 used for the deployment frame system 1500 described above), a secondary frame 1720, and the support structure 1501 (which may be the same support structure 1501 used for the deployment frame system 1500 described above). A frame clamp assembly 1722 selectively clamps the secondary frame 1720 to the main frame 1510.

To convert from the deployment frame system 1500 (e.g., after the deployment of the anchor assembly 200) to the deployment frame system 1700 (to prepare for the deployment of the valve assembly 300), in some cases a clinician may take the following steps. The toggle clamps 1523 and 1543 can be unclamped from the main frame 1510. The latch mechanism 1524 of the secondary frame clamp assembly 1522 can be actuated to unlatch the secondary frame 1520 from the main frame 1510. With the clamps 1523 and 1543 unclamped, and the latch mechanism 1524 actuated, the secondary frame 1520 (along with the attached catheter control assemblies 1540, 1550, and 1560 and their respective components of the catheter system 1600) can be pulled proximally off of the main frame 1510. The proximal movement of the secondary frame 1520 and its associated components can be continued until the anchor delivery sheath 130, anchor delivery catheter 140, and the secondary steerable catheter 150 have been fully disengaged from the guide catheter 120, the inner catheter 160, and the guidewire 110.

In order to inhibit or substantially prevent fluids from exiting the guide catheter 120 resulting from the removal of anchor delivery sheath 130, anchor delivery catheter 140, and the secondary steerable catheter 150, and/or to inhibit or substantially prevent air ingress into the guide catheter 120 resulting from the removal of anchor delivery sheath 130, anchor delivery catheter 140, and the secondary steerable catheter 150, the guide catheter seal device 1538 can be used to seal the proximal end of the guide catheter 120. Next, the valve delivery sheath 170 (which can be preloaded with the prosthetic valve assembly 300) and the valve delivery catheter 180 can be threaded over the inner catheter 160 and the guidewire 110, and into the guide catheter 120. The secondary frame 1720 can be engaged with the main frame 1510, and a valve delivery sheath control assembly 1730 and a valve delivery catheter control assembly 1740 can be engaged with the secondary frame 1720. The sequence of the actions performed to convert from the arrangement of FIG. 35 to the arrangement of FIG. 36 may be performed in differing orders without departing from the inventive scope of this disclosure.

The deployment frame system 1700 also includes the valve delivery sheath control assembly 1730 and the valve delivery catheter control assembly 1740. The proximal end of the valve delivery sheath 170 is terminated at the valve delivery sheath control assembly 1730. The proximal end of the valve delivery catheter 180 is terminated at the valve delivery catheter control assembly 1740.

In the depicted embodiment, the valve delivery sheath control assembly 1730 and the valve delivery catheter control assembly 1740 are configured similarly in that each is releasably clampable to the secondary frame 1720, but not to the main frame 1510. In particular, the valve delivery sheath control assembly 1730 includes a latch mechanism 1731 and the valve delivery catheter control assembly 1740 includes a latch mechanism 1741. The latch mechanisms 1731 and 1741 releasably clamp the valve delivery sheath control assembly 1730 and the valve delivery catheter control assembly 1740, respectively, at selected locations along the longitudinal axis of the secondary frame 1720. Further, the valve delivery sheath control assembly 1730 includes a latch mechanism 1732 and the valve delivery catheter control assembly 1740 includes a latch mechanism 1742. The latch mechanisms 1732 and 1742 releasably clamp and prevent rotation of the valve delivery sheath 170 and the valve delivery catheter 180, respectively. Manual actuation of the latch mechanism 1732 allows the valve delivery sheath 170 to be manually rotated about its longitudinal axis while the other components of the catheter system 1800 are held stationary by latch mechanisms 1535 and 1742 such that they do not rotate. Similarly, manual actuation of the latch mechanism 1742 allows the valve delivery catheter 180 to be manually rotated about its longitudinal axis while the other components of the catheter system 1800 are held stationary by latch mechanisms 1535 and 1732 such that they do not rotate.

The deployment frame system 1700 is also configured to allow a clinician to make adjustments to the tension of the control wires of the catheter system 1800. For example, as described above in reference to FIG. 18, in some embodiments one or more portions of the valve assembly 300 can be releasably coupled to the valve delivery catheter 180 by control wires. In one such example, one of two control wires is releasably coupled with a proximal end of the valve assembly 300, and a second of the two control wires is releasably coupled with a distal end of the valve assembly 300. A clinician can separately control the two control wires using a first control wire adjustment assembly 1746 and a second control wire adjustment assembly 1747. In the depicted embodiment, the ends of the control wires are fixedly terminated at the proximal ends of the control wire adjustment assemblies 1746, 1747. Then, to add tension to or to release tension from the control wires, the proximal ends of the control wire adjustment assemblies 1746, 1747 can be translated proximally or distally, respectively, in relation to the valve delivery catheter control assembly 1740. In the depicted embodiment, the control wire adjustment assemblies 1746, 1747 each include a latch mechanism 1748, 1749, respectively. The latch mechanisms 1748, 1749 can be used to detain the proximal ends of the control wire adjustment assemblies 1746, 1747 in a desired orientation in relation to the valve delivery catheter control assembly 1740 such that the desired tension of the respective control wire is releasably maintained.

A number of embodiments of the invention have been described. Nevertheless, it will be understood that various modifications may be made without departing from the scope of the invention. Accordingly, other embodiments are within the scope of the following claims.

What is claimed is:

1. A method of implanting a prosthetic mitral valve in a patient, the method comprising:
   inserting, into a patient, a system of multiple catheters configured to deliver the prosthetic mitral valve;
   engaging, to a deployment frame system, the system of multiple catheters, the deployment frame system comprising:
   a plurality of clamps, each clamp of the plurality of clamps configured to releasably clamp a proximal end portion of a respective catheter of the multiple catheters;
   a first frame, wherein each clamp of the plurality of clamps is configured to releasably couple with the first frame;
   a second frame, wherein at least one clamp of the plurality of clamps is configured to releasably couple with the second frame; and
   a frame clamp mechanism configured to clamp the second frame to the first frame at a plurality of relative longitudinal orientations between the first frame and the second frame;
   manipulating the deployment frame system to implant the prosthetic mitral valve in a heart of the patient.

2. The method of claim 1, wherein said manipulating comprises translating the second frame parallel to a longitudinal axis of the first frame.

3. The method of claim 1, wherein said manipulating comprises unclamping a respective one of the clamps from a respective catheter and rotating the respective catheter about a longitudinal axis of the respective catheter.

4. The method of claim 1, wherein at least one of the clamps is configured to releasably clamp onto the first frame and onto the second frame simultaneously.

5. The method of claim 1, wherein at least one of the clamps includes an actuator for deflecting a portion of a respective catheter while the respective catheter is clamped by the clamp.

6. The method of claim 1, wherein at least one of the clamps includes a mechanism for selectively adding and removing tension from one or more control wires.

7. The method of claim 1, wherein said manipulating comprises clamping two or more of the clamps to the second frame and translating said two or more of the clamps along the first frame such that a translational movement of the second frame relative to the first frame simultaneously moves said two or more clamps in relation to the first frame.

8. The method of claim 7, wherein the translational movement of the second frame causes corresponding simultaneous movements of two or more catheters of the multiple catheters.

9. The method of claim 1, wherein implanting the prosthetic mitral valve in the heart of the patient comprises: delivering an anchor assembly of the prosthetic mitral valve to a mitral valve annulus of the heart, and subsequently delivering a valve assembly of the prosthetic mitral valve into engagement with the anchor assembly.

10. The method of claim 9, wherein the prosthetic mitral valve comprises a hub, and wherein a first catheter of the multiple catheters is releasably coupleable to the hub.

11. The method of claim 10, further comprising adjusting one or more control wires that extend through a second catheter of the multiple catheters and that are releasably coupled with the anchor assembly of the prosthetic mitral valve.

12. The method of claim 11, wherein at least one of the clamps includes a mechanism for selectively adjusting a tension of the one or more control wires, and wherein expansion of the anchor assembly of the prosthetic mitral valve is controllable by the tension adjustments.

13. A method of implanting a prosthetic mitral valve in a patient, the method comprising:
  inserting, into a patient, a system of multiple catheters configured to deliver the prosthetic mitral valve;
    engaging, to a deployment frame system, the system of multiple catheters, the deployment frame system comprising:
    a plurality of clamps, each clamp of the plurality of clamps configured to releasably clamp a proximal end portion of a respective catheter of the multiple catheters;
    a first frame, wherein each clamp of the plurality of clamps is configured to releasably couple with the first frame;
    a second frame, wherein at least two clamps of the plurality of clamps are configured to releasably couple with the second frame;
    a frame clamp mechanism configured to clamp the second frame to the first frame at a plurality of relative longitudinal orientations between the first frame and the second frame; and
  manipulating the deployment frame system to implant the prosthetic mitral valve in a heart of the patient.

14. The method of claim 13, wherein said manipulating comprises translating the second frame parallel to a longitudinal axis of the first frame.

15. The method of claim 13, wherein said manipulating comprises clamping the at least two clamps to the second frame and translating said at least two of the clamps along the first frame such that a translational movement of the second frame relative to the first frame simultaneously moves said at least two in relation to the first frame.

16. The method of claim 15, wherein the translational movement of the second frame causes corresponding simultaneous movements of two or more catheters of the multiple catheters.

17. The method of claim 13, wherein said manipulating comprises unclamping a respective one of the clamps from a respective catheter and rotating the respective catheter about a longitudinal axis of the respective catheter.

* * * * *